(12) United States Patent
Flynn et al.

(10) Patent No.: US 7,981,843 B2
(45) Date of Patent: Jul. 19, 2011

(54) ANTIBODY SPECIFICITY TRANSFER USING MINIMAL ESSENTIAL BINDING DETERMINANTS

(75) Inventors: Peter Flynn, San Francisco, CA (US); Kenneth Luehrsen, Half Moon Bay, CA (US); Robert F. Balint, Palo Alto, CA (US); Jeng-Horng Her, San Jose, CA (US); Christopher R. Bebbington, San Mateo, CA (US); Geoffrey T. Yarranton, Burlingame, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/040,159

(22) Filed: Jan. 20, 2005

(65) Prior Publication Data

US 2005/0255552 A1 Nov. 17, 2005

Related U.S. Application Data

(60) Provisional application No. 60/546,216, filed on Feb. 23, 2004, provisional application No. 60/537,364, filed on Jan. 20, 2004.

(51) Int. Cl.
C40B 30/04 (2006.01)
C07H 21/04 (2006.01)
(52) U.S. Cl. .................... 506/9; 506/26; 506/23; 506/7; 506/1; 435/7.1; 530/387.1
(58) Field of Classification Search .............. 506/9, 26; 435/7.1; 530/387.1
See application file for complete search history.

(56) References Cited

U.S. PATENT DOCUMENTS

| | | | |
|---|---|---|---|
| 5,225,539 A | 7/1993 | Winter | |
| 5,565,332 A | 10/1996 | Hoogenboom et al. | |
| 5,585,089 A | 12/1996 | Queen et al. | |
| 5,693,761 A | 12/1997 | Queen et al. | |
| 5,693,762 A | 12/1997 | Queen et al. | |
| 5,837,242 A | 11/1998 | Holliger et al. | |
| 5,859,205 A | 1/1999 | Adair et al. | |
| 6,180,370 B1 | 1/2001 | Queen et al. | |
| 6,248,516 B1 * | 6/2001 | Winter et al. | 435/6 |
| 6,350,861 B1 | 2/2002 | Co et al. | |
| 6,548,640 B1 | 4/2003 | Winter | |
| 6,969,586 B1 | 11/2005 | Lerner et al. | |
| 7,063,943 B1 | 6/2006 | McCafferty et al. | |
| 7,087,409 B2 * | 8/2006 | Barbas et al. | 435/69.6 |
| 7,258,985 B2 * | 8/2007 | Maur et al. | 435/7.1 |
| 7,414,121 B2 * | 8/2008 | Hansen et al. | 536/23.4 |
| 7,491,516 B2 * | 2/2009 | Collinson et al. | 435/70.21 |
| 2003/0166871 A1 | 9/2003 | Barbas et al. | |
| 2004/0208888 A1 | 10/2004 | Frank et al. | |
| 2005/0255552 A1 | 11/2005 | Flynn et al. | |

FOREIGN PATENT DOCUMENTS

WO WO 02/00005 A2 1/2002
WO WO 2004/006955 A1 1/2004

OTHER PUBLICATIONS

Proba et al, J. Mol. Biol. 1998, 275, 245-253.*
Al-Lazikani, B., "Standard conformations for the canonical structures of immunoglobulines," *J. Mol. Biol.*, vol. 273, pp. 927-948 (1997).
Bajorath, J., et al., "Conformational similarity and systematic displacement of complementarity determining region loops in high resolution antibody x-ray structures," *J. Bio. Chem.*, vol. 270(38), pp. 22081-22084 (1995).
Jones, P., et al., "Replacing the complementarity-determining regions in a human antibody with those from a mouse," *Nature*, vol. 321, pp. 522-525 (May 29, 1986).
Marks, J., et al., "By-passing immunization: Building high affinity human antibodies by chain shuffling," *Bio/Technology*, vol. 10, pp. 779-783 (1992).
Martin, A. et al., "Molecular modeling of antibody combining sites," *Methods Enzymol.*, vol. 203, pp. 121-153 (1991).
Rader, C., et al., "A phage display approach for rapid antibody humanization: designed combinatorial V gene libraries," *PNAS*, vol. 95, pp. 8910-8915 (Jul. 1998).
Rader, C., et al., "The rabbit antibody repertoire as a novel source for the generation of therapeutic human antibodies," *The Journal of Biological Chemistry*, vol. 275(18), pp. 13668-13676 (2000).
Steinberger, P., et al., "Generation and characterization of recombinant human CCR5-specific antibody," *J. Biol. Chem.*, vol. 275(46), pp. 36073-36078 (2000).
U.S. Appl. No. 11/282,107, filed Nov. 16, 2005, Bebbington et al.
Beiboer, S.H. et al., "Guided selection of a pan carcinoma specific antibody reveals similar binding characteristics yet structural divergence between the original murine antibody and its human equivalent," 2000, *J. Mol. Biol.*, vol. 296(3), pp. 833-849.
Chung, J. et al., "Integrin $\alpha_{IIb}\beta_3$ specific synthetic human monoclonal antibodies and HCDR3 peptides that potently inhibit platelet aggregation," Epub Dec. 19, 2003, *FASEB J*, 23 pages. (*Final version cited as*: 2004, vol. 18(2), pp. 361-363).
Daugherty, P.S. et al., "Development of an optimized expression system for the screening of antibody libraries displayed on the *Escherichia coli* surface," 1999, *Protein Engineering*, vol. 12(7), pp. 613-621.
Feldhaus, M.J. et al., "Flow-cytometric isolation of human antibodies from a nonimmune *Saccharomyces cerevisiae* surface display library," 2003, *Nature Biotechnology*, vol. 21(2), pp. 163-170.

(Continued)

*Primary Examiner* — T. D. Wessendorf
(74) *Attorney, Agent, or Firm* — Kilpatrick Townsend & Stockton

(57) ABSTRACT

The present invention provides methods of making antibodies having the binding specificity of a reference antibody. Antibodies generated by the methods of the inventions have at least one minimal essential binding specificity determinant from a heavy chain or light chain CDR3 from the reference antibody. The method can be used, e.g., in humanization procedures. The invention also provides libraries and antibodies made in accordance with the methods.

14 Claims, 11 Drawing Sheets

OTHER PUBLICATIONS

Hoogenboom, H.R. and G. Winter, "By-passing immunisation. Human antibodies from synthetic repertoires of germline VH gene segments rearranged in vitro," 1992, *J. Mol. Biol.*, vol. 227(2), pp. 381-388.

Jespers, L. et al., "Guiding the selection of human antibodies from phage display repertoires to a single epitope of an antigen," 1994, *Bio/technology*, vol. 12(9), pp. 899-903.

Jirholt, P. et al., "Exploiting sequence space: shuffling in vivo formed complementarity determining regions into a master framework," 1998, *Gene*, vol. 215(2), pp. 471-476.

Klimka, A. et al., "Human anti-CD30 recombinant antibodies by guided phage antibody selection using cell panning," 2000, *Br. J. Cancer*, vol. 83(2), pp. 252-260.

Marks, J.D. et al., "By-passing immunization: Human antibodies from V-gene libraries displayed on phage," 1991, *J. Mol. Biol.*, vol. 222(3), pp. 581-597.

Queen, C. et al., "A humanized antibody that binds to the interleukin 2 receptor," 1989, *PNAS*, vol. 86(24), pp. 10029-10033.

Riechmann, L. et al., "Reshaping human antibodies for therapy," 1988, *Nature*, vol. 332, pp. 323-327.

Söderlind, E. et al., "Recombining germline-derived CDR sequences for creating diverse single-framework antibody libraries," 2000, *Nature Biotechnology*, vol. 18(8), pp. 852-856.

Verhoeyen, M. et al., "Reshaping human antibodies: grafting an antilysozyme activity," 1988, *Science*, vol. 239, pp. 1534-1536.

Winter, G. et al., "Making antibodies by phage display technology," 1994, *Annu. Rev. Immunol.*, vol. 12, pp. 433-455.

\* cited by examiner

Figure 2

```
GATCCTACCTGACGCTTTTTATCGCAACTCTCTACTGTTTCTCCATACCCGTTTTTTGGG
TCTTCCCGCCATCTGATGAGCAGTTGAAATCTGGAACTGCCTCTGTTGTGTGCCTGCTGA
CCCATCAGGGCCTGAGTTCACCGGTGACAAAGAGCTTCAACAGGGGAGAGTGTTAATAAG
CTGGATTGTTATTACTCGCGGCCCAGCCGGCCATGGTGATTTAAATCATTAGTATACTAA
GGCCCGCCCAGCTCCGGAAGCACCAAGGGCCCATCGGTCTTCCCCCTGGCACCCTCCTCC
AAGAGCACCTCTGGGGCACAGCGGCCCTGGGCTGCCTGGTCAAGGACTACTTCCCCGAA
CCGGTGACGGTGTCGTGGAACTCAGGCGCCCTGACCAGCGGCGTCCACACCTTCCCGGCT
GTCCTACAGTCCTCAGGACTCTACTCCCTCAGCAGCGTAGTGACCGTGCCCTCCAGCAGC
TTGGGCACCCAGACCTACATCTGCAACGTGAATCACAAGCCCAGCAACACCAAGGTGGAC
AAGAAAGTTGAGCCCAAATCTTGTGCGGCCGGAGCTAGCCATCATCATCACCATCACGGG
GCCGCAGAACAAAAACTCATCTCAGAAGAGGATCTGAATGGGGCCGCATAGACTGTTGAA
AGTTGTTTAGCAAAACCTCATACAGAAAATTCATTTACTAACGTCTGGAAAGACGACAAA
ACTTTAGATCGTTACGCTAACTATGAGTCTAGATGAATTCACTGGCCGTCGTTTTACAAC
GTCGTGACTGGGAAAACCCTGGCGTTACCCAACTTAATCGCCTTGCAGCACATCCCCCTT
TCGCCAGCTGGCGTAATAGCGAAGAGGCCCGCACCGATCGCCCTTCCCAACAGTTGCGCA
GCCTGAATGGCGAATGGCGCCTGATGCGGTATTTTCTCCTTACGCATCTGTGCGGTATTT
CACACCGCATACGTCAAAGCAACCATAGTACGCGCCCTGTAGCGGCGCATTAAGCGCGGC
GGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAA
TCGGGGGCTCCCTTTAGGGTTCCGATTTAGTGCTTTACGGCACCTCGACCCCAAAAAACT
TGATTTGGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAACACTCAA
CCCTATCTCGGGCTATTCTTTTGATTTATAAGGGATTTTGCCGATTTCGGCCTATTGGTT
AAAAAATGAGCTGATTTAACAAAAATTTAACGCGAATTTTAACAAAATATTAACGTTTAC
AATTTTATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGCTTA
CAGACAAGCTGTGACCGTCTCCGGGAGCTGCATGTGTCAGAGGTTTTCACCGTCATCACC
GAAACGCGCGAGACGAAAGGGCCTCGTGATACGCCTATTTTTATAGGTTAATGTCATGAT
AATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATA
AATGCTTCAATAATATTGAAAAAGGAAGAGTATGCATAAAAAAATCACTGGATATACCAC
CGTTGATATATCCCAATGGCATCGTAAAGAACATTTTGAGGCATTTCAGTCAGTTGCTCA
ATGTACCTATAACCAGACCGTTCAGCTGGATATTACGGCCTTTTTAAAGACCGTAAAGAA
AAATAAGCACAAGTTTTATCCGGCCTTTATTCACATTCTTGCCCGCCTGATGAATGCTCA
TCCAGAGTTCCGTATGGCAATGAAAGACGGTGAGCTGGTGATATGGGATAGTGTTCACCC
TTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAA
CCTGGCCTATTTCCCTAAAGGGTTTATTGAGAATATGTTTTTCGTCTCAGCCAATCCCTG
GGTGAGTTTCACCAGTTTTGATTTAAACGTGGCCAATATGGACAACTTCTTCGCCCCCGT
TTTCACGATGGGCAAATATTATACGCAAGGCGACAAGGTGCTGATGCCGCTGGCGATTCA
GGTTCATCATGCCGTCTGTGATGGCTTCCATGTCGGCAGAATGCTTAATGAATTACAACA
GTACTGCGATGAGTGGCAGGGCGGGGCGTAACTAGCTAGTCTGTCAGACCAAGTTTACTC
ATATATACTTTAGATTGATTTAAAACTTCATTTTTAATTTAAAAGGATCTAGGTGAAGAT
CCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTC
GTGCACACAGCCCAGCTTGGAGCGAACGACCTACACCGAACTGAGATACCTACAGCGTGA
GCATTGAGAAAGCGCCACGCTTCCCGAAGGGAGAAAGGCGGACAGGTATCCGGTAAGCG
G
CAGGGTCGGAACAGGAGAGCGCACGAGGGAGCTTCCAGGGGGAAACGCCTGGTATCTTT
A
TAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTG
```

Figure 2 – con't.

```
CTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGG
TATTTCACACCGCATATGGTGCACTCTCAGTACAATCTGCTCTGATGCCGCATAGTTAAG
CCAGTAGACACTCCGCTATCGCTACGTGACTGGGTCATGGCTGCGCCCCGACACCCGCCA
ACACCCGCTGACGCGCCCTGACGGGCTTGTCTGCTCCCGGCATCCGCTTACAGACAAGCT
GTGACCGTCTCCGGGAGCTGCATGTGTCAGAGGTTTTCACCGTCATCACCGAAACGCGCG
AGGCAGCAGATCAATTCGCTCGCGAAGGCGAAGCGGCATGCATAATGTGCCTGTCAAATG
GACGAAGCAGGGATTCTGCAAACCCTATGCTACTCCGTCAAGCCGTCAATTGTCTGATTC
GTTACCAATTATGACAACTTGACGGCTACATCATTCACTTTTTCTTCACAACCGGCACGG
AACTCGCTCGGGCTGGCCCCGGTGCATTTTTTAAATACCCGCGAGAAATAGAGTTGATCG
TCAAAACCAACATTGCGACCGACGGTGGCGATAGGCATCCGGGTGGTGCTCAAAAGCAGC
TTCGCCTGGCTGATACGTTGGTCCTCGCGCCAGCTTAAGACGCTAATCCCTAACTGCTGG
CGGAAAAGATGTGACAGACGCGACGGCGACAAGCAAACATGCTGTGCGACGCTGGCGAT
A
TCAAAATTGCTGTCTGCCAGGTGATCGCTGATGTACTGACAAGCCTCGCGTACCCGATTA
TCCATCGGTGGATGGAGCGACTCGTTAATCGCTTCCATGCGCCGCAGTAACAATTGCTCA
AGCAGATTTATCGCCAGCAGCTCCGAATAGCGCCCTTCCCCTTGCCCGGCGTTAATGATT
TGCCCAAACAGGTCGCTGAAATGCGGCTGGTGCGCTTCATCCGGGCGAAAGAACCCCGTA
TTGGCAAATATTGACGGCCAGTTAAGCCATTCATGCCAGTAGGCTCGCGGACGAAAGTAA
ACCCACTGGTGATACCATTCGCGAGCCTCTGGATGACGACCGTAGTGATGAATCTCTCCT
GGCGGGAACAGCAAAATATCACCCGGTCGGCAAACAAATTCTCGTCCCTGATTTTTCACC
ACCCCCTGACCGCGAATGGTGAGATTGAGAATATAACCTTTCATTCCCAGCGGTCGGTCG
ATAAAAAAATCGAGATAACCGTTGGCCTCAATCGGCGTTAAACCCGCCACCAGATGGGCA
TTAAACGAGTATCCCGGCAGCAGGGGATCATTTTGCGCTTCAGCCATACTTTTCATACTC
CCGCCATTCAGAGAAGAAACCAATTGTCCATATTGCATCAGACATTGCCGTCACTGCGTC
TTTTACTGGCTCTTCTCGCTAACCAAACCGGTAACCCCGCTTATTAAAAGCATTCTGTAA
CAAAGCGGGACCAAAGCCATGACAAAAACGCGTAACAAAAGTGTCTATAATCACGGCAG
A
AAAGTCCACATTGATTATTTGCACGGCGTCACACTTTGCTATGCCATAGCATTTTTATCC
ATAAGATTAGCG
```

Figure 4

ACGTTATCGACTGCACGGTGCACCAATGCTTCTGGCGTCAGGCAGCCATCGGAAGCTGTG
GTATGGCTGTGCAGGTCGTAAATCACTGCATAATTCGTGTCGCTCAAGGCGCACTCCCGT
TCTGGATAATGTTTTTTGCGCCGACATCATAACGGTTCTGGCAAATATTCTGAAATGAGC
TGTTGACAATTAATCATCGGCTCGTATAATGTGTGGAATTGTGAGCGGATAACAATTTCA
CACAGGAAACAGTATTCAAGCTTATGGGTAAGAAACAGTTGGTTGTGTTTGCTCTGCTTT
TGGCTTTTCTTTCTCCGGCCATGGCGCGCACTTAGCGATATCGTATACTACTGCGCACGT
CGACACTAGTGCTGCACCATCTGTCTTCATCTTCCCGCCATCTGATGAGCAGTTGAAATC
TGGAACTGCCTCTGTTGTGCCTGCTGAATAACTTCTATCCCAGAGAGGCCAAAGTACA
GTGGAAGGTGGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGTTCACCGGTGACAAA
GAGCTTCAACAGGGGAGAGTGTTAAATCGATTAACTAGCATAACCCCTTGGGGCCTCTAA
ACGGGTCTTGAGGGGTTTGAATTCACTGGCCGTCGTTTTACAACGTCGTGACTGGGAAAA
CCCTGGCGTTACCCAACTTAATCGCCTTGCAGCACATCCCCCTTTCGCCAGCTGGCGTAA
TAGCGAAGAGGCCCGCACCGATCGCCCTTCCCAACAGTTGCGCTGTGGTATGGCTGTGCA
GGTCGTAAATCACTGCATAATTCGTGTCGCTCAAGGCGCACTCCCGTTCTGGATAATGTT
TTTTGCGCCGACATCATAACGGTTCTGGCAAATATTCTGAAATGAGCTGTTGACAATTAA
TCATCGGCTCGTATAATGTGTGGAATTGTGAGCGGATAACAATTTCACACAGGAAACAGT
ATTCCTCGAGATGGGTAAGAAACAGTTGGTTGTGTTTGCTCTGCTTTTGGCTTTTCTTTC
TCCGGCCATGGCGCGCACTTAGCGATATCGTATACTACTGCGCACGTCGACACTAGTCCG
GAAGCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGT
GGAACTCAGGCGCCCTGACCAGCGGCGTCCACACCTTCCCGGCTGTCCTACAGTCCTCAG
GACTCTACTCCCTCAGCAGCGTAGTGACCGTGCCCTCCAGCAGCTTGGGCACCCAGACCT
ACATCTGCAACGTGAATCACAAGCCCAGCAACACCAAGGTGGACAAGAAAGTTGAGCCCA
AATCTTGTACGCATACTTGTCCACCTTGTCCAGCAGGGGCCGCAGAACAAAAACTCATCT
CAGAAGAGGATCTGAATTAAGCGGCCGCATCGTGACTGACTGACGATCTGCCTCGCGCGT
TTCGGTGATGACGGTGAAAACCTCTGACACATGCAGCTCCCGGAGACGGTCACAGCTTGT
CTGTAAGCGGATGCCGGGAGCAGACAAGCCCGTCAGGGCGCGTCAGCGGGTGTTGGCGGG
TGTCGGGGCGCAGCCATGACCCAGTCACGTAGCGATAGCGGAGTGTATAATTCTTGAAGA
CGAAAGGGCCTCGTGATACGCCTATTTTTATAGGTTAATGTCATGATAATAATGGTTTCT
TAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAA
TATTGAAAAAGGAAGAGTATGCATAAAAAAATCACTGGATATACCACCGTTGATATATCC
CAATGGCATCGTAAAGAACATTTTGAGGCATTTCAGTCAGTTGCTCAATGTACCTATAAC
CAGACCGTTCAGCTGGATATTACGGCCTTTTTAAAGACCGTAAAGAAAAATAAGCACAAG
TTTTATCCGGCCTTTATTCACATTCTTGCCCGCCTGATGAATGCGCACCCGGAGTTCCGT
ATGGCAATGAAAGACGGTGAGCTGGTGATATGGGATAGTGTTCACCCTTGTTACACCGTT
TTCCATGAGCAAACTGAAACGTTTTCATCGCTCTGGAGTGAATACCACGACGATTTCCGG
CAGTTTCTACACATATATTCGCAAGATGTGGCGTGTTACGGTGAAAACCTGGCCTATTTC
CCTAAAGGGTTTATTGAGAATATGTTTTTCGTCTCAGCCAATCCCTGGGTGAGTTTCACC
AGTTTTGATTTAAACGTGGCCAATATGGACAACTTCTTCGCCCCCGTTTTCACGATGGGC
AAATATTATACGCAAGGCGACAAGGTGCTGATGCCGCTGGCGATTCAGGTTCATCATGCC
GTCTGTGATGGCTTCCATGTCGGCAGAATGCTTAATGAATTACAACAGTACTGCGATGAG
TGGCAGGGCGGGGCGTAATCTAGTCTGTCAGACCAAGTTTACTCATATATACTTTAGATT
GATTTAAAACTTCATTTTTAATTTAAAAGGATCTAGGTGAAGATCCTTTTTGATAATCTC
ATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGCCGTAG
TTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGC

Figure 4—con't.

```
TTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCCTTTTGCTCAC
ATGTTCTTTCCTGCGTTATCCCCTGATTCTGTGGATAACCGTATTACCGCCTTTGAGTGA
GCTGATACCGCTCGCCGCAGCCGAACGACCGAGCGCAGCGAGTCAGTGAGCGAGGAAGCG
GAAGAGCGCCTGATGCGGTATTTTCTCCTTACGCATCTGTGCGGTATTTCACACCGCATA
AATTCCGACACCATCGAATGGTGCAAAACCTTTCGCGGTATGGCATGATAGCGCCCGGAA
GAGAGTCAATTCAGGGTGGTGAATGTGAAACCAGTAACGTTATACGATGTCGCAGAGTAT
GCCGGTGTCTCTTATCAGACCGTTTCCCGCGTGGTGAACCAGGCCAGCCACGTTTCTGCG
AAAACGCGGGAAAAAGTGGAAGCGGCGATGGCGGAGCTGAATTACATTCCCAACCGCGTG
GCACAACAACTGGCGGGCAAACAGTCGTTGCTGATTGGCGTTGCCACCTCCAGTCTGGCC
CTGCACGCGCCGTCGCAAATTGTCGCGGCGATTAAATCTCGCGCCGATCAACTGGGTGCC
AGCGTGGTGGTGTCGATGGTAGAACGAAGCGGCGTCGAAGCCTGTAAAGCGGCGGTGCAC
AATCTTCTCGCGCAACGCGTCAGTGGGCTGATCATTAACTATCCGCTGGATGACCAGGAT
GCCATTGCTGTGGAAGCTGCCTGCACTAATGTTCCGGCGTTATTTCTTGATGTCTCTGAC
CAGACACCCATCAACAGTATTATTTTCTCCCATGAAGACGGTACGCGACTGGGCGTGGAG
CATCTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAGCCG
ATAGCGGAACGGGAAGGCGACTGGAGTGCCATGTCCGGTTTTCAACAAACCATGCAAATG
CTGAATGAGGGCATCGTTCCCACTGCGATGCTGGTTGCCAACGATCAGATGGCGCTGGGC
GCAATGCGCGCCATTACCGAGTCCGGGCTGCGCGTTGGTGCGGATATCTCGGTAGTGGGA
TACGACGATACCGAAGACAGCTCATGTTATATCCGCCGTTAACCACCATCAAACAGGAT
TTTCGCCTGCTGGGGCAAACCAGCGTGGACCGCTTGCTGCAACTCTCTCAGGGCCAGGCG
GTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAG
GTTTCCCGACTGGAAAGCGGGCAGTGAGCGCAACGCAATTAATGTGAGTTAGCTCACTCA
TTAGGCACCCCAGGCTTTACACTTTATGCTTCCGGCTCGTATGTTGTGTGGAATTGTGAG
CGGATAACAATTTCACACAGGAAACAGCTATGACCATGATTACGGATTCACTGGCCGTCG
TTTTACAACGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCCTTCCCAAC
AGTTGCGCAGCCTGAATGGCGAATGGCGCTTTGCCTGGTTTCCGGCACCAGAAGCGGTGC
CGGAAAGCTGGCTGGAGTGCGATCTTCCTGAGGCCGATACTGTCGTCGTCCCCTCAAACT
GGCAGATGCACGGTTACGATGCGCCCATCTACACCAACGTAACCTATCCCATTACGGTCA
ATCCGCCGTTTGTTCCCACGGAGAATCCGACGGGTTGTTACTCGCTCACATTTAATGTTG
ATGAAAGCTGGCTACAGGAAGGCCAGACGCGAATTATTTTTGATGGCGTTGGAATT
```

Figure 5

|  | N-addition | D segment | N-addition | Jh-CDR3 | Jh-Fr4 | |
|---|---|---|---|---|---|---|
| Mab166 | NRGD | IYYD | FT | YAMDY | WGQGTSVTVSS | |
|  |  |  |  | YYYYYGMDV | WGQGTTVTVSS | JH6 |
|  |  |  |  | -AFDI | WGQGTMVTVSS | JH3 |

Figure 6

BA130-1-1D Vh: QVQLVESGAEVKKPGSSVKVSCKASGGTFSSYAISWVRQAPGQGLEWMGGIIPIFGTANY
AQKFQGRVTITADESTSTAYMELSSLRSEDTAVYYCARNRGDIYYDFTYGMDVWGQGTTVTVSS

BA130-1-1D Vk: ALDIQMTQSPSSLSASVGDRVTITCRASQSISTYLNWYQQRPGKAPKLLIYAASRLLNGV
PSRFSGSGSGTDFTLTISGLQPEDIATYYCQHFWSTPYTFGQGTKLEIK

BA130-5-E10 Vh: EVQLVESGAEVKKPGASVKVSCKASGYTFTGYYMHWVRQAPGQGLEWMGWINPNSGGTNY
AQKFQGWVTMTRDTSISTAYMELSRLRSDDTAVYYCARNRGDIYYDFTYGMDVWGQGTTVTVSS

BA130-5-E10 Vk: ALDIQMTQSPSSLSASVGDRVTITCRASQSISTYLNWYQQRPGKAPKLLIYAASRLLNGV
PSRFSGSGSGTDFTLTISGLQPEDIATYYCQHFWSTPYTFGQGTKLEIK

Figure 7 a) Antibody BA133-5-E6

BA133-5-E6 Vh: EVQLVESGAEVKKPGASVKVSCKASGYTFTSYGISWVRQAPGQGLEWMGWISAYNGNTNY
AQKLQGRVTITTDTATRTTYMDLRSLRSDDTAVYYCARNRGDIYYDFTYAFDIWGQGTMVTVSS

BA133-5-E6 Vk: ALDIQMTQSPSSLSASVGDRVTITCRASQSISTYLNWYQQRPGKAPKLLIYAASRLLNGV
PSRFSGSGSGTDFTLTISGLQPEDIATYYCQHFWSTPYTFGQGTKLEIK b) Antibody BA133-6-F5

BA133-6-F5 Vh: QVQLVESGPEVKKPGTSVKVSCKASGFTFTSSAMQWVRQARGQRLEWIGWIIVGSGNTNY
AQKFQERVTITRDMSTSTAYMELSSLRAEDTAVYYCARNRGDIYYDFTYAFDIWGQGTMVTVSS

BA133-6-F5 Vk: ALDIQMTQSPSSLSASVGDRVTITCRASQSISTYLNWYQQRPGKAPKLLIYAASRLLNGV
PSRFSGSGSGTDFTLTISGLQPEDIATYYCQHFWSTPYTFGQGTKLEIK

Figure 8
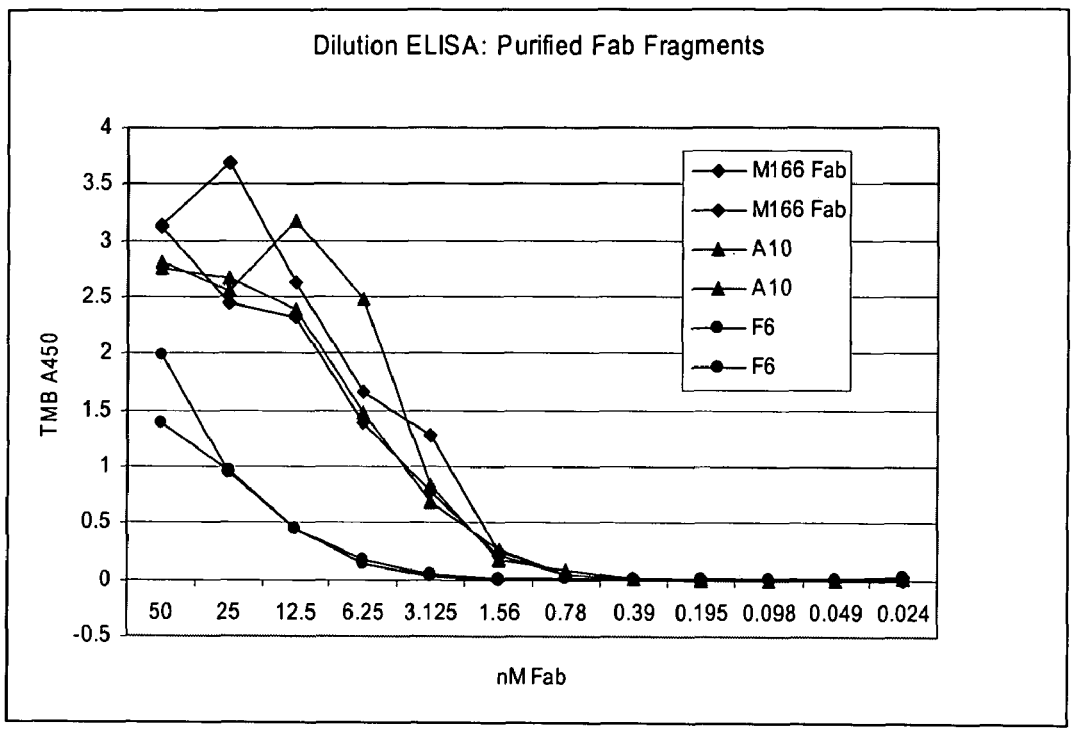
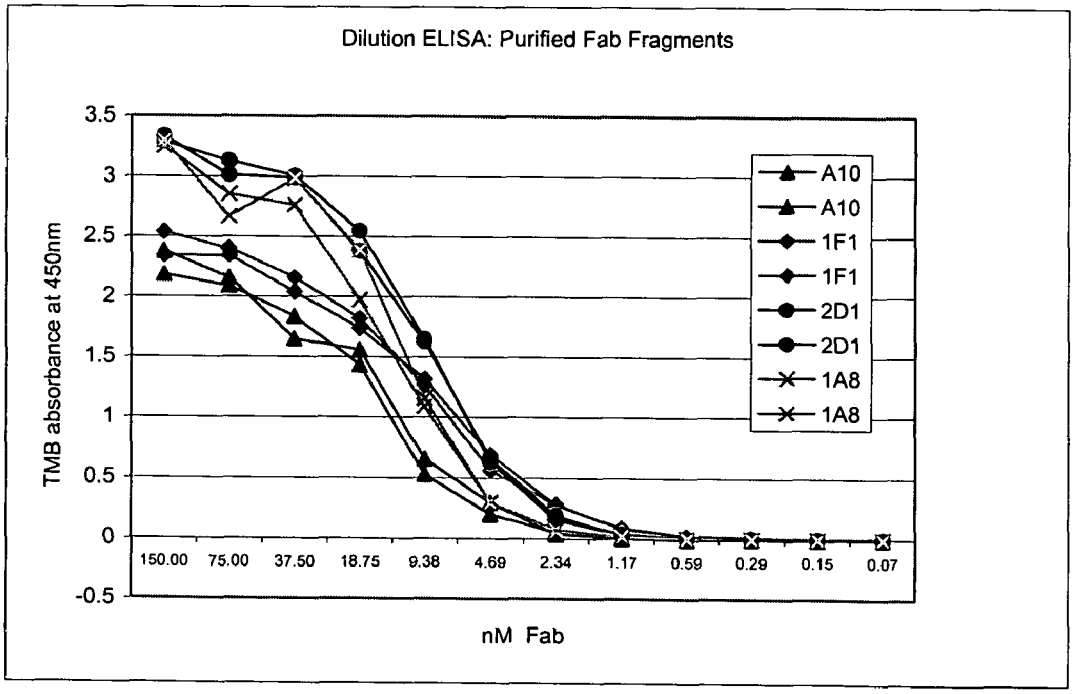

Figure 9

F6 VH: EVQLVESGGGVVQPGRSLRLSCAASGFTFSSYGMHWVRQAPGKGLEWVAVIWYDGSNKYY
ADSVKGRFTISRDNSKNTLYLQMNSLRAEDTAVYYCARNRGDIYYDFTYAMDYWGQGTSVTVSS

F6 VL: EIVLTQSPGTLSLSPGERATLSCTASQALISSTLAWYQQKPGQAPRLLIFGASSRATGTP
DRFSGSGSGTDFTLTISRLEPEDFAVYYCQHFWSTPYTFGGGTKLEIK

1F1 VH: EVQLVESGGGVVQPGRSLRLSCAASGFTFSNYPMHWVRQAPGKGLEWVAVISYDGSEKWY
ADSVKGRFTISRDNSKNTLYLEMNSLRPEDTAVYYCARNRGDIYYDFTYAMDYWGQGTSVTVSS

1F1 VL: EIVLTQSPATLSLSPGERATLSCRASQSVSSYLAWYQQKPGQAPRLLIYDASNRATGIPA
RFSGSGSGTDFTLTISSLEPEDFAVYYCQHFWSTPYTFGGGTKLEIK

SEQUENCE LISTING

<160> NUMBER OF SEQ ID NOS: 133

<210> SEQ ID NO 1
<211> LENGTH: 4992
<212> TYPE: DNA
<213> ORGANISM: Artificial Sequence
<220> FEATURE:
<223> OTHER INFORMATION: Description of Artificial Sequence:complete
      sequence of plasmid vector KB1082 for expression
      of Fab fragments in E. coli

<400> SEQUENCE: 1

```
gatcctacct gacgcttttt atcgcaactc tctactgttt ctccataccc gttttttggg      60
tcttcccgcc atctgatgag cagttgaaat ctggaactgc ctctgttgtg tgcctgctga     120
cccatcaggg cctgagttca ccgtgacaa agagcttcaa caggggagag tgttaataag      180
ctggattgtt attactcgcg gcccagccgg ccatggtgat ttaaatcatt agtatactaa     240
ggcccgccca gctccggaag caccaagggc ccatcggtct tcccctggc accctcctcc      300 aagagcacct ctggggcac agcggccctg gctgcctgg tcaaggacta cttccccgaa       360
ccggtgacgg tgtcgtggaa ctcaggcgcc ctgaccagcg gcgtccacac cttcccggct     420
gtcctacagt cctcaggact ctactccctc agcagcgtag tgaccgtgcc ctccagcagc     480
ttgggcaccc agacctacat ctgcaacgtg aatcacaagc ccagcaacac caaggtggac     540
aagaaagttg agcccaaatc ttgtgcggcc ggagctagcc atcatcatca ccatcacggg    600
gccgcagaac aaaaactcat ctcagaagag gatctgaatg gggccgcata gactgttgaa     660
agttgtttag caaaacctca tacagaaaat tcatttacta acgtctggaa agacgacaaa     720
actttagatc gttacgctaa ctatgagtct agatgaattc actggccgtc gttttacaac     780
gtcgtgactg ggaaaaccct ggcgttaccc aacttaatcg ccttgcagca catccccctt     840
tcgccagctg gcgtaatagc gaagaggccc gcaccgatcg cccttcccaa cagttgcgca     900
gcctgaatgg cgaatggcgc ctgatgcggt attttctcct tacgcatctg tgcggtattt     960
cacaccgcat acgtcaaagc aaccatagta cgcgccctgt agcggcgcat taagcgcggc    1020
gggtgtggtg gttacgcgca gcgtgaccgc tacacttgcc agcgccctag cgcccgctcc    1080
tttcgctttc ttcccttcct ttctcgccac gttcgccggc tttccccgtc aagctctaaa    1140 tcggggctc cctttagggt tccgatttag tgctttacgg cacctcgacc ccaaaaaact    1200
tgatttgggt gatggttcac gtagtgggcc atcgccctga tagacggttt ttcgcccttt    1260
gacgttggag tccacgttct ttaatagtgg actcttgttc caaactggaa caacactcaa    1320
ccctatctcg ggctattctt ttgatttata agggattttg ccgatttcgg cctattggtt    1380
aaaaaatgag ctgatttaac aaaaatttaa cgcgaatttt aacaaaatat taacgtttac    1440
aattttatgg tgcactctca gtacaatctg ctctgatgcc gcatagttaa gccagccccg    1500
acacccgcca cacccgctg acgcgccctg acgggcttgt ctgctcccgg catccgctta    1560
cagacaagct gtgaccgtct ccgggagctg catgtgtcag aggttttcac cgtcatcacc    1620
gaaacgcgcg agacgaaagg gcctcgtgat acgcctattt ttataggtta atgtcatgat    1680
aataatggtt tcttagacgt caggtggcac ttttcgggga aatgtgcgcg gaacccctat    1740
```

```
ttgtttattt ttctaaatac attcaaatat gtatccgctc atgagacaat aaccctgata   1800
aatgcttcaa taatattgaa aaaggaagag tatgcataaa aaaatcactg gatataccac   1860
cgttgatata tcccaatggc atcgtaaaga acattttgag gcatttcagt cagttgctca   1920
atgtacctat aaccagaccg ttcagctgga tattacggcc tttttaaaga ccgtaaagaa   1980
aaataagcac aagttttatc cggcctttat tcacattctt gcccgcctga tgaatgctca   2040
tccagagttc cgtatggcaa tgaaagacgg tgagctggtg atatgggata gtgttcaccc   2100
ttgttcacac gttttccatg agcaaactga aacgttttca tcgctctgga gtgaatacca   2160
cgacgatttc cggcagtttc tacacatata ttcgcaagat gtggcgtgtt acggtgaaaa   2220
cctggcctat ttccctaaag ggtttattga gaatatgttt ttcgtctcag ccaatccctg   2280
ggtgagtttc accagttttg atttaaacgt ggccaatatg gacaacttct tcgcccccgt   2340
tttcacgatg ggcaaatatt atacgcaagg cgacaaggtg ctgatgccgc tggcgattca   2400
ggttcatcat gccgtctgtg atggcttcca tgtcggcaga atgcttaatg aattacaaca   2460
gtactgcgat gagtggcagg cggggcgta actagctagt ctgtcagacc aagtttactc   2520
atatatactt tagattgatt taaaacttca tttttaattt aaaaggatct aggtgaagat   2580 ccttttttgat aatctcatga ccaaaatccc ttaacgtgag ttttcgttcc actgagcgtc   2640 agacccgta gaaaagatca aaggatcttc ttgagatcct ttttttctgc gcgtaatctg   2700
ctgcttgcaa acaaaaaaac caccgctacc agcggtggtt tgtttgccgg atcaagagct   2760
accaactctt tttccgaagg taactggctt cagcagagcg cagataccaa atactgtcct   2820
tctagtgtag ccgtagttag gccaccactt caagaactct gtagcaccgc ctacatacct   2880
cgctctgcta atcctgttac cagtggctgc tgccagtggc gataagtcgt gtcttaccgg   2940
gttggactca agacgatagt taccggataa ggcgcagcgg tcgggctgaa cggggggttc   3000
gtgcacacag cccagcttgg agcgaacgac ctacaccgaa ctgagatacc tacagcgtga   3060
gcattgagaa agcgccacgc ttcccgaagg gagaaaggcg gacaggtatc cggtaagcgg   3120
cagggtcgga acaggagagc gcacgaggga gcttccaggg ggaaacgcct ggtatcttta   3180
tagtcctgtc gggtttcgcc acctctgact tgagcgtcga ttttttgtgat gctcgtcagg   3240 ggggcggagc ctatgaaaaa acgccagcaa cgcggccttt ttacggttcc tggccttttg   3300 ctggccttt gctcacatgt tctttcctgc gttatcccct gattctgtgg ataaccgtat   3360
taccgccttt gagtgagctg ataccgctcg ccgcagccga acgaccgagc gcagcgagtc   3420
agtgagcgag gaagcggaag agcgcctgat gcggtatttt ctccttacgc atctgtgcgg   3480
tatttcacac cgcatatggt gcactctcag tacaatctgc tctgatgccg catagttaag   3540
ccagtagaca ctccgctatc gctacgtgac tgggtcatgg ctgcgccccg acacccgcca   3600
acacccgctg acgcgccctg acgggcttgt ctgctcccgg catccgctta cagacaagct   3660
gtgaccgtct ccgggagctg catgtgtcag aggttttcac cgtcatcacc gaaacgcgcg   3720
aggcagcaga tcaattcgct cgcgaaggcg aagcggcatg cataatgtgc ctgtcaaatg   3780
gacgaagcag ggattctgca aaccctatgc tactccgtca agccgtcaat tgtctgattc   3840
gttaccaatt atgacaactt gacggctaca tcattcactt tttcttcaca accggcacgg   3900
aactcgctcg ggctggcccc ggtgcatttt ttaaataccc gcgagaaata gagttgatcg   3960
tcaaaaccaa cattgcgacc gacggtggcg ataggcatcc gggtggtgct caaaagcagc   4020
ttcgcctggc tgatacgttg gtcctcgcgc cagcttaaga cgctaatccc taactgctgg   4080
cggaaaagat gtgacagacg cgacggcgac aagcaaacat gctgtgcgac gctggcgata   4140
```

```
tcaaaattgc tgtctgccag gtgatcgctg atgtactgac aagcctcgcg tacccgatta   4200
tccatcggtg gatggagcga ctcgttaatc gcttccatgc gccgcagtaa caattgctca   4260
agcagattta tcgccagcag ctccgaatag cgcccttccc cttgcccggc gttaatgatt   4320
tgcccaaaca ggtcgctgaa atgcggctgg tgcgcttcat ccgggcgaaa gaacccgta    4380 ttggcaaata ttgacggcca gttaagccat tcatgccagt aggctcgcgg acgaaagtaa   4440
acccactggt gataccattc gcgagcctct ggatgacgac cgtagtgatg aatctctcct   4500
ggcgggaaca gcaaaatatc acccggtcgg caaacaaatt ctcgtccctg atttttcacc   4560
accccctgac cgcgaatggt gagattgaga atataacctt tcattcccag cggtcggtcg   4620
ataaaaaaat cgagataacc gttggcctca atcggcgtta aacccgccac cagatgggca   4680
ttaaacgagt atcccggcag caggggatca ttttgcgctt cagccatact tttcatactc   4740
ccgccattca gagaagaaac caattgtcca tattgcatca gacattgccg tcactgcgtc   4800
ttttactggc tcttctcgct aaccaaaccg gtaaccccgc ttattaaaag cattctgtaa   4860
caaagcggga ccaaagccat gacaaaaacg cgtaacaaaa gtgtctataa tcacggcaga   4920
aaagtccaca ttgattattt gcacggcgtc acactttgct atgccatagc attttatcc    4980 ataagattag cg                                                      4992
```

<210> SEQ ID NO 2
<211> LENGTH: 5396
<212> TYPE: DNA
<213> ORGANISM: Artificial Sequence
<220> FEATURE:
<223> OTHER INFORMATION: Description of Artificial Sequence:complete
      sequence of plasmid vector KB5000 for expression
      of Fab' fragments in E. coli

<400> SEQUENCE: 2

```
acgttatcga ctgcacggtg caccaatgct tctggcgtca ggcagccatc ggaagctgtg     60
gtatggctgt gcaggtcgta aatcactgca taattcgtgt cgctcaaggc gcactcccgt    120
tctggataat gttttttgcg ccgacatcat aacggttctg gcaaatattc tgaaatgagc    180
tgttgacaat taatcatcgg ctcgtataat gtgtggaatt gtgagcggat aacaatttca    240
cacaggaaac agtattcaag cttatgggta gaaacagtt ggttgtgttt gctctgcttt     300
tggcttttct ttctccggcc atggcgcgca cttagcgata tcgtatacta ctgcgcacgt    360
cgacactagt gctgcaccat ctgtcttcat cttcccgcca tctgatgagc agttgaaatc    420
tggaactgcc tctgttgtgt gcctgctgaa taacttctat cccagagagg ccaaagtaca    480
gtggaaggtg gataacgccc tccaatcggg taactcccag gagagtgtca cagagcagga    540
cagcaaggac agcacctaca gcctcagcag caccctgacg ctgagcaaag cagactacga    600
gaaacacaaa gtctacgcct gcgaagtcac ccatcagggc ctgagttcac cggtgacaaa    660
gagcttcaac aggggagagt gttaaatcga ttaactagca taaccccttg gggcctctaa    720
acgggtcttg aggggttttga attcactggc cgtcgtttta caacgtcgtg actgggaaaa    780
ccctggcgtt acccaactta atcgccttgc agcacatccc cctttcgcca gctggcgtaa    840
tagcgaagag gcccgcaccg atcgcccttc ccaacagttg cgctgtggta ggctgtgca     900 ggtcgtaaat cactgcataa ttcgtgtcgc tcaaggcgca ctcccgttct ggataatgtt    960
ttttgcgccg acatcataac ggttctggca aatattctga atgagctgt tgacaattaa    1020 tcatcggctc gtataatgtg tggaattgtg agcggataac aatttcacac aggaaacagt   1080
attcctcgag atgggtaaga aacagttggt tgtgtttgct ctgcttttgg cttttctttc   1140
```

```
tccggccatg gcgcgcactt agcgatatcg tatactactg cgcacgtcga cactagtccg    1200
gaagcaccaa gggcccatcg gtcttccccc tggcaccctc ctccaagagc acctctgggg    1260
gcacagcggc cctgggctgc ctggtcaagg actacttccc cgaaccggtg acggtgtcgt    1320
ggaactcagg cgccctgacc agcggcgtcc acaccttccc ggctgtccta cagtcctcag    1380
gactctactc cctcagcagc gtagtgaccg tgccctccag cagcttgggc acccagacct    1440
acatctgcaa cgtgaatcac aagcccagca acaccaaggt ggacaagaaa gttgagccca    1500
aatcttgtac gcatacttgt ccaccttgtc cagcaggggc gcagaacaa aaactcatct     1560 cagaagagga tctgaattaa gcggccgcat cgtgactgac tgacgatctg cctcgcgcgt    1620
ttcggtgatg acggtgaaaa cctctgacac atgcagctcc cggagacggt cacagcttgt    1680
ctgtaagcgg atgccgggag cagacaagcc cgtcagggcg cgtcagcggg tgttggcggg    1740
tgtcggggcg cagccatgac ccagtcacgt agcgatagcg gagtgtataa ttcttgaaga    1800
cgaaagggcc tcgtgatacg cctattttta taggttaatg tcatgataat aatggtttct    1860
tagacgtcag gtggcacttt cggggaaat gtgcgcggaa cccctatttg tttattttc      1920 taaatacatt caaatatgta tccgctcatg agacaataac cctgataaat gcttcaataa    1980
tattgaaaaa ggaagagtat gcataaaaaa atcactggat ataccaccgt tgatatatcc    2040
caatggcatc gtaaagaaca ttttgaggca tttcagtcag ttgctcaatg tacctataac    2100
cagaccgttc agctggatat acggcctttt ttaaagaccg taaagaaaaa taagcacaag    2160
ttttatccgg cctttattca cattcttgcc cgcctgatga atgcgcaccc ggagttccgt    2220
atggcaatga aagacggtga gctggtgata tgggatagtg ttcacccttg ttacaccgtt    2280
ttccatgagc aaactgaaac gttttcatcg ctctggagtg aataccacga cgatttccgg    2340
cagtttctac acatatattc gcaagatgtg gcgtgttacg gtgaaaacct ggcctatttc    2400
cctaaagggt ttattgagaa tatgttttc gtctcagcca atccctgggt gagtttcacc     2460
agttttgatt taaacgtggc caatatggac aacttcttcg ccccgttttt cacgatgggc    2520
aaatattata cgcaaggcga caaggtgctg atgccgctgg cgattcaggt tcatcatgcc    2580
gtctgtgatg gcttccatgt cggcagaatg cttaatgaat tacaacagta ctgcgatgag    2640
tggcagggcg gggcgtaatc tagtctgtca gaccaagttt actcatatat actttagatt    2700
gatttaaaac ttcattttta atttaaaagg atctaggtga agatcctttt tgataatctc    2760
atgaccaaaa tcccttaacg tgagttttcg ttccactgag cgtcagaccc cgtagaaaag    2820
atcaaaggat cttcttgaga tcctttttt ctgcgcgtaa tctgctgctt gcaaacaaaa     2880
aaaccaccgc taccagcggt ggtttgtttg ccggatcaag agctaccaac tcttttccg     2940 aaggtaactg gcttcagcag agcgcagata ccaaatactg tccttctagt gtagccgtag    3000
ttaggccacc acttcaagaa ctctgtagca ccgcctacat acctcgctct gctaatcctg    3060
ttaccagtgg ctgctgccag tggcgataag tcgtgtctta ccgggttgga ctcaagacga    3120
tagttaccgg ataaggcgca gcggtcgggc tgaacggggg gttcgtgcac acagcccagc    3180
ttggagcgaa cgacctacac cgaactgaga tacctacagc gtgagctatg agaaagcgcc    3240
acgcttcccg aagggagaaa ggcggacagg tatccggtaa gcggcagggt cggaacagga    3300
gagcgcacga gggagcttcc agggggaaac gcctggtatc tttatagtcc tgtcgggttt    3360
cgccacctct gacttgagcg tcgatttttg tgatgctcgt caggggggcg gagcctatgg    3420
aaaaacgcca gcaacgcggc cttttacgg ttcctggcct tttgctggcc ttttgctcac     3480
atgttctttc ctgcgttatc ccctgattct gtggataacc gtattaccgc ctttgagtga    3540
```

-continued

```
gctgataccg ctcgccgcag ccgaacgacc gagcgcagcg agtcagtgag cgaggaagcg     3600
gaagagcgcc tgatgcggta ttttctcctt acgcatctgt gcggtatttc acaccgcata     3660
aattccgaca ccatcgaatg gtgcaaaacc tttcgcggta tggcatgata gcgcccggaa     3720
gagagtcaat tcagggtggt gaatgtgaaa ccagtaacgt tatacgatgt cgcagagtat     3780
gccggtgtct cttatcagac cgtttcccgc gtggtgaacc aggccagcca cgtttctgcg     3840
aaaacgcggg aaaagtgga agcggcgatg gcggagctga attacattcc caaccgcgtg     3900
gcacaacaac tggcgggcaa acagtcgttg ctgattggcg ttgccacctc agtctggcc     3960 ctgcacgcgc cgtcgcaaat tgtcgcggcg attaaatctc gcgccgatca actgggtgcc     4020
agcgtggtgg tgtcgatggt agaacgaagc ggcgtcgaag cctgtaaagc ggcggtgcac     4080
aatcttctcg cgcaacgcgt cagtgggctg atcattaact atccgctgga tgaccaggat     4140
gccattgctg tggaagctgc ctgcactaat gttccggcgt tatttcttga tgtctctgac     4200
cagacaccca tcaacagtat tattttctcc catgaagacg gtacgcgact gggcgtggag     4260
catctggtcg cattgggtca ccagcaaatc gcgctgttag cgggcccatt aagttctgtc     4320
tcggcgcgtc tgcgtctggc tggctggcat aaatatctca ctcgcaatca aattcagccg     4380
atagcggaac gggaaggcga ctggagtgcc atgtccggtt tcaacaaac catgcaaatg     4440 ctgaatgagg gcatcgttcc cactgcgatg ctggttgcca acgatcagat ggcgctgggc     4500
gcaatgcgcg ccattaccga gtccgggctg cgcgttggtg cggatatctc ggtagtggga     4560
tacgacgata ccgaagacag ctcatgttat atcccgccgt taaccaccat caaacaggat     4620
tttcgcctgc tggggcaaac cagcgtggac cgcttgctgc aactctctca gggccaggcg     4680
gtgaagggca atcagctgtt gcccgtctca ctggtgaaaa gaaaaaccac cctggcgccc     4740
aatacgcaaa ccgcctctcc ccgcgcgttg gccgattcat taatgcagct ggcacgacag     4800
gtttcccgac tggaaagcgg gcagtgagcg caacgcaatt aatgtgagtt agctcactca     4860
ttaggcaccc caggctttac actttatgct tccggctcgt atgttgtgtg gaattgtgag     4920
cggataacaa tttcacacag gaaacagcta tgaccatgat tacggattca ctggccgtcg     4980
ttttacaacg tcgtgactgg gaaaaccctg gcgttaccca acttaatcgc cttgcagcac     5040
atcccccttt cgccagctgg cgtaatagcg aagaggcccg caccgatcgc ccttcccaac     5100
agttgcgcag cctgaatggc gaatggcgct ttgcctggtt tccggcacca gaagcggtgc     5160
cggaaagctg gctggagtgc gatcttcctg aggccgatac tgtcgtcgtc ccctcaaact     5220
ggcagatgca cggttacgat gcgcccatct acaccaacgt aacctatccc attacggtca     5280
atccgccgtt tgttcccacg gagaatccga cgggttgtta ctcgctcaca tttaatgttg     5340
atgaaagctg gctacaggaa ggccagacgc gaattatttt tgatggcgtt ggaatt         5396
```

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence:Mab166
    (M166) CDRH3 region with N-addition, D segment, Jh-CDR3
    and Jh-Fr4 regions

<400> SEQUENCE: 3

```
Asn Arg Gly Asp Ile Tyr Tyr Asp Phe Thr Tyr Ala Met Asp Tyr Trp
  1               5                   10                  15

Gly Gln Gly Thr Ser Val Thr Val Ser Ser
             20                  25
```

```
<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:JH6

<400> SEQUENCE: 4

Tyr Tyr Tyr Tyr Tyr Gly Met Asp Val Trp Gly Gln Gly Thr Thr Val
 1               5                  10                  15

Thr Val Ser Ser
         20

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:JH3

<400> SEQUENCE: 5

Ala Phe Asp Ile Trp Gly Gln Gly Thr Met Val Thr Val Ser Ser
 1               5                  10                  15

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence:BA130-1-1D
      Vh human variable region containing minimal essential
      binding specificity domain (MEBSD) in heavy chain CDR3 from murine
      anti-PcrV antibody M166 and complete human J-region (JH6)

<400> SEQUENCE: 6

Gln Val Gln Leu Val Glu Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Arg Gly Asp Ile Tyr Tyr Asp Phe Thr Tyr Gly Met Asp
            100                 105                 110

Val Trp Gly Gln Gly Thr Thr Val Thr Val Ser Ser
        115                 120

<210> SEQ ID NO 7
<211> LENGTH: 109
<212> TYPE: PRT
<213> ORGANISM: Artificial Sequence
<220> FEATURE:
<223> OTHER INFORMATION: Description of Artificial Sequence:BA130-1-1D
      Vk human variable region containing minimal essential
      binding specificity domain (MEBSD) in heavy chain CDR3 from murine
      anti-PcrV antibody M166 and complete human J-region (JH6)

<400> SEQUENCE: 7
```

```
Ala Leu Asp Ile Gln Met Thr Gln Ser Pro Ser Ser Leu Ser Ala Ser
 1               5                  10                  15

Val Gly Asp Arg Val Thr Ile Thr Cys Arg Ala Ser Gln Ser Ile Ser
            20                  25                  30

Thr Tyr Leu Asn Trp Tyr Gln Gln Arg Pro Gly Lys Ala Pro Lys Leu
        35                  40                  45

Leu Ile Tyr Ala Ala Ser Arg Leu Leu Asn Gly Val Pro Ser Arg Phe
        50                  55                  60

Ser Gly Ser Gly Ser Gly Thr Asp Phe Thr Leu Thr Ile Ser Gly Leu
65                  70                  75                  80

Gln Pro Glu Asp Ile Ala Thr Tyr Tyr Cys Gln His Phe Trp Ser Thr
                85                  90                  95

Pro Tyr Thr Phe Gly Gln Gly Thr Lys Leu Glu Ile Lys
            100                 105
```

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence:BA130-5-E10
Vh human variable region containing minimal essential binding
specificity domain (MEBSD) in heavy chain CDR3 from murine
anti-PcrV antibody M166 and complete human J-region (JH6)

<400> SEQUENCE: 8

```
Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
        50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Arg Gly Asp Ile Tyr Tyr Asp Phe Thr Tyr Gly Met Asp
            100                 105                 110

Val Trp Gly Gln Gly Thr Thr Val Thr Val Ser Ser
        115                 120
```

<210> SEQ ID NO 9
<211> LENGTH: 109
<212> TYPE: PRT
<213> ORGANISM: Artificial Sequence
<220> FEATURE:
<223> OTHER INFORMATION: Description of Artificial Sequence:BA130-5-E10
Vk human variable region containing minimal essential binding
specificity domain (MEBSD) in heavy chain CDR3 from murine
anti-PcrV antibody M166 and complete human J-region (JH6)

<400> SEQUENCE: 9

```
Ala Leu Asp Ile Gln Met Thr Gln Ser Pro Ser Ser Leu Ser Ala Ser
 1               5                  10                  15

Val Gly Asp Arg Val Thr Ile Thr Cys Arg Ala Ser Gln Ser Ile Ser
            20                  25                  30

Thr Tyr Leu Asn Trp Tyr Gln Gln Arg Pro Gly Lys Ala Pro Lys Leu
        35                  40                  45
```

```
Leu Ile Tyr Ala Ala Ser Arg Leu Leu Asn Gly Val Pro Ser Arg Phe
    50                  55                  60

Ser Gly Ser Gly Ser Gly Thr Asp Phe Thr Leu Thr Ile Ser Gly Leu
65                  70                  75                  80

Gln Pro Glu Asp Ile Ala Thr Tyr Tyr Cys Gln His Phe Trp Ser Thr
                85                  90                  95

Pro Tyr Thr Phe Gly Gln Gly Thr Lys Leu Glu Ile Lys
            100                 105

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence:BA133-5-E6
      Vh human variable region containing minimal essential binding
      specificity domain (MEBSD) in heavy chain CDR3 from murine
      anti-PcrV antibody M166 and complete human J-region (JH3)

<400> SEQUENCE: 10

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Ile Thr Thr Asp Thr Ala Thr Arg Thr Thr Tyr
65                  70                  75                  80

Met Asp Leu Arg Ser Leu Arg Ser Asp Asp Thr Ala Val Tyr Tyr Cys
                85                  90                  95

Ala Arg Asn Arg Gly Asp Ile Tyr Tyr Asp Phe Thr Tyr Ala Phe Asp
                100                 105                 110

Ile Trp Gly Gln Gly Thr Met Val Thr Val Ser Ser
            115                 120

<210> SEQ ID NO 11
<211> LENGTH: 109
<212> TYPE: PRT
<213> ORGANISM: Artificial Sequence
<220> FEATURE:
<223> OTHER INFORMATION: Description of Artificial Sequence:BA133-5-E6
      Vk human variable region containing minimal essential binding
      specificity domain (MEBSD) in heavy chain CDR3 from murine
      anti-PcrV antibody M166 and complete human J-region (JH3)

<400> SEQUENCE: 11

Ala Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
                20                  25                  30

Thr Tyr Leu Asn Trp Tyr Gln Gln Arg Pro Gly Lys Ala Pro Lys Leu
            35                  40                  45

Leu Ile Tyr Ala Ala Ser Arg Leu Leu Asn Gly Val Pro Ser Arg Phe
    50                  55                  60

Ser Gly Ser Gly Ser Gly Thr Asp Phe Thr Leu Thr Ile Ser Gly Leu
65                  70                  75                  80

Gln Pro Glu Asp Ile Ala Thr Tyr Tyr Cys Gln His Phe Trp Ser Thr
                85                  90                  95
```

```
Pro Tyr Thr Phe Gly Gln Gly Thr Lys Leu Glu Ile Lys
            100                 105

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence:BA133-6-F5
      Vh human variable region containing minimal essential binding
      specificity domain (MEBSD) in heavy chain CDR3 from murine
      anti-PcrV antibody M166 and complete human J-region (JH3)

<400> SEQUENCE: 12

Gln Val Gln Leu Val Glu Ser Gly Pro Glu Val Lys Pro Gly Thr
 1               5                  10                  15

Ser Val Lys Val Ser Cys Lys Ala Ser Gly Phe Thr Phe Thr Ser Ser
                20                  25                  30

Ala Met Gln Trp Val Arg Gln Ala Arg Gly Gln Arg Leu Glu Trp Ile
            35                  40                  45

Gly Trp Ile Ile Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ala Glu Asp Thr Ala Val Tyr Tyr Cys
                85                  90                  95

Ala Arg Asn Arg Gly Asp Ile Tyr Tyr Asp Phe Thr Tyr Ala Phe Asp
            100                 105                 110

Ile Trp Gly Gln Gly Thr Met Val Thr Val Ser Ser
        115                 120

<210> SEQ ID NO 13
<211> LENGTH: 109
<212> TYPE: PRT
<213> ORGANISM: Artificial Sequence
<220> FEATURE:
<223> OTHER INFORMATION: Description of Artificial Sequence:BA133-6-F5
      Vk human variable region containing minimal essential binding
      specificity domain (MEBSD) in heavy chain CDR3 from murine
      anti-PcrV antibody M166 and complete human J-region (JH3)

<400> SEQUENCE: 13

Ala Leu Asp Ile Gln Met Thr Gln Ser Pro Ser Ser Leu Ser Ala Ser
 1               5                  10                  15

Val Gly Asp Arg Val Thr Ile Thr Cys Arg Ala Ser Gln Ser Ile Ser
                20                  25                  30

Thr Tyr Leu Asn Trp Tyr Gln Gln Arg Pro Gly Lys Ala Pro Lys Leu
            35                  40                  45

Leu Ile Tyr Ala Ala Ser Arg Leu Leu Asn Gly Val Pro Ser Arg Phe
    50                  55                  60

Ser Gly Ser Gly Ser Gly Thr Asp Phe Thr Leu Thr Ile Ser Gly Leu
65                  70                  75                  80

Gln Pro Glu Asp Ile Ala Thr Tyr Tyr Cys Gln His Phe Trp Ser Thr
                85                  90                  95

Pro Tyr Thr Phe Gly Gln Gly Thr Lys Leu Glu Ile Lys
            100                 105

<210> SEQ ID NO 14
<211> LENGTH: 124
<212> TYPE: PRT
<213> ORGANISM: Artificial Sequence
<220> FEATURE:
```

```
<223> OTHER INFORMATION: Description of Artificial Sequence:V-region of
      anti-PcrV antibody F6 VH

<400> SEQUENCE: 14

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Tyr Trp Gly Gln Gly Thr Ser Val Thr Val Ser Ser
        115                 120

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence:V-region of
      anti-PcrV antibody F6 VL

<400> SEQUENCE: 15

Glu Ile Val Leu Thr Gln Ser Pro Gly Thr Leu Ser Leu Ser Pro Gly
 1               5                  10                  15

Glu Arg Ala Thr Leu Ser Cys Thr Ala Ser Gln Ala Leu Ile Ser Ser
             20                  25                  30

Thr Leu Ala Trp Tyr Gln Gln Lys Pro Gly Gln Ala Pro Arg Leu Leu
         35                  40                  45

Ile Phe Gly Ala Ser Ser Arg Ala Thr Gly Thr Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Phe Trp Ser Thr Pro
                 85                  90                  95

Tyr Thr Phe Gly Gly Gly Thr Lys Leu Glu Ile Lys
            100                 105

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence:V-region of
      anti-PcrV antibody 1F1 VH

<400> SEQUENCE: 16

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Pro Met His Trp Val Arg Gln Ala Pro Gly Lys Gly Leu Glu Trp Val
         35                  40                  45
```

```
Ala Val Ile Ser Tyr Asp Gly Ser Glu Lys Trp Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Glu Met Asn Ser Leu Arg Pro Glu Asp Thr Ala Val Tyr Tyr Cys
                85                  90                  95
Ala Arg Asn Arg Gly Asp Ile Tyr Tyr Asp Phe Thr Tyr Ala Met Asp
            100                 105                 110
Tyr Trp Gly Gln Gly Thr Ser Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence:V-region of
      anti-PcrV antibody 1F1 VL

<400> SEQUENCE: 17

Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Val Ser Ser Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
     50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln His Phe Trp Ser Thr Pro Tyr
                85                  90                  95
Thr Phe Gly Gly Gly Thr Lys Leu Glu Ile Lys
            100                 105

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:heavy chain
      Kabat residues 89-94

<400> SEQUENCE: 18

Val Tyr Tyr Cys Ala Arg
  1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:light chain
      Kabat residues 85-88

<400> SEQUENCE: 19

Val Tyr Tyr Cys
  1

<210> SEQ ID NO 20
<211> LENGTH: 21
<212> TYPE: PRT
```

```
<213> ORGANISM: Artificial Sequence
<220> FEATURE:
<223> OTHER INFORMATION: Description of Artificial Sequence:non-natural
      synthetic secretion signal peptide designated SP2

<400> SEQUENCE: 20

Met Gly Lys Lys Gln Leu Val Val Phe Ala Leu Leu Leu Ala Phe Leu
 1               5                  10                  15

Ser Pro Ala Met Ala
            20

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 21

His His His His His His
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:
      anti-DYKDDDDK epitope tag

<400> SEQUENCE: 22

Asp Tyr Lys Asp Asp Asp Asp Lys
 1               5

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:1st Primer
      Set oligonucleotide primer for cloning Vkappa region
<220> FEATURE:
<221> NAME/KEY: modified_base
<222> LOCATION: (1)
<223> OTHER INFORMATION: n = 5' phosphorylated g

<400> SEQUENCE: 23
naagacagat ggtgcagcca cag                                        23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:1st Primer
      Set oligonucleotide primer for cloning Vlambda region
<220> FEATURE:
<221> NAME/KEY: modified_base
<222> LOCATION: (1)
<223> OTHER INFORMATION: n = 5' phosphorylated a

<400> SEQUENCE: 24
ngaggasggy gggaacagag tgac                                       24

<210> SEQ ID NO 25
<211> LENGTH: 21
<212> TYPE: DNA
<213> ORGANISM: Artificial Sequence
```

```
<220> FEATURE:
<223> OTHER INFORMATION: Description of Artificial Sequence:1st Primer
      Set oligonucleotide primer for cloning Vheavy (Vh) IgG
      region
<220> FEATURE:
<221> NAME/KEY: modified_base
<222> LOCATION: (1)
<223> OTHER INFORMATION: n = 5' phosphorylated g

<400> SEQUENCE: 25
nacsgatggg cccttggtgg a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:1st Primer
      Set oligonucleotide primer for cloning Vheavy (Vh) IgM
      region
<220> FEATURE:
<221> NAME/KEY: modified_base
<222> LOCATION: (1)
<223> OTHER INFORMATION: n = 5' phosphorylated a

<400> SEQUENCE: 26
nagggttggg gcggatgcac t                                              21

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaI region

<400> SEQUENCE: 27
catgtgtaat acgactcact atagggagtc atacatcacc atgggcgcgc tggacatcca    60
gwtgacccag tctcc                                                     75

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaII region

<400> SEQUENCE: 28
catgtgtaat acgactcact atagggagtc atacatcacc atgggcgcgc tggatgttgt    60
gatgactcag tctcc                                                     75

<210> SEQ ID NO 29
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaIII
      region

<400> SEQUENCE: 29
catgtgtaat acgactcact atagggagtc atacatcacc atgggcgcgc tggaaattgt    60
gwtgacrcag tctcc                                                     75

<210> SEQ ID NO 30
<211> LENGTH: 75
```

```
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaIV region

<400> SEQUENCE: 30
catgtgtaat acgactcact atagggagtc atacatcacc atgggcgcgc tggatattgt      60
gatgacccac actcc                                                       75

<210> SEQ ID NO 31
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaV region

<400> SEQUENCE: 31
catgtgtaat acgactcact atagggagtc atacatcacc atgggcgcgc tggaaacgac      60
actcacgcag tctcc                                                       75

<210> SEQ ID NO 32
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning VkappaVI region

<400> SEQUENCE: 32
catgtgtaat acgactcact atagggagtc atacatcacc atgggcgcgc tggaaattgt      60
gctgactcag tctcc                                                       75

<210> SEQ ID NO 33
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda1a
      region

<400> SEQUENCE: 33
catgtgtaat acgactcact atagggagtc atacatcacc atgggcgcgc tgcagtctgt      60
gctgactcag ccacc                                                       75

<210> SEQ ID NO 34
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda1b
      region

<400> SEQUENCE: 34
catgtgtaat acgactcact atagggagtc atacatcacc atgggcgcgc tgcagtctgt      60
gytgacgcag ccgcc                                                       75

<210> SEQ ID NO 35
<211> LENGTH: 75
<212> TYPE: DNA
<213> ORGANISM: Artificial Sequence
<220> FEATURE:
```

<223> OTHER INFORMATION: Description of Artificial Sequence:2nd Primer
      Set oligonucleotide primer for cloning Vlambda1c
      region

<400> SEQUENCE: 35
catgtgtaat acgactcact atagggagtc atacatcacc atgggcgcgc tgcagtctgt    60
cgtgacgcag ccgcc                                                    75

<210> SEQ ID NO 36
<211> LENGTH: 73
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda2 region

<400> SEQUENCE: 36
catgtgtaat acgactcact atagggagtc atacatcacc atgggcgcgc tgcartctgc    60
cctgactcag cct                                                      73

<210> SEQ ID NO 37
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda3a
      region

<400> SEQUENCE: 37
catgtgtaat acgactcact atagggagtc atacatcacc atgggcgcgc tgtcctatgw    60
gctgactcag ccacc                                                    75

<210> SEQ ID NO 38
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda3b
      region

<400> SEQUENCE: 38
catgtgtaat acgactcact atagggagtc atacatcacc atgggcgcgc tgtcttctga    60
gctgactcag gaccc                                                    75

<210> SEQ ID NO 39
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda4 region

<400> SEQUENCE: 39
catgtgtaat acgactcact atagggagtc atacatcacc atgggcgcgc tgcacgttat    60
actgactcaa ccgcc                                                    75

<210> SEQ ID NO 40
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda5 region -continued

```
<400> SEQUENCE: 40
catgtgtaat acgactcact atagggagtc atacatcacc atgggcgcgc tgcaggctgt        60
gctgactcag ccgtc                                                         75

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda6 region

<400> SEQUENCE: 41
catgtgtaat acgactcact atagggagtc atacatcacc atgggcgcgc tgaattttat        60
gctgactcag cccca                                                         75

<210> SEQ ID NO 42
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda7 and
      Vlambda8 region

<400> SEQUENCE: 42
catgtgtaat acgactcact atagggagtc atacatcacc atgggcgcgc tgcagrctgt        60
ggtgacycag gagcc                                                         75

<210> SEQ ID NO 43
<211> LENGTH: 75
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vlambda9 region

<400> SEQUENCE: 43
catgtgtaat acgactcact atagggagtc atacatcacc atgggcgcgc tgcwgcctgt        60
gctgactcag ccmcc                                                         75

<210> SEQ ID NO 44
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh1b and Vh7
      region

<400> SEQUENCE: 44
catgtgtaat acgactcact atagggagtc atacatcagg cccagccggc catggctcag        60
rtgcagctgg tgcartctgg                                                    80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh1c region

<400> SEQUENCE: 45
```

```
catgtgtaat acgactcact atagggagtc atacatcagg cccagccggc catggctsag     60
gtccagctgg trcagtctgg                                                 80
```

<210> SEQ ID NO 46
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh2 region

<400> SEQUENCE: 46

```
catgtgtaat acgactcact atagggagtc atacatcagg cccagccggc catggctcag     60
rtcaccttga aggagtctgg                                                 80
```

<210> SEQ ID NO 47
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh3b region

<400> SEQUENCE: 47

```
catgtgtaat acgactcact atagggagtc atacatcagg cccagccggc catggctsag     60
gtgcagctgg tggagtctgg                                                 80
```

<210> SEQ ID NO 48
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh3c region

<400> SEQUENCE: 48

```
catgtgtaat acgactcact atagggagtc atacatcagg cccagccggc catggctgag     60
gtgcagctgg tggagwcygg                                                 80
```

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh4b region

<400> SEQUENCE: 49

```
catgtgtaat acgactcact atagggagtc atacatcagg cccagccggc catggctcag     60
gtgcagctac agcagtgggg                                                 80
```

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh4c region

<400> SEQUENCE: 50

```
catgtgtaat acgactcact atagggagtc atacatcagg cccagccggc catggctcag     60
stgcagctgc aggagtcsgg                                                 80
```

```
<210> SEQ ID NO 51
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh5 region

<400> SEQUENCE: 51
catgtgtaat acgactcact atagggagtc atacatcagg cccagccggc catggctgar      60
gtgcagctgg tgcagtctgg                                                   80

<210> SEQ ID NO 52
<211> LENGTH: 80
<212> TYPE: DNA
<213> ORGANISM: Artificial Sequence
<220> FEATURE:
<223> OTHER INFORMATION: Description of Artificial Sequence:2nd Primer
      Set oligonucleotide primer for cloning Vh6 region

<400> SEQUENCE: 52
catgtgtaat acgactcact atagggagtc atacatcagg cccagccggc catggctcag      60
gtacagctgc agcagtcagg                                                   80

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jkappa1,
      Jkappa2 and Jkappa4 region

<400> SEQUENCE: 53
tatagcggcc gcactagttc gtttgatrtc cascttggtc c                           41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jkappa3 region

<400> SEQUENCE: 54
tatagcggcc gcagtagttc gtttgatatc cactttggtc c                           41

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jkappa5 region

<400> SEQUENCE: 55
tatagcggcc gcactagttc gtttaatctc cagtcgtgtc c                           41

<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jlambda1 region

<400> SEQUENCE: 56
```

```
tatagcggcc gccctaggct gccyaaggac ggtgaccttg gtcc                44
```

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jlambda2 and
      Jlambda3 region

<400> SEQUENCE: 57

```
tatagcggcc gccctaggct gccyaaggac ggtcagcttg gtcc                44
```

<210> SEQ ID NO 58
<211> LENGTH: 44
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning Jlambda7 region

<400> SEQUENCE: 58

```
tatagcggcc gccctaggct gccygaggac ggtcagctgg gtgc                44
```

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning JH1 and JH2
      region

<400> SEQUENCE: 59

```
gcggatgcac ttccggagga gacggtgacc agggtgcc                       38
```

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning JH3 region

<400> SEQUENCE: 60

```
gcggatgcac ttccggaaga gacggtgacc attgtccc                       38
```

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning JH4 and JH5
      region

<400> SEQUENCE: 61

```
gcggatgcac ttccggagga gacggtgacc agggttcc                       38
```

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence:3rd Primer
      Set oligonucleotide primer for cloning JH6 region

<400> SEQUENCE: 62
gcggatgcac ttccggagga gacggtgacc gtggtccc    38

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence:antisense
      primer to Vh Kabat positions 86-89

<400> SEQUENCE: 63
cacagtagta tacggccgtg tc    22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence:antisense
      primer to Vh Kabat positions 86-89
<220> FEATURE:
<221> NAME/KEY: modified_base
<222> LOCATION: (17)
<223> OTHER INFORMATION: n = g, a, c or t

<400> SEQUENCE: 64
cacagtagta tacrgcngtg tc    22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence:antisense
      primer to Vh Kabat positions 86-89

<400> SEQUENCE: 65
cacagtagta tacggccgtc tc    22

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence:antisense
      primer to Vkappa Kabat positions 80-84

<400> SEQUENCE: 66
caaatgtata ctgcmamatc ttcag    25

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:antisense
      primer to Vkappa Kabat positions 80-84

<400> SEQUENCE: 67
ttcaaatgta tactgcaata tcttcag    27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence:antisense
      primer to Vkappa Kabat positions 80-84

<400> SEQUENCE: 68
ttcaaatgta tacyccraca tcctcag    27

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence:antisense
      primer to Vkappa Kabat positions 80-84

<400> SEQUENCE: 69
ttcaaatgta tactgcagca tcttcag    27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence:antisense
      primer to Vlambda Kabat positions 81-85
<220> FEATURE:
<221> NAME/KEY: modified_base
<222> LOCATION: (26)
<223> OTHER INFORMATION: n = g, a, c or t

<400> SEQUENCE: 70
ttgtaaagat atcrgcytcr tcyhync    27

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence:antisense
      primer to Vlambda Kabat positions 81-85

<400> SEQUENCE: 71
gtaaagatat crgcctcrtc btyhg    25

<210> SEQ ID NO 72
<211> LENGTH: 99
<212> TYPE: DNA
<213> ORGANISM: Artificial Sequence
<220> FEATURE:
<223> OTHER INFORMATION: Description of Artificial Sequence:M166 Vh
      CDR3-FR4 including 5' Bst1107 I site and 3' BspE I
      site

<400> SEQUENCE: 72
gtatactact gtgccagaaa tagaggggat atttactatg atttcactta tgccatggac    60
tactggggtc aaggaaccct agtcaccgtc tcctccgga    99

<210> SEQ ID NO 73
<211> LENGTH: 78
<212> TYPE: DNA
<213> ORGANISM: Artificial Sequence
<220> FEATURE:
<223> OTHER INFORMATION: Description of Artificial Sequence:M166 Vkappa
      CDR3-FR4 including 5' Bst1107 I site and 3' Spe I
      site

<400> SEQUENCE: 73
gtatactact gtcaacattt ttggagtact ccgtacacgt tcggaggggg gaccaagctg    60
gaaataaaac gaactagt    78

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence:highly
      conserved human FR3 sequence (Kabat positions
      90-94)

<400> SEQUENCE: 74

Tyr Tyr Cys Ala Arg
 1               5

<210> SEQ ID NO 75
<211> LENGTH: 100
<212> TYPE: DNA
<213> ORGANISM: Artificial Sequence
<220> FEATURE:
<223> OTHER INFORMATION: Description of Artificial Sequence:M166 Vh
      CDR3-FR4 antisense oligonucleotide including 5'
      BspE I site and 3' nucleotides encoding highly
      conserved human FR3 YYCAR sequence

<400> SEQUENCE: 75
tagatccgga ggagacggtg actgaggttc cttgacccca gtagtccatg gcataagtga      60
aatcatagta aatatcccct ctatttctgg cacagtaata                           100

<210> SEQ ID NO 76
<211> LENGTH: 83
<212> TYPE: DNA
<213> ORGANISM: Artificial Sequence
<220> FEATURE:
<223> OTHER INFORMATION: Description of Artificial Sequence:M166 Vkappa
      CDR3-FR4 antisense oligonucleotide including 5'
      Spe I site and 3' nucleotides encoding highly
      conserved human FR3 YYC sequence

<400> SEQUENCE: 76
cgaattgaac tagttcgttt tatttccagc ttggtccccc ctccgaacgt gtacggagta      60
ctccaaaaat gttgrcarta rta                                              83

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence:PCR
      amplification VkappaI Sense Primer

<400> SEQUENCE: 77
cagccggcca tggccgcgct ggacatccag wtgacccagt ctcc                       44

<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequence:PCR
      amplification VkappaII Sense Primer

<400> SEQUENCE: 78
cagccggcca tggccgcgct ggatgttgtg atgactcagt ctcc                       44

<210> SEQ ID NO 79
<211> LENGTH: 44
<212> TYPE: DNA
<213> ORGANISM: Artificial Sequence

```
<220> FEATURE:
<223> OTHER INFORMATION: Description of Artificial Sequence:PCR
      amplification VkappaIII Sense Primer

<400> SEQUENCE: 79
cagccggcca tggccgcgct ggaaattgtg wtgacrcagt ctcc                    44

<210> SEQ ID NO 80
<211> LENGTH: 44
<212> TYPE: DNA
<213> ORGANISM: Artificial Sequence
<220> FEATURE:
<223> OTHER INFORMATION: Description of Artificial Sequence:PCR
      amplification VkappaIV Sense Primer

<400> SEQUENCE: 80
cagccggcca tggccgcgct ggatattgtg atgacccagt ctcc                    44

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequence:PCR
      amplification VkappaV Sense Primer

<400> SEQUENCE: 81
cagccggcca tggccgcgct ggaaacgaca ctcacgcagt ctcc                    44

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence:PCR
      amplification VkappaVI Sense Primer

<400> SEQUENCE: 82
cagccggcca tggccgcgct ggaaattgtg ctgactcagt ctcc                    44

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda1a Sense Primer

<400> SEQUENCE: 83
catgtatcag cgcgctgcag tctgtgctga ctcagccacc                         40

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda1b Sense Primer

<400> SEQUENCE: 84
catgtatcag cgcgctgcag tctgtgytga cgcagccgcc                         40

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence:PCR
``` amplification Vlambda1c Sense Primer

<400> SEQUENCE: 85
catgtatcag cgcgctgcag tctgtcgtga cgcagccgcc        40

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence:PCR
      amplification Vlambda2 Sense Primer

<400> SEQUENCE: 86
catgtatcag cgcgctgcar tctgccctga ctcagcct        38

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda3a Sense Primer

<400> SEQUENCE: 87
catgtatcag cgcgctgtcc tatgwgctga ctcagccacc        40

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda3b Sense Primer

<400> SEQUENCE: 88
catgtatcag cgcgctgtct tctgagctga ctcaggaccc        40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda4 Sense Primer

<400> SEQUENCE: 89
catgtatcag cgcgctgcac gttatactga ctcaaccgcc        40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda5 Sense Primer

<400> SEQUENCE: 90
catgtatcag cgcgctgcag gctgtgctga ctcagccgtc        40

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda6 Sense Primer

```
<400> SEQUENCE: 91
catgtatcag cgcgctgaat tttatgctga ctcagcccca                           40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda7 and Vlambda8 Sense Primer

<400> SEQUENCE: 92
catgtatcag cgcgctgcag rctgtggtga cycaggagcc                           40

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda9 Sense Primer

<400> SEQUENCE: 93
catgtatcag cgcgctgcwg cctgtgctga ctcagccmcc                           40

<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda10 Sense Primer

<400> SEQUENCE: 94
catgtatcag cgcgctgcag gcagggctga ctcagccacc                           40

<210> SEQ ID NO 95
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh1b and Vh7 Sense Primer

<400> SEQUENCE: 95
gcccagccgg ccatggctca grtgcagctg gtgcartctg g                         41

<210> SEQ ID NO 96
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh1c Sense Primer

<400> SEQUENCE: 96
gcccagccgg ccatggctsa ggtccagctg gtrcagtctg g                         41

<210> SEQ ID NO 97
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh2 Sense Primer

<400> SEQUENCE: 97
```
gcccagccgg ccatggctca grtcaccttg aaggagtctg g        41

<210> SEQ ID NO 98
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh3b Sense Primer

<400> SEQUENCE: 98
gcccagccgg ccatggctsa ggtgcagctg gtggagtctg g        41

<210> SEQ ID NO 99
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh3c Sense Primer

<400> SEQUENCE: 99
gcccagccgg ccatggctga ggtgcagctg gtggagwcyg g        41

<210> SEQ ID NO 100
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh4b Sense Primer

<400> SEQUENCE: 100
gcccagccgg ccatggctca ggtgcagcta cagcagtggg g        41

<210> SEQ ID NO 101
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh4c Sense Primer

<400> SEQUENCE: 101
gcccagccgg ccatggctca gstgcagctg caggagtcsg g        41

<210> SEQ ID NO 102
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh5 Sense Primer

<400> SEQUENCE: 102
gcccagccgg ccatggctga rgtgcagctg gtgcagtctg g        41

<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence:PCR
      amplification Vh6 Sense Primer

<400> SEQUENCE: 103
gcccagccgg ccatggctca ggtacagctg cagcagtcag g        41

<210> SEQ ID NO 104
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaI Antisense Primer

<400> SEQUENCE: 104
cagataatgt cgactggcag tagtaagttg caaaatcttc ag         42

<210> SEQ ID NO 105
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaI Antisense Primer

<400> SEQUENCE: 105
cagataatgt cgactggcag tagtatgttg caayatcttc ag         42

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaII Antisense Primer

<400> SEQUENCE: 106
cagataatgt cgactggcag tagtaaacyc cracatcctc ag         42

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaIII Antisense Primer

<400> SEQUENCE: 107
cagataatgt cgactggcag tagtamactg caaaatcttc ag         42

<210> SEQ ID NO 108
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaIV Antisense Primer

<400> SEQUENCE: 108
cagataatgt cgactggcag tagtaaacag ccacatcttc ag         42

<210> SEQ ID NO 109
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaV Antisense Primer

<400> SEQUENCE: 109
cagataatgt cgactggcag aagtagtatg cagcatcctc ag         42

<210> SEQ ID NO 110

```
<211> LENGTH: 42
<212> TYPE: DNA
<213> ORGANISM: Artificial Sequence
<220> FEATURE:
<223> OTHER INFORMATION: Description of Artificial Sequence:PCR
      amplification VkappaVI Antisense Primer

<400> SEQUENCE: 110
cagataatgt cgactggcag tagtaygttg cagcatcttc ag                           42

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda1, Vlambda2, Vlambda3,
      Vlambda4, Vlambda5, Vlambda6, Vlambda7 and
      Vlambda10 Antisense Primer

<400> SEQUENCE: 111
cagataatgt cgactggcag tagtartcrg cctcrtcctc                              40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda1and Vlambda3 Antisense
      Primer

<400> SEQUENCE: 112
cagataatgt cgactggcag tagtagtcrg cctcrtcycc                              40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda4c Antisense Primer

<400> SEQUENCE: 113
cagataatgt cgactggcag tggtactcag cctcatcgtc                              40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda8 Antisense Primer

<400> SEQUENCE: 114
cagataatgt cgactggcag tagtaatcag attcatcatc                              40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence:PCR
      amplification Vlambda9 Antisense Primer

<400> SEQUENCE: 115
cagataatgt cgactggcag tggtagtcac tctcatcctc                              40
```

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence:PCR
      amplification Vh1, Vh3, Vh4 and Vh6 Sense Primer

<400> SEQUENCE: 116
cagataatgt cgacgtgcgc agtagtacac rgcygtgtc                39

<210> SEQ ID NO 117
<211> LENGTH: 39
<212> TYPE: DNA
<213> ORGANISM: Artificial Sequence
<220> FEATURE:
<223> OTHER INFORMATION: Description of Artificial Sequence:PCR
      amplification Vh2 Sense Primer

<400> SEQUENCE: 117
cagataatgt cgacgtgcgc agtagtaygt ggctgtgtc                39

<210> SEQ ID NO 118
<211> LENGTH: 39
<212> TYPE: DNA
<213> ORGANISM: Artificial Sequence
<220> FEATURE:
<223> OTHER INFORMATION: Description of Artificial Sequence:PCR
      amplification Vh5 Sense Primer

<400> SEQUENCE: 118
cagataatgt cgacgtgcgc agtagtacat ggcggtgtc                39

<210> SEQ ID NO 119
<211> LENGTH: 39
<212> TYPE: DNA
<213> ORGANISM: Artificial Sequence
<220> FEATURE:
<223> OTHER INFORMATION: Description of Artificial Sequence:PCR
      amplification Vh7 Sense Primer

<400> SEQUENCE: 119
cagataatgt cgacgtgcgc agtagtacac ggcagtgtc                39

<210> SEQ ID NO 120
<211> LENGTH: 100
<212> TYPE: DNA
<213> ORGANISM: Artificial Sequence
<220> FEATURE:
<223> OTHER INFORMATION: Description of Artificial Sequence:M166 Vh
      CDR3-Human FR4 antisense oligonucleotide including
      5' BspE I site and 3' nucleotides complementary to
      the V segment YYCAR region

<400> SEQUENCE: 120
ctgttccgga gctgacggtg actgtggttc cttgacccca gtaatccatc gcataggtga    60
aatcatagta aatatcacca cggttacgtg cgcagtagta                        100

<210> SEQ ID NO 121
<211> LENGTH: 80
<212> TYPE: DNA
<213> ORGANISM: Artificial Sequence
<220> FEATURE:
<223> OTHER INFORMATION: Description of Artificial Sequence:M166 Vkappa
      CDR3-Human FR4 antisense oligonucleotide including
      5' Spe I site and 3' nucleotides complementary to
      V segment YYC region

<400> SEQUENCE: 121

```
attgaactag ttcgtttat ttccagcttg gtccctgtc cgaacgtgta cggagtactc    60
caaaaatgct ggcagtagta                                              80
```

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence:hinge region
      of IgG1

<400> SEQUENCE: 122

Thr His Thr Cys Pro Pro Cys Pro Ala
 1               5

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence:Myc tag
      peptide

<400> SEQUENCE: 123

Gly Ala Ala Glu Gln Lys Leu Ile Ser Glu Glu Asp Leu Asn
 1               5                  10

<210> SEQ ID NO 124
<211> LENGTH: 64
<212> TYPE: DNA
<213> ORGANISM: Artificial Sequence
<220> FEATURE:
<223> OTHER INFORMATION: Description of Artificial Sequence:Antisense
      Primer JH6

<400> SEQUENCE: 124

```
ctgttccgga gctgacggtg actgtggttc cttgacccca gacatccatg ccataggtga    60
aatc                                                                 64
```

<210> SEQ ID NO 125
<211> LENGTH: 64
<212> TYPE: DNA
<213> ORGANISM: Artificial Sequence
<220> FEATURE:
<223> OTHER INFORMATION: Description of Artificial Sequence:Antisense
      Primer JH3

<400> SEQUENCE: 125

```
ctgttccgga gctgacggtg accattgttc cttgacccca aatatcgaac gcataggtga    60
aatc                                                                 64
```

<210> SEQ ID NO 126
<211> LENGTH: 41
<212> TYPE: DNA
<213> ORGANISM: Artificial Sequence
<220> FEATURE:
<223> OTHER INFORMATION: Description of Artificial Sequence:Sense Primer
      Vh3b

<400> SEQUENCE: 126

```
gcccagccgg ccatggctsa ggtgcagctg gtggagtctg g                        41
```

<210> SEQ ID NO 127
<211> LENGTH: 59
<212> TYPE: DNA

```
<213> ORGANISM: Artificial Sequence
<220> FEATURE:
<223> OTHER INFORMATION: Description of Artificial Sequence:two-step
      nested PCR overlapped Primer 32 (pr32)

<400> SEQUENCE: 127
cagaaatcaa tttctgttcc atagaaccac cgccaccaca agatttgggc tcaactttc      59

<210> SEQ ID NO 128
<211> LENGTH: 55
<212> TYPE: DNA
<213> ORGANISM: Artificial Sequence
<220> FEATURE:
<223> OTHER INFORMATION: Description of Artificial Sequence:two-step
      nested PCR overlapped Primer 37 (pr37)

<400> SEQUENCE: 128
cttgttctta gctggttttg ctgccaagat atctgctgag gtgcagctgg tggag          55

<210> SEQ ID NO 129
<211> LENGTH: 60
<212> TYPE: DNA
<213> ORGANISM: Artificial Sequence
<220> FEATURE:
<223> OTHER INFORMATION: Description of Artificial Sequence:two-step
      nested PCR overlapped Primer 33 (pr33)

<400> SEQUENCE: 129
aaccccagat ctgtcgacca ccatgttgtt acaagccttc ttgttcttag ctggttttgc     60

<210> SEQ ID NO 130
<211> LENGTH: 59
<212> TYPE: DNA
<213> ORGANISM: Artificial Sequence
<220> FEATURE:
<223> OTHER INFORMATION: Description of Artificial Sequence:two-step
      nested PCR overlapped Primer 34 (pr34)

<400> SEQUENCE: 130
gatcttagct agccgcggtt agttcaaatc ctcttcagaa atcaatttct gttccatag      59

<210> SEQ ID NO 131
<211> LENGTH: 59
<212> TYPE: DNA
<213> ORGANISM: Artificial Sequence
<220> FEATURE:
<223> OTHER INFORMATION: Description of Artificial Sequence:nested PCR
      amplification Primer 66 (pr66)

<400> SEQUENCE: 131
cttattcctg gctggtttcg ctgctaagat ctctgctgac atccagttga cccagtctc      59

<210> SEQ ID NO 132
<211> LENGTH: 46
<212> TYPE: DNA
<213> ORGANISM: Artificial Sequence
<220> FEATURE:
<223> OTHER INFORMATION: Description of Artificial Sequence:nested PCR
      amplification Primer 67 (pr67)

<400> SEQUENCE: 132
cactagacat ggatccatat gctaacactc tcccctgttg aagctc                    46

<210> SEQ ID NO 133
<211> LENGTH: 57
<212> TYPE: DNA
<213> ORGANISM: Artificial Sequence
<220> FEATURE:
```

-continued

```
<223> OTHER INFORMATION: Description of Artificial Sequence:nested PCR
      amplification Primer 68 (pr68)

<400> SEQUENCE: 133
tgaaaattcg aattccacca tgttattgca agctttctta ttcctggctg gtttcgc        57
```

ANTIBODY SPECIFICITY TRANSFER USING MINIMAL ESSENTIAL BINDING DETERMINANTS

CROSS-REFERENCES TO RELATED APPLICATIONS

This application claims benefit of U.S. provisional application No. 60/537,364, filed Jan. 20, 2004 and U.S. provisional application No. 60/546,216, filed Feb. 23, 2004, each of which applications is herein incorporated by reference.

BACKGROUND OF THE INVENTION

Many molecular targets suitable for antibody-mediated disease therapy have been validated with the use of non-human antibody reagents, and this process will continue for many of the new therapeutic targets which are expected to emerge from the human genome in the coming years. As a target becomes validated for therapy, the antibodies, typically murine, used to validate the target become leads for the development of biologic drugs. However, for many therapeutic applications the efficacy and safety of non-human antibodies are compromised because of their immunogenicity in patients. Thus, before such antibodies can be approved for therapeutic use they must be replaced with human counterparts having equivalent bioactivity, or they must be "humanized" in some way to eliminate or minimize immunogenicity in humans.

Established methods for the isolation of antigen-specific human antibodies include the screening of hybridomas from mice that are transgenic for the human immunoglobulin loci (e.g., Jakobavits, 1998, *Adv Drug Deliv Rev.* 31:33-42), and in vitro methods in which recombinant libraries of human antibody fragments displayed on and encoded in filamentous bacteriophage (e.g., McCafferty et al., 1990, *Nature* 348:552-554), yeast cells (e.g., Boder and Wittrup, 1997, *Nat Biotechnol* 15:553-557), and ribosomes (e.g., Hanes and Pluckthun, 1997, *Proc Natl Acad Sci USA* 94:4937-4942) are panned against immobilized antigen. These methods have yielded many useful human antibodies. However, for many non-human antibodies with desirable therapeutic properties, human antibodies with equivalent bioactivities have not been isolated using these methods.

Mice transgenic for human immunoglobulin loci generally do not express the full complement of human diversity, and affinity maturation is less efficient. Thus, the success rates for desired affinities and specificities tend to be lower than with conventional mice. The principal limitations of the display technologies stem from biased expression of antibody repertoires, and the specificity and affinity limitations of naïve repertoires. Antigen-binding antibodies from naïve libraries typically require additional affinity maturation, which with current in vitro methods is an arduous and uncertain process and moreover, may introduce immunogenic epitopes into the antibody.

The most widely used methods for minimizing the immunogenicity of non-human antibodies while retaining as much of the original specificity and affinity as possible involve grafting the CDRs of the non-human antibody onto human frameworks typically selected for their structural homology to the non-human framework (Jones et al., 1986, *Nature* 321: 522-5; U.S. Pat. No. 5,225,539). Originally these methods resulted in drastic losses of affinity. However, it was then shown that some of the affinity could be recovered by restoring the non-human residues at key positions in the framework that are required to maintain the canonical structures of the non-human CDRs 1 and 2 (Bajorath et al., 1995, *J Biol Chem* 270:22081-4; Martin et al., 1991, *Methods Enzymol.* 203: 121-53; Al-Lazikani, 1997, *J Mol Biol* 273:927-48). Recovering the native conformations of CDR3s is a much more uncertain enterprise because their structures are more variable. Determining which non-human residues to restore to recover functional CDR3 conformation is thus largely a matter of modeling where possible combined with trial and error. As a result, in many cases the full affinity of the original non-human antibody is not recovered. Exemplary methods for humanization of antibodies by CDR grafting are disclosed, for example, in U.S. Pat. No. 6,180,370.

To mitigate the shortcomings of the traditional CDR-grafting approaches, various hybrid selection approaches have been tried, in which portions of the non-human antibody have been combined with libraries of complementary human antibody sequences in successive rounds of selection for antigen binding, in the course of which most of the non-human sequences are gradually replaced with human sequences. These approaches have generally not fared better than CDR-grafting, however. For example, in the chain-shuffling technique (Marks, et al., 1992, *Biotechnology* 10:779-83) one chain of the non-human antibody is combined with a naïve human repertoire of the other chain on the rationale that the affinity of the non-human chain will be sufficient to constrain the selection of a human partner to the same epitope on the antigen. Selected human partners are then used to guide selection of human counterparts for the remaining non-human chains.

Other methodologies include chain replacement techniques where the non-human CDR3s were retained and only the remainder of the V-regions, including the frameworks and CDRs 1 and 2, were individually replaced in steps performed sequentially (e.g., U.S. Patent Application No. 20030166871; Rader, et al., *Proc Natl Acad Sci USA* 95:8910-15, 1998; Steinberger, et al., *J. Biol. Chem.* 275:36073-36078, 2000; Rader, et al., *J. Biol. Chem.* 275:13668-13676, 2000). However, this strategy still has the drawback that selectable human V-regions must be compatible not just with the non-human CDR3 but with the non-human companion V-region as well. This inter-species compatibility imposes a high demand for structural homology in the selected human V-regions, such that those most homologous to the non-human V-regions are generally selected. In this regard, the result is quite similar to that of the CDR grafting approach, except that CDRs 1 and 2 are initially human in the selected V-regions.

Existing methods for the isolation of human antibodies with required bioactivities for therapeutic use, or for "humanizing" non-human antibodies for therapeutic use thus have many limitations, as noted above. Primarily, these limitations relate to the retention or inclusion of nonhuman sequences in order to maintain binding affinity. Thus, there is a need for efficient humanization methods that minimize nonhuman sequences and thereby minimize introduction of immunogenic epitopes. The current invention addresses this need.

BRIEF SUMMARY OF THE INVENTION

The invention provides methods of creating antibodies with the binding specificity of a reference antibody for a target antigen by transferring the minimal essential binding specificity determinants from the reference antibody. This can be accomplished by transferring the minimal essential binding specificity in the context of transferring a D segment, or a CDR3, or a CDR3-FR4, or any other CDR3-FR4 fragment that comprises the minimal essential binding specificity determinant. Antibodies created using these methods retain the binding specificity, and often affinity, of the reference antibody with minimal divergence from germline sequences. Accordingly, such antibodies, e.g., humanized antibodies, should be less immunogenic than those derived from prior art technologies.

In one aspect, the invention provides a method of making an antibody having a binding specificity of a reference antibody, the method comprising:

a) joining a heavy chain CDR3 binding specificity determinant (BSD) from the reference antibody to a diverse population of human VH segments thereby creating a library of human VH regions having the reference antibody heavy chain CDR3 BSD;

b) joining a light chain CDR3 BSD from the reference antibody to a diverse population of human VL segments, thereby creating a library of human VL regions having the reference antibody light chain CDR3 BSD;

c) combining the libraries of step a and step b to create an antibody library comprising members where a member has one VH comprising the reference antibody heavy chain CDR3 BSD and one VL comprising the reference antibody light chain CDR3 BSD; and d) isolating a member of the library of step c that binds the same antigen as the reference antibody. In one embodiment, the diverse population of human VH segments is human germline. The diverse population of human VL segments can also be human germline, or near human germline. Thus both the diverse population of VH segment and the diverse population of VL segments can be human germline. In some embodiments, e.g, embodiments, in which a selected antibody has a germline VH and/or VL segment, the method further comprises mutagenizing one or both CDR3s from an antibody selected in step (d) and selecting an antibody that has a higher affinity for the target antigen than antibody selected in step (d).

The diverse population of human VH segments and/or the diverse populations of human VL segments can also be from one V segment subclass.

In some embodiments, at least one of the CDR3 BSDs from the reference antibody is a CDR3-FR4 segment from the reference antibody.

An FR4 can be a human germline FR4. In some embodiments, the human FR4 is a library of diverse human FR4 sequences.

In some embodiments of the invention, the J segment is a human antibody J segment.

The BSD from the reference antibody can be a heavy or light chain CDR3 from the reference antibody. In some embodiments, the BSD for both the heavy and light chain is the CDR3 from the reference antibody.

The heavy chain BSD can also be the D segment from the reference antibody. In other embodiments, the heavy and/or light chain BSD can be the minimal essential binding specificity determinant from the reference antibody.

In some embodiments, the step of isolating a member of the library of step (c) comprises a screening step to identify a member of the library that binds to the antigen with the same or higher affinity than the reference antibody.

For the methods of the invention, a reference antibody can be any antibody, but is typically a non-human antibody.

The step of combining the libraries can comprise expressing the library of human VH regions and the library of human VL regions on a single expression vector using separate promoters, or using a single promoter to drive expression of the VH and VL regions. Alternatively, the step of combining the libraries can comprise expressing the library of human VH regions and the library of human VL regions using two expression vectors, one to express each library.

In the methods of the invention, the antibody library of step c) can comprise antibodies where an antibody is an IgG, an Fv, an Fab, an Fab', an F(ab')2, a single chain Fv, or an IgG with a deletion of one or more domains.

The step of isolating the members of the library can comprise various screening methodologies including using a colony lift binding assay or screening using display technology, such as bacteriophage display, yeast cell display, bacterial cell display, ribosome display, and mammalian cell display. In one embodiment, screening is performed by screening pools of library members.

In some embodiments, the method further comprises:

e) combining heavy chain V regions from a plurality of members selected in accordance with (d) with a library of human VL regions having the reference antibody light chain CDR3 BSD; and f) selecting a member that binds to the same antigen as the reference antibody.

In other embodiments, the method further comprises:

e) combining light chain V regions from a plurality of members selected in accordance with (d) with a library of human VH regions having the reference antibody heavy chain CDR3 BSD; and f) selecting a member that binds to the same antigen as the reference antibody.

The method can also comprise:

e) combining heavy chain V regions from a plurality of members selected in accordance with (d) with light chain V regions from a plurality of members selected in accordance with (d); and f) selecting a member that binds to the same antigen as the reference antibody.

The invention additionally provides a method of making an antibody having a binding specificity of a reference antibody, comprising:

a) joining a CDR3 BSD from the heavy chain of the reference antibody to a diverse population of human VH segments, thereby creating a population comprising diverse VH regions having a BSD from the reference antibody heavy chain CDR3;

b) combining the population of step a with a VL comprising a human germline subclass V segment joined to a light chain CDR3 BSD from the reference antibody to create an antibody library; and c) isolating a member of the library of step c that binds the same antigen the reference antibody. At least one of the CDR3 BSDs from the reference antibody can be a minimal essential binding specificity determinant, or a D segment from the reference antibody (for the heavy chain), or a CDR3. In some embodiments, the diverse population of human VH regions comprises germline VH segments. In other embodiments, the J segment region of the VL of step (b) can also be a human germline sequence.

The invention also provides a method of making an antibody having a binding specificity of a reference antibody, the method comprising:

a) joining a CDR3 BSD from the light chain of the reference antibody to a diverse population of human VL segments, thereby creating a population comprising diverse VL regions having a BSD from the reference antibody light chain CDR3;

b) combining the population of step a with a VH comprising a human germline subclass V segment joined to a CDR3 BSD from the reference antibody to create an antibody library; and c) isolating a member of the library of step c that binds the same antigen the reference antibody. The BSDs from the reference antibody can be a minimal essential binding specificity determinant, or a D segment (where the BSD is from the heavy chain), or a CDR3. In some embodiments, the diverse population of human VL regions can comprise germline VL segments. In additional embodiments, the J segment region of the VH comprising the human subclass V segment joined to the CDR3 BSD is a human germline sequence.

The invention also provides a method of making an antibody having a binding specificity of a reference antibody, the method comprising:

a) joining a minimal essential binding specificity determinant from the light chain CDR3 of the reference antibody to a diverse population of human VL segments, thereby creating a population comprising diverse VL regions having a reference antibody light chain CDR3 BSD;
b) combining the population of step (a) with a VH region from the reference antibody to create an antibody library; and
c) isolating a member of the library of step c that binds the same antigen as the reference antibody. In some embodiments, the diverse population of human VL segments in (a) are germline.

The method can further comprise:

d) joining a BSD from the heavy chain CDR3 from the reference antibody to a diverse population of human VH segments, thereby creating a population comprising diverse VH regions having the reference antibody heavy chain CDR3 BSD;
e) providing a population of VL regions from the antibody isolated in (c);
f) combining the population of step (d) and step (e) to create an antibody library; and
g) isolating a member of the library of step (f) that binds the same antigen as the reference antibody.

The invention further provides a method of making an antibody having a binding specificity of a reference antibody, the method comprising a) joining a BSD from the heavy chain CDR3 of the reference antibody to a diverse population of human VH segments, thereby creating a population comprising diverse VH regions having the reference antibody heavy chain CDR3 BSD, wherein the BSD is selected from the group consisting of the minimal essential binding specificity determinant, the D segment, and the D segment-FR4;
b) combining the population of step a with a VL region from the reference antibody to produce an antibody library; and
c) isolating a member of the library of (b) that binds the same antigen as the reference antibody. The diverse population of human VH segments of (a) can, e.g, be germline.

In some embodiments, the method o further comprises:

d) joining a BSD from the CDR3 from the light chain of the reference antibody to a diverse population of human VL segments, thereby creating a population comprising diverse VL regions having the reference antibody light chain CDR3 BSD;
e) providing a population of VH regions from the antibody isolated in (d);
f) combining the population of step (d) and step (e) to create an antibody library; and
g) isolating a member of the library of (f) that binds the same antigen as the reference antibody.

In another aspect, the invention provides libraries. For example, such a library can comprise a plurality of nucleic acids that encode a diverse population of heavy chain V segments, wherein the V segments are not linked to a CDR3. The invention also provides a library comprising nucleic acids that encode a diverse population of light chain V segments, wherein the V segments are not linked to a CDR3. The V segments of either or both libraries can be, e.g., human germline.

In another embodiment, the invention provides a library comprising a plurality of human antibody V-region pairs where a V-region pair comprises: i) an unselected heavy chain V-region comprising a human V segment and a heavy chain V-region comprising a human V segment and a heavy chain CDR3 from a reference antibody, and ii) an unselected light chain V-region comprising a human V segment and a light chain CDR3 from the reference antibody.

In other embodiments, the library is a library comprising nucleic acids encoding human antibody V-region pairs, where the VH and VL V segments are each linked to a MEBSD from a reference antibody of interest.

A library of the invention can also comprise nucleic acids encoding a plurality of VH or VL regions, wherein the VH or VL regions comprise V segments from one VH or VL subclass, wherein the V regions lack D and/or J segments. In one embodiment, the V segments of the VH regions are germline and/or the V segments of the VL regions are germline.

The invention also provides a library comprising a plurality of antibody V region pairs, wherein a pair comprises: i) a heavy-chain V region comprising a binding specificity determinant BSD from a heavy chain CDR3 from a reference antibody joined to a diversity of V segments, and ii) a light chain V region comprising a BSD from a light chain CDR3 from the reference antibody joined to a diversity of V segments, wherein at least one of the BSDs comprises less than the reference antibody CDR3.

In another embodiment, a library of the invention is a library comprising a plurality of VH regions comprising a BSD from a heavy chain CDR3 of a reference antibody joined to a diverse population of VH segments, with the proviso that the BSD is less that the reference antibody heavy chain CDR3.

In other embodiments, a library of the invention comprises a plurality of VL regions comprising a BSD from a light chain CDR3 of a reference antibody joined to a diverse population of VL segments, with the proviso that the BSD is less that the reference antibody light chain CDR3.

In another aspect, the invention provides antibodies. In some embodiments, such an antibody comprises a VH region comprising a human V segment, a D segment from a non-human reference antibody and a human J segment, e.g., a germline J segment. The human V segment can also be a germline V segment.

In another embodiment, the invention provides an antibody comprising a VH region having a human germline V segment and a BSD from a heavy chain CDR3 from a reference antibody. The BSD can be, e.g., a CDR3-FR4 from the reference antibody, a CDR3 from the reference antibody or a D segment from the reference antibody, or an MEBSD.

The invention also provides an antibody comprising a VL region having a human germline V segment and a BSD from a light chain CDR3 from a reference antibody. The BSD can be, e.g., a CDR3-FR4 from the reference antibody, an MEBSD, or a CDR3 from the reference antibody.

In any of the methods, libraries, or antibodies of the invention, an antibody can be an IgG, an Fv, an Fab, an Fab', an F(ab')2, a single chain Fv, or an IgG with a deletion of one or more domains.

BRIEF DESCRIPTION OF THE DRAWINGS

FIG. 2 shows the complete nucleotide sequence of KB1082 (SEQ ID NO:1).

FIG. 4 shows the complete sequence of KB5000 (SEQ ID NO:2).

FIG. 5 shows the sequence of the M166 CDRH3 region showing the D- and J-segments (SEQ ID NOS:3-5).

FIG. 6 shows the sequence of variable regions of human antibodies containing a minimal essential binding specificity domain (MEBSD) in CDR3 of the heavy chain from the murine anti-PcrV antibody M166 and a complete human J-region (JH6) (SEQ ID NOS:6-9). The MEBSD is shown in bold and underlined.

FIG. 7 shows the sequence of variable regions of human antibodies containing a MEBSD in CDR3 of the heavy chain from the murine anti-PcrV antibody M166 and a complete human J-region (JH3) (SEQ ID NOS:10-13). The MEBSD is shown in bold and underlined.

FIG. 8 shows the results of an exemplary ELISA analysis to detect binding to PcrV antigen.

FIG. 9 shows sequences of V-regions of anti-PcrV antibodies with sequences close to human germ-line (SEQ ID NOS: 14-17). Amino acid residues which differ from the closest human germ-line sequence in the V-segment or FR4 are underlined and the CDR3 sequences are marked in bold. The VH-segment of antibody F6 is identical to human germ-line sequence VH3-33, except for the first amino acid. The VL-segment of antibody 1F1 is identical to human germ-line VκIIIL6.

DETAILED DESCRIPTION OF THE INVENTION

Definitions

Figure 1:
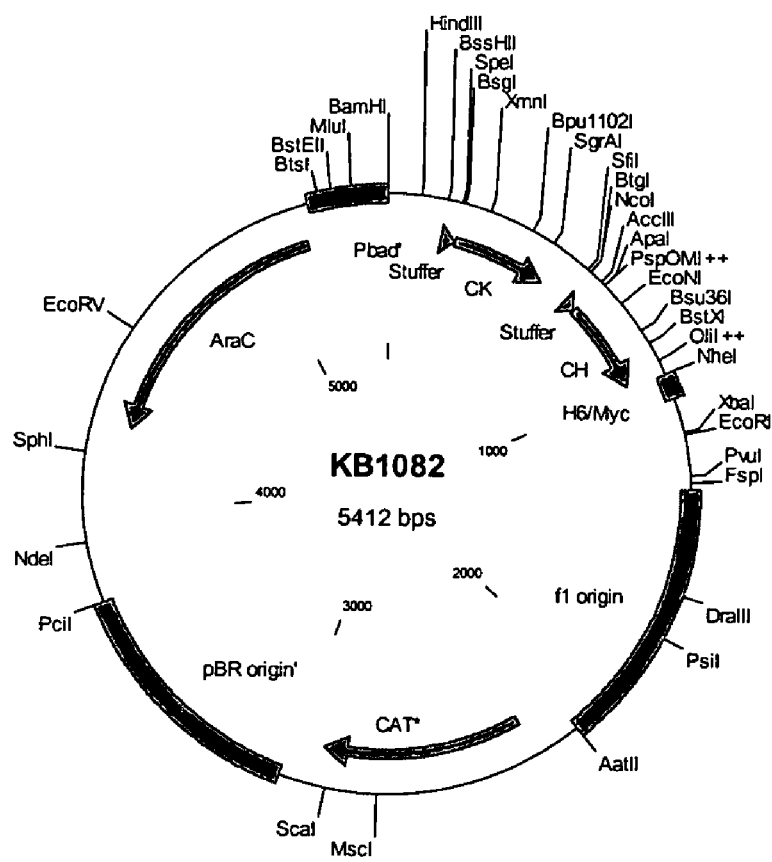
FIG. 1 shows a plasmid map of a vector for expression of Fab fragments from *E. Coli*. Plasmid KB 1082 contains an arabinose-inducible promoter for directing expression of a dicistronic message containing coding sequences for a kappa light chain and a heavy chain Fd fragment.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region (V) of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, papain digestion above the hinge produces a Fab. Pepsin digests an antibody below the disulfide linkages in the hinge region to produce F(ab)'2, a dimer of Fab' which itself is a light chain joined to VH-CH1-hinge by one or more disulfide bonds. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab or Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies of the invention include single chain antibodies (antibodies that exist as a single polypeptide chain), often single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) *Proc. Nat. Acad. Sci. USA*, 85: 5879-5883. While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons, but the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Antibodies of the invention include all those that have been displayed on phage (e.g., scFv, Fv, Fab and disulfide linked Fv (Reiter et al. (1995) *Protein Eng*. 8: 1323-1331). Antibodies can also include diabodies and miniMabs.

"V-region" as used herein refers to an antibody variable region comprising the segments of Framework 1 (FR1), CDR1, Framework 2 (FR2), CDR2, Framework 3 (FR3), CDR3 and Framework 4 (FR4).

The term "V-segment" as used herein is that part of a variable region that comprises the segments FR1, CDR1, FR2, CDR2, and FR3 and does not include CDR3 and Framework 4 (FR4).

A "D-segment" refers to the region of a heavy chain variable region (in this case, a CDR3 in the V-region) that is encoded by a D gene segment. Similarly, a "J-segment" refers to a region encoded by a J gene segment. These terms include various modifications, additions, deletions, and somatic mutations that can occur or be introduced during affinity maturation.

"Binding" refers to the adherence of molecules to one another, for example, enzymes to substrates, antibodies to antigens, DNA strands to their complementary strands. Binding occurs because the shape and chemical natures of parts of the molecules surfaces are complementary. A common metaphor is the "lock-and-key," used to describe how enzymes fit around their substrate.

The "binding specificity" of an antibody refers to the ability of an antibody to recognize an antigen to the exclusion of other antigens and is generally measured against nonspecific background binding. Typically, an antibody is considered specific when it binds to the target antigen at least 10 times above background binding.

A "binding specificity determinant" (BSD) as used in the context of this invention refers to a CDR3-FR4 region, or a portion of this region that mediates binding specificity. BSDs function as heavy chain and light chain pairs, i.e., a BSD functions together with its cognate partner on a complementary chain of a reference antibody. A binding specificity determinant therefore can be a CDR3-FR4, a CDR3, a minimal essential binding specificity determinant of a CDR3, the D segment (with regard to a heavy chain region), or other regions of CDR3-FR4 that confer the binding specificity of a reference antibody.

A "minimal essential binding specificity determinant" (MEBSD) as used herein refers to any region smaller than the CDR3 that confers binding specificity when present in the V region of an antibody. The MEBSD functions in a pair together with a cognate partner on a complementary chain of a reference antibody.

"Complementarity-determining region" or "CDR" refers to the art-recognized term as exemplified by the Kabat and Chothia. CDRs are also generally known as hypervariable regions or hypervariable loops (Chothia and Lesk (1987) *J. Mol. Biol.* 196: 901; Chothia et al. (1989) *Nature* 342: 877; Kabat et al., *Sequences of Proteins of Immunological Interest* (National Institutes of Health, Bethesda, Md.) (1987); and Tramontano et al. (1990) *J. Mol. Biol.* 215: 175). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, *J. Mol. Biol.* 196, 901-917; Chothia, et al., 1989, *Nature* 342, 877-883; Chothia, et al., 1992, *J. Mol. Biol.* 227, 799-817; Al-Lazikani et al., *J. Mol. Biol.* 1997, 273 (4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. *Nucleic Acids Res.* January 1; 29 (1): 207-9 (2001); MacCallum et al, *J. Mol. Biol.,* 262 (5), 732-745 (1996); Martin et al, *Proc. Natl. Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Antigen" refers to substances that are capable, under appropriate conditions, of inducing a specific immune response and of reacting with the products of that response, that is, with specific antibodies or specifically sensitized T-lymphocytes, or both. Antigens can be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" is used herein to refer to any substance to which an antibody binds, or for which antibodies are desired, regardless of whether the substance is immunogenic. For such antigens, antibodies can be identified by recombinant methods, independently of any immune response.

"Epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR.

"Target" is used here to refer to the molecule to which a reference antibody binds. Thus, "target" is often used herein synonymously with "antigen".

A "reference antibody" as used here refers to an antibody for which the practitioner wants to obtain a variant with "improved" characteristics, e.g., reduced immunogenicity, increased affinity, and the like. The reference antibody is the source of the pairs of variable region BSDs.

"Library" means a collection of nucleotides sequences, e.g., DNA, encoding antibodies within clones; or a genetically diverse collection of antibody polypeptides.

"Repertoire library" refers to a library of genes encoding antibodies or antibody fragments such as Fab, scFv, Fd, LC, VH, or VL, which is obtained from the natural ensemble, or "repertoire", of antibodies present in human donors, and obtained primarily from the cells of peripheral blood and spleen. Often, the human donors are "non-immune", i.e., not presenting with symptoms of infection.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Link" or "join" or "fuse" refers to functionally connecting polypeptide, including, without limitation, recombinant fusion of the coding sequences.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or residues such as deoxyinosine residues. The term nucleic acid refers to gene, cDNA, mRNA, oligonucleotide, and polynucleotide.

"Recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

"Recombinant polypeptide" refers to a polypeptide expressed from a recombinant nucleic acid, or a polypeptide that is chemically synthesized in vitro.

"Purified" or "isolated" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

Introduction

Current antibody humanization strategies retain substantial amounts of non-human sequence in the human sequence selection process (e.g., either all six CDRs or at least one entire V-region is retained in the initial selection). Retention of binding specificity and affinity is therefore constrained to depend on the selected human sequences being highly homologous to the original non-human sequences. At the same time, however, considerable sequence divergence is required to make non-human proteins sufficiently human to minimize, immunogenicity in humans. The result is a compromise between retention of binding specificity and affinity and replacement of the non-human protein sequence with human, such that "humanized" antibodies are not fully human, and have typically lost affinity relative to the starting antibody.

The present invention is based on the discovery that neither the optimal antigen-binding conformation of the BSD pair, nor antigen binding by the other CDRs, requires significantly greater homology than the average homology of human V-regions to those of the non-human in question, even though the vast majority of human V-regions would not support the antigen-binding conformation of the $CDR3_2$, nor provide antigen binding by the other CDRs. Thus, the invention provides methods of transferring BSD pairs from a reference antibody to human V-segments, thereby creating humanized antibodies that have minimal potentially immunogenic sequences.

Although the invention is largely described in terms of applying the methods to humanizing non-human reference antibodies, it is understood that the methods can be employed in any situation where it is desirable to transfer BSDs from a reference antibody to non-reference antibody V-segments. For example in certain applications, e.g., veterinary medicine applications, it may be desirable to transfer the BSDs of a reference antibody to V segments from other species. The reference antibody can be from any species, including mouse, rat, or rabbit, as well as sheep, horse, bovine, goat, camellids, or primates, or any other vertebrate that produced antibodies.

The present invention provide methods of humanizing antibodies where the resulting antibodies retain binding specificity and affinity while at the same time have most of the non-human sequences replaced with human sequences. This is accomplished by transferring a BSD pair from the reference antibody, e.g., a CDR3 pair ($CDR3_2$). In antibodies that are affinity-matured, e.g., the reference antibody, the heavy chain and light chain BSDs are in close contact with one another and are optimized for mutual stabilization of the combined antigen-binding conformation, hence, they form a unit, i.e., a BSD pair. The antigen-binding conformation is, of course, dependent on the support of the underlying frameworks of the V-regions. When an affinity-matured BSD, e.g., that of the reference antibody, is combined with the structural diversity and stability of the complete human repertoire of heavy chain or light chain V-segment pairs, scaffolds that fully support the optimal antigen-binding conformation of the BSD are readily identified with the aid of selection systems including, but not limited to, phage display, cell viability, colony lift binding assays (CLBA), or a variety of immunoassays, e.g., ELISA assays.

Further, transfer of a BSD pair to diverse germline V-segments often result in selection of V-regions that that have affinities of greater than 50 nM. These selected V-regions can also be incorporated into the affinity maturation process of any antibody. V-segment libraries are relatively small without CDR3 repertoires, thus selection of human V-regions can also be combined with limited mutagenic diversification of one or both BSDs in libraries of searchable size for many conventional selection systems.

It should be emphasized that while the present invention minimizes the homology constraint on antibody humanization, it does not necessarily impose any selective pressure against homology. Thus, human V-segments with high homology to the non-human parent segments can still be selected by the present invention, e.g., if they retain equal or higher affinity for the antigen.

The following sections will additionally describe V-region repertoire cloning, transfer of BSDs, generation of libraries, and screening methodologies.

V-Segment Repertoire Cloning

The V-segment repertoire used in generating libraries to replace the heavy and/or light chain V-segment of the reference antibody can be from any source. The human repertoires can be generated, e.g., by polymerase chain reaction (PCR) amplification using primers appropriate for the desired segments from cDNA obtained from peripheral blood or spleen, in which case the repertoires are expected to contain clones with somatic mutations. Alternatively, the repertoires can be obtained by amplification of genomic DNA from non-immune system cells in order to obtain germline-encoded sequences.

The human germline V-segment repertoire consists of 51 heavy chain V-regions, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, also Chothia et al., 1992, *J Mol Biol* 227:776-798; Tomlinson et al., 1995, *EMBO J.* 14:4628-4638; and Williams et al., 1996, *J Mol Biol* 264:220-232).

V-segment variants generated by somatic hypermutagenesis during the affinity maturation process may also make important contributions to the V-segment repertoire, since these mutations appear to be non-random, and may confer structural adjustments which facilitate high-affinity antigen specificity. While naïve antibodies are optimized for broad specificity and low affinity for maximum binding diversity, affinity matured antibodies may contain structural adaptations which favor the more rigid CDRs required for high-affinity antigen-specific binding (e.g., Diaz and Klinman, 2000, *Immunol Res.* 21:89-102).

Human V-region repertoires, both germline and affinity-matured, can be recovered, e.g., from peripheral blood lymphocytes (PBL), often pooled from multiple (e.g., at least 10) healthy individuals, using conventional cDNA cloning methods (Sambrook and Russell, eds, *Molecular Cloning: A Laboratory Manual,* 3rd Ed, vols. 1-3, Cold Spring Harbor Laboratory Press, 2001). Insofar as the germline frequency distribution is not uniform in expressed sequences, it is prudent to capture at least $10^3$ independent clones for each of the three V-region isotypes (VH, Vκ, and Vλ) to ensure optimal diversity of the repertoires. The PCR can be used to amplify V-region sequences during the cloning process. However, exponential amplification mechanisms are prone to random biases, and this may be compounded by the use of degenerate primers, which have variable priming efficiencies, resulting in a loss of diversity. Thus, when amplification is desired, it may be desirable, where possible, to use a primer-independent linear amplification method, such as in vitro transcription (Sambrook and Russell, eds, Molecular Cloning: A Laboratory Manual, 3rd Ed, vols. 1-3, Cold Spring Harbor Laboratory Press, 2001).

In one embodiment, mRNA is isolated from human PBLs or other lymphocyte-rich tissues using standard methods (e.g., *Current Protocols in Molecular Biology*, Ausubel. ed. John Wiley & Sons, Inc. New York, 1997). The human V-region sequences are copied and cloned using standard PCR protocols, e.g., as described in the Examples or using in vitro transcription-based protocols. For example, in an in vitro transcription protocol, immunoglobulin-encoding first-strand cDNA is copied from the mRNA template using a reverse transcriptase (RT) and primers which are complementary to the human heavy chain and light chain constant region genes, Cμ1 or Cγ1, Cκ, and Cλ. Cμ1 primers are required for the capture of naïve germline VH sequences, while Cγ1 primers allow the capture of affinity-matured VH domains. For the synthesis of second-strand cDNA, the second-strand primers may also contain a promoter sequence, such as that of bacteriophage T7, which when incorporated into the complementary strand, allows continuous linear amplification of the V-region sequences in vitro using T7 DNA-dependent RNA polymerase (Sambrook and Russell, eds, *Molecular Cloning: A Laboratory Manual,* 3rd Ed, vols. 1-3, Cold Spring Harbor Laboratory Press, 2001). If desired, the amplification process can be repeated by copying the RNA into double-stranded cDNA using complementary primers, and then repeating the in vitro transcription step. The in vitro transcription procedure is necessary to provide a sufficient quantity of nucleic acid for cloning the V-region library into a plasmid vector, which should be a standard expression vector such as one of the pBR322 derivatives. After transformation into *E. coli* cells, the size of the V-region library in independent clones can be determined and the quality of the library assessed by sequencing a sufficient number of clones (for example at least 30 of each isotype) to determine the proportion of open reading frames and the proportional representation of germline diversity. It is relatively easy to collect at least 104 independent clones of each isotype, which should ensure that all germline genes are amply represented with open reading frames.

For BSD-guided V-segment selection, the human CDR3s is eliminated from the V-region repertoires. This can be readily done, e.g., during the final cDNA synthesis step, before cloning by using degenerate primers which are collectively complementary to the carboxyl terminal sequences of Framework 3 in all germline V-region genes. The C-terminal sequences of Framework 3 are highly conserved, so that a restriction endonuclease site can be included in the primer to create a universal "sticky end" for in-frame ligation to any guiding CDR3-FR4 without altering any Framework 3 sequence.

In other embodiments, the V-segment can be amplified by using suitable PCR primers, e.g., primers described in the Example section. Sets of oligonucleotide primers are designed to 5' and 3' regions of the V-segments for cloning the V-segment repertoire. Suitable primer sequences are known (e.g., Welschof et al., *J. Immunological Methods* 179:203-214, 1995 and Little et al., *J. Immunological Methods,* 231: 3-9, 1991]) or can be designed. An oligonucleotide or a set of oligonucleotides are used to construct CDR3-FR4 regions and are either linked to the V-segment sequences through an introduced restriction site or by overlap-extension PCR or by primer extension. For example, amplification primers at the 3' of the V-segment may be designed to sequences encoding amino acids 86-89 (according to the Kabat numbering system) for Vh; amino acids 81-86 for Vκ and 81-85 for Vλ and include a non-templated restriction site near the 5' end. The oligonucleotide encoding CDR3-FR4 may extend into the region encoding VYYCAR (SEQ ID NO:18) on the heavy chain (Kabat amino acids 89-94) or VYYC (SEQ ID NO:19) (Kabat residues 85-88) on the light chain and contain a restriction site compatible with that at the 3' end of the V-segment repertoire. Thus, a library of complete V-regions can be generated by ligation of the CDR3-FR4 oligonucleotide to the V-segment repertoire. The CDR3-FR4 sequence can also be joined to the V-segment by other methods known to those with skill in the art, such as overlap extension PCR or primer extension of cRNA synthesized from the V-segment repertoire. The sequences encoding complete V-regions are cloned into a suitable expression vector and can be fused to constant region sequences at this stage for expression as Fab, Fab' or other antibody fragments, whole IgG or fusion proteins used for display on a cell or virus.

Libraries for-guided V-region repertoires or V-region-guided BSD repertoires may be expressed in any cell type, including bacteriophage, yeast, bacteria, mammalian cells and the like. The library can be screened for antigen-binding activity by any of a number of assays, e.g., high-throughput ELISA-based assays. Such libraries can also be expressed in display format, such as on bacteriophage, bacterial cells, yeast cells, mammalian cells or ribosomes, and screened for binders as described in the art.

A heavy or light chain V-segment library can be directed to only one V segment subclass or isotype. In such an embodiment, for example, where it is desired to select a human V segment isotype that most closely matches the V-segment isotype of the reference antibody, appropriate primers can be used to amplify only sequences corresponding to the desired isotype.

In some embodiments, the V-segments are germline. As noted above, there are 51 germ-line VH genes in humans and each of these can be recombined. There are 40 Vκ genes and 31 Vλ genes. The VH germ-line genes are sub-divided into 7 subclasses (VH1-VH7) and the germ-line light chains are sub-divided into 16 sub-classes (Vκ1-Vκ6 and Vλ1-Vλ10). Germ-line human V-gene sequences can be cloned from human genomic DNA by PCR or linear amplification methods in the same way that re-arranged and somatically mutated V-gene sequences are cloned from cDNA. For example, degenerate primers encoding all germline Framework 1 amino-terminal sequences (not including signal peptide leaders) and all Framework 3 carboxyl-terminal sequences can be used for ligation to CDR3. After cloning, selection for intact reading frames, sequence verification, and archiving, the repertoires can be used for assembly of combinatorial human V-region libraries for BSD pairs.

Transferring BSDs of the Reference Antibody

BSDs from the reference antibody are transferred to a library of V-segment sequences generated as described above. The BSDs can be incorporated into the expression vector before or after the population of V-segments is cloned into the expression vector. The BSD that is transferred can be a CDR3-FR4, a CDR3, a D segment (where the BSD is from the heavy chain), a MEBSD, or any other fragment of CDR3-FR4 that has binding specificity in combination with the complementing BSD from the other chain of the reference antibody. It is understood that when transferring a BSD from a reference antibody to a different V-region, the structure of the heavy or light chain V region is maintained in the resulting V-region. Thus, if the BSD from the reference antibody is a subregion of CDR3-FR4, the complete CDR3-FR4 structural length is maintained, i.e., the remainder of the CDR3-FR4 residues that are not from the reference antibody are made up of other residues, typically human germline residues.

As noted, the BSD can include Framework 4 regions, e.g., from the reference antibody, which are part of the J-segments, but which are highly conserved among mammals, and are important for CDR3 structure. These sequences can, for example, be amplified by PCR with primers containing restriction sites for in-frame ligation to Framework 3, and other unique restriction sites downstream from the carboxyl terminus of Framework 4, e.g., for ligation to the C-region. Each CDR3-FR4 is then transferred into the appropriate sites of the V-region library construct. Alternatively, the desired sequence or mix of sequences for the CDR3-FR4 region can be synthesized as one continuous oligonucleotide or mix of oligonucelotides and can be joined to the V segment repertoire by primer extension using in vitro transcribed cRNA synthesized from the repertoire as a template for first-strand cDNA synthesis. Diversity can be introduced into a region, e.g., CDR3 and/or FR4.

In other embodiments, the FR4 region can be a human FR4, e.g., a germline FR4. In some embodiments, the libraries can comprise a diversity of FR4 sequences. The human FR4 sequences are typically introduced by PCR using appropriate primers to amplify the FR4 sequences to be incorporated into the library expression vector. The FR4 sequences can be introduced into a library to which the CDR3 or MEBSD has already been transferred, or can be introduced concurrently with the CDR3 or MEBSD. Diversity can be introduced into the FR4 using mixed oligonucleotides, or mutagenesis protocols as described for introducing diversity into a CDR3. The FR4 can be cloned from a library, e.g., as a J segment from a human repertoire.

The BSD that is transferred can also be a reference antibody CDR3. Again, the transfer is performed via amplification methodology to amplify the desired sequence containing the CDR3 for incorporation into the expression vector at the appropriate site using known methodologies Defining Minimum Essential Binding Specificity Determinants The BSD can also be a sequence that is less than the complete CDR3, e.g. the D segment of a heavy chain CDR3 or a MEBSD. As appreciated by one of skill in the art, when the reference antibody BSD is less than a complete CDR3, a complete CDR3 still results in the antibody expression library, as the remaining CDR3 residues are incorporated into the construct. For example, appropriate oligonucleotides can be designed to incorporate human sequences, e.g., germline J segments, to replace the CDR3 residues that are not part of the MEBSD.

The MEBSD is the region within a CDR3 sequence or a pair of CDR3s that is required to retain the binding specificity of the reference antibody when combined with human sequences that re-constitute the remainder of CDR3 and the rest of the V-region. The MEBSD can be defined empirically or can be predicted from structural considerations.

For empirical determination, methods such as alanine scanning mutagenesis can be performed on the CDR3 region of a reference antibody (Wells, *Proc. Natl. Acad. Sci. USA* 93:1-6, 1996) in order to identify residues that play a role in binding to antigen. Additional analyses can include Comprehensive Scanning Mutagenesis, in which each residue of CDR3 is replaced, one-at-a-time, with each of the 19 alternative amino acids, rather than just replacement with alanine. Binding assays, e.g, colony-lift binding assays, can be used to screen libraries of such mutants to determine those mutants that retain binding specificity. Colonies that secrete antibody fragments with assay signals reduced by at least ten-fold relative to the reference antibody can be sequenced and the DNA sequences used to generate a database of amino acid positions in CDR3 that are important for retention of binding. The MEBSD can then be defined as the set of residues that do not tolerate single-site substitution, or which tolerate only conservative amino acid substitution.

An MEBSD can also be determined by deletion analysis in which progressively shorter sequences of a reference antibody CDR3 are evaluated for the ability to confer binding specificity and affinity. This is accomplished by substituting the CDR3 residues with progressively longer human sequences, e.g., from a human germline J segment.

The MEBSD can also be deduced from structural considerations. For example, if the x-ray crystal structure is known, or if a model of the interaction of antibody and antigen is available, the MEBSD may be defined from the amino acids required to form suitable contact with the epitope and to retain the structure of the antigen-binding surface.

Alternatively, the MEBSD can be predicted from the primary structure of the CDR3. In VH domains, for instance, the MEBSD can, in some antibodies, correspond to a D-segment (including any deletions or identifiable N-additions resulting from the re-arrangement and maturation of the reference antibody). In this case, the J-segment may be replaced by a cloned human J-segment or a repertoire of J-segments. The binding specificity of the modified reference VH-domain with substituted J-segment may be determined in combination with a suitable complementary light-chain. This complementary chain can be the light chain of the reference antibody or can be a human light chain containing the CDR3 of the light chain of the reference antibody. Binding specificity can be determined by colony-lift binding assay or by another known assay methodology. If colonies secreting antigen-binding antibodies are not identified by this approach, additional sequences from the reference antibody CDR3 may be substituted for corresponding sequences in the J-segment and these additional mutants screened with the complementary light chain until a MEBSD is identified.

MEBSDs can similarly be identified in CDR3 of the light chain, in which case the complementary chain used in the screening assay comprises a $V_H$-domain. In this case the $V_H$ domain may be derived from the reference antibody or may be a human $V_H$ domain with the CDR3 from the reference antibody. As there is no D-segment in the light chain, the MEBSD can be deduced by scanning mutagenesis or by inspection of the sequence of CDR3 and substitution of those sequences in CDR3 encoded by the V-gene segment, or those sequences encoded by the J-segment. Screening for antigen binding, e.g., by colony-lift binding assay, can be used to define which segment of the CDR3 constitutes the MEBSD.

Further, software programs such as JOINSOLVER™ Souto-Carneiro, et al., *J. Immunol.* 172:6790-6802, 2004) can be used to analyze CDR3 of immunoglobulin gene to search for D germline sequences. The strategy of JOINSOLVER® is to search for D germline sequences flanking $V_H$ and $J_H$ germline genes. Additionally, it searches for P- and N-type additions in the $V_H$D and $DJ_H$ junctions. The human D germline gene database employed includes all D segments from the IMGT databank as well as the reverse and DIR germline genes.

Expression of Antibodies

Libraries of secreted antibodies or antibody fragments can be expressed in prokaryotic or eukaryotic microbial systems or in the cells of higher eukaryotes such as mammalian cells. The antibody library can be a library where the antibody is an IgG, an Fv, an Fab, an Fab', an F(ab')$_2$, a single chain Fv, an IgG with a deletion of one more domains, or any other antibody fragment that includes the V-region.

The antibodies can be displayed on the surface of a virus, cell, spore, virus-like particle, or on a ribosome. For this purpose, one or both chains of the antibody fragment are typically expressed as a fusion protein, for example as a fusion to a phage coat protein for display on the surface of filamentous phage. Alternatively, the antibodies of the antibody library can be secreted from a host cell.

The following provides an exemplary description using secretion systems to express the antibodies as Fab or Fab' fragments. It is readily apparent to those in the art, however, that the expression systems can be adapted for any library format. For this general example, a library of complete V-regions is constructed by ligation of oligonucleotides encoding CDR3-FR4 segments to the V-segment repertoire as described above. The amplified sequences encoding complete V-regions are cloned into a suitable expression vector and can be fused to constant region sequences at this stage for expression of Fab or Fab' molecules. The antibody fragments can be secreted from prokaryotic or eukaryotic cells including bacteria, yeast, plant cells and mammalian cells.

In one preferred method, the V-region libraries are expressed and secreted as assembled and functional Fab or Fab' fragments from a microbial host cell. Secreted fragments are then screened for antigen binding e.g., by a filter screening assay or ELISA as described further below. An example of a suitable expression vector for secretion of antibody fragments from yeast is pESC (obtained from Stratagene), which contains two separate promoters for expression of the heavy and light chains of the antibody fragment. Vectors for secretion from *E. coli* may make use of dicistronic messages for the co-ordinate expression of heavy and light chains, as exemplified by plasmid KB1082, shown in FIG. 1, or may use two separate transcription units for the two antibody chains, as exemplified by KB1150 shown in FIG. 3. A signal peptide is advantageously fused to the N-terminus of the mature heavy and light chain coding sequences in order to facilitate secretion from the host cell. The sequence of the signal peptide, which is encoded as part of the expression plasmid, may be provided by a naturally occurring secretion signal appropriate for the host cell. For example, a yeast invertase signal peptide may be chosen for secretion from yeast cells. For *E. coli*, a number of suitable prokaryotic signal peptides are known in the art, including the PelB or OmpA signal sequences. Alternatively a non-natural synthetic signal peptide may be chosen. An example of a synthetic signal peptide, suitable for antibody libraries expressed in *E. coli*, is the non-natural signal sequence designated SP2 the amino acid sequence of: MGKKQLVVFALLLAFLSPAMA (SEQ ID NO:20).

Library Screening

As explained, the invention is not limited to technologies where the antibody constructs are expressed in microbial cells. Other screening methodologies can also be employed. The following provides an example of library screening using a microbial expression system.

Filter screening methodologies have been described for detection of secreted antibodies specific for a particular antigen. In one format, the secreted antibody fragments are trapped on a membrane which is probed with soluble antigen (Skerra et al (1991) *Anal Biochem.* 196:151-5). In this case, bacteria harboring plasmid vectors that direct the secretion of Fab fragments into the bacterial periplasm are grown on a membrane or filter. The secreted fragments are allowed to diffuse to a second "capture" membrane coated with antibody which can bind the antibody fragments (eg anti-immunoglobulin antiserum) and the capture filter is probed with specific antigen. Antibody-enzyme conjugates can be used to detect antigen-binding antibody fragments on the capture membrane as a colored spot. The colonies are re-grown on the first membrane and the clone expressing the desired antibody fragment recovered.

Colony lift binding assays have also been described in which the antibodies are allowed to diffuse directly onto an antigen-coated membrane. Giovannoni et al have described such a protocol for the screening of single-chain antibody libraries (Giovannoni et al., *Nucleic Acids Research* 2001, Vol. 29, No. 5 e27).

Libraries of secreted antibody fragments can also be screened by ELISA, either using pools of multiple clones or screening of individual clones each secreting a unique antibody sequence. One such method for screening individual clones is described by Watkins et al (1997) Anal. Biochem. 253: 37-45. In this case, microtiter wells were coated with anti-Fab antibody to capture Fab fragments secreted directly in the wells. The Fab samples were then probed with soluble biotinylated antigen followed by detection with streptavidin-alkaline phosphatase conjugates.

In some embodiments of the present invention, screening systems are used that result in relatively low levels of expression. For example, when a colony lift binding assay (CLBA, Govannoni et al., 2001, *Nucleic Acids Research* 29 (5):e27) is combined with an immuno-chemiluminescent labeling system, the sensitivity of the system, even for sub-micromolar $K_d$ affinities, permits expression levels which are below the aggregation thresholds of most Fabs.

Exemplary protocols for CLBA are provided in the Examples section. Conditions for the CLBA can be optimized empirically. For example, the transcription inducer may be optimized to avoid over-expression or under-expression by experimentally determining the amount required for e.g., 100% ten-fold-over-background detection by chemi-luminescence of the library when a universal antibody fragment-binder, e.g., an anti-human Ig antibody, is used as the antigen on the filter. The stringency of selection can also be manipulated by adjusting the concentration of antigen on the filter. For example, the antigen concentration on which the antibody fragment to be humanized produces a minimal signal, e.g., no more than 10-fold over background, may be determined and used for selection, so that antibodies with higher affinities and/or higher expression levels may be readily identified by the intensity of their signals. Expression levels may be determined in parallel by making replicate colony lifts and incubating them on filters coated with a universal antibody binder, such as an anti-human Ig antibody. The relative affinity for each colony is then determined as the ratio of its chemiluminescent signal from the antigen filter to its signal from the antibody-binder filter, and the ratios can be compared to each other and to the same ratio for the parent non-human antibody to rank-order the selected antibodies according to affinity. Absolute affinities may then be determined by any of several methods, e.g., surface plasmon resonance methods (SPA, Fägerstam et al., 1992, *J Chromatog* 597:397-410). Human Fc domains may be appended to selected Fabs for expression and production as full-length Ig, generally without loss of affinity.

In some cases, the selected human V-regions of the highest-affinity antibodies may not support sufficiently robust expression of a Fab or other derivative Ig for cost-effective production for intended applications such as therapeutics or diagnostics. In such cases, the expression data provided by the replicate filter in the CLBA may be used to identify the highest-affinity Fabs with the desired expression levels. The expression stringency of the assay may also be increased by using antigen densities on the filter which are restrictive for the parent antibody when expressed at higher levels than those actually used for the selection. Selected higher-expressing Fabs can be affinity-matured, if desired, by mutagenesis of the BSD paris, and selection by CLBA as described above and below.

Guided selection can also be used to replace one BSD at a time. If the original heavy chain CDR3 BSD is retained, then the guiding affinity will be high enough for guided selection of a human light chain CDR3 BSD, though the same is less likely to be true if the original light chain CDR3 BSD is retained for guided selection of a human heavy chain CDR3 BSD. The CDR3 BSD repertoires used for V-region-guided selection can be captured from mRNA from PBL or other immune tissues using degenerate primers complementary to all germline Framework 3 and Framework 4 sequences. Alternatively, the repertoires can be constructed synthetically by recombining the sequences for the germline D-segment and J-segment repertoires (Tomlinson et al., 1995, *EMBO J.* 14:4628-4638) with a few random residues at the D-segment junctions to simulate N-addition.

Antibodies with Human Germline V-Regions

Selected antibodies can deviate from the human germline V-region sequences at a number of positions that don't significantly contribute to the binding activity of the antibody. It is also possible that many of these alterations will induce an immune response in at least some humans, which may thereby compromise the efficacy of the antibody. As, the human germline V-region sequences should be the least immunogenic, the V-region sequences of the such selected antibodies can be converted to the human germline sequences and tested for retention of affinity.

In some embodiments, an antibody made in accordance with the invention has a V segment plus FR4 that is greater than 90% identical, often greater than 95% identical, and preferably identical to a human germline sequence. Such antibodies can be identified by comparing the V segment and FR4 sequence to know human germline sequences.

If some loss of affinity does occur upon conversion to the germline sequences, the affinity can be recovered by affinity maturation of the CDR3 sequences.

Affinity Maturation

BSD-guided V-region selection often produces antibodies of equal or even higher affinity than that of the reference antibody. However, it may be desirable to also employ affinity maturation techniques, either before or after the selection procedure. "Affinity matured" in the context of antibodies refers to an antibody that is derived from a reference antibody, binds to the same epitope as the reference antibody, and has a higher affinity for the antigen than that of the reference antibody. For example, affinity maturation may be performed on antibodies selected in accordance with the invention in which the heavy and/or light chain V-segments are germline.

To avoid immunogenicity, affinity maturation is typically performed focusing on the BSD pair. Efficient affinity maturation of the BSD can be accomplished, e.g., using the method of Parsimonious Mutagenesis (P M, Balint and Larrick, 1993 *Gene* 137:109-118) to diversify the BSD pair, and then screening for higher affinity binders, e.g., using a CLBA or other method.

In other embodiments, affinity maturation techniques can be performed using fragment complementation systems, e.g., described in U.S. patent application Ser. Nos. 09/526,106 (abandoned) and 09/999,413 (abandoned); the competitive activation system (CompAct) described in U.S. patent application Ser. No. 10/076,845 (abandoned); and the auto-inhibited β-lactamase reactivation systems (ReAct or RAIR) described in U.S. patent application Ser. Nos. 10/208,730, now U.S. Pat. Nos. 7,335,478, and 10/677,131, now U.S. Pat. No. 7,432,063.

Affinity Determination

Antibodies isolated from primary screens of secreted antibodies or selected from display technologies are subjected to further analysis in order to determine quantitative affinities for target antigen. Typically, the antibodies are expressed in soluble form for this purpose, which may necessitate re-formatting as a soluble fragment or as a whole IgG if the antibodies were originally isolated as fusion proteins from a surface display approach.

Affinities can be determined by a variety of competition binding studies requiring interaction of antibody in solution with native antigen, either in solution or on whole cells whole cells, and analysis of affinity from scatchard plots. Alternatively affinity may be determined on isolated antigen, for example in Enzyme-linked Immunosorbent Assays (ELISA) or by surface plasmon resonance analysis or numerous other immunoassays known in the art (see, e.g., Harlow & Lane, Using Antibodies, A Laboratory Manual, Cold Spring Harbor Laboratory Press, 1999). Harlow & Lane and similar procedure manuals also disclose techniques to map epitopes or alternatively, competition experiments, to determine whether an antibody binds to the same epitope as the donor antibody. Functional, e.g., cell-based assays can also used to demonstrate that the specificity and activity of the reference antibody is retained.

The first screening steps, e.g., screens that analyze replacement of one exchange cassette where the remainder of the antibody sequences are reference antibody, an antibody that has a demonstrable affinity for the antibody is selected. The affinity may be lower than the reference antibody.

Antibodies of the invention are typically high affinity antibodies and may have dissociation constants in the range 50 nM to 1 pM. Preferably the antibody has an affinity less than 10 nM and most preferably less than 1 nM. Where the antibody has one or more germline V segments, the affinities are preferably less than 50 nM, often less than 20 nM, most preferably less than 1 nM. Similarly, an antibody that has been selected using the methods of the invention in which the D segment from the heavy chain of the reference antibody has been transferred, or in which one or more MEBSDs from the reference antibody CDR3s have been transferred, or in which one or both CDR3s from the reference antibody has been transferred, preferably have an affinity that is less than 50 nM, often less than 20 nM, preferably less than 1 nM.

The antibodies have affinities typically no more than 5-fold worse, often no more than 2-fold worse than the reference antibody and most preferably have higher affinity, e.g., 2-fold, 5-fold, or higher, than the reference antibody.

General Methods

Nucleic Acids and Polypeptides

Expression methodology is well known to those of skill in the art. Recombinant polypeptides can be made by ligating the appropriate nucleic acid sequences encoding the desired amino acid sequences by methods known in the art, in the proper reading frame, and expressing the product by methods known in the art (see, e.g., Scopes, Protein Purification: Principles and Practice, Springer-Verlag, New York 1994; Sambrook and Russell, eds, Molecular Cloning: A Laboratory Manual, 3rd Ed, vols. 1-3, Cold Spring Harbor Laboratory Press, 2001; and Current Protocols in Molecular Biology, Ausubel, ed. John Wiley & Sons, Inc. New York, 1997).

Nucleic acids encoding the polypeptides of the invention can be obtained using routine techniques in the field of recombinant genetics (see, e.g., Sambrook and Russell, eds, Molecular Cloning: A Laboratory Manual, 3rd Ed, vols. 1-3, Cold Spring Harbor Laboratory Press, 2001; and Current Protocols in Molecular Biology, Ausubel, ed. John Wiley & Sons, Inc. New York, 1997).

Often, the nucleic acid sequences encoding the polypeptides to be expressed are amplified from cDNA or genomic DNA libraries using oligonucleotide primers. Amplification techniques can be used to amplify and isolate sequences from DNA or RNA (see, e.g., Dieffenbach & Dveksler, PCR Primers: A Laboratory Manual (1995)). Alternatively, overlapping oligonucleotides can be produced synthetically and joined to produce one or more domains.

Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; (Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117.

In some embodiments, it may be desirable to modify an antibody sequence of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) Gene 8:81-97, Roberts et al. (1987) Nature 328: 731-734.

In some embodiments, the recombinant nucleic acids encoding the polypeptides to be expressed are modified to provide preferred codons which enhance translation of the nucleic acid in a selected organism (e.g., yeast preferred codons are substituted into a coding nucleic acid for expression in yeast).

Expression Cassettes and Host Cells

There are many expression systems for producing polypeptides that are well know to those of ordinary skill in the art. (See, e.g., Gene Expression Systems, Fernandes and Hoeffler, Eds. Academic Press, 1999.) An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites, enhancers, operators, and the like are also optionally included. Constructs that include one or more of these control sequences are termed "expression cassettes." Accordingly, the nucleic acids that encode the joined polypeptides are incorporated for the desired level of expression in a desired host cell.

Expression control sequences that are suitable for use in a particular host cell are employed in the expression vectors. Commonly used prokaryotic control sequences, including promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) δ: 4057), the tac promoter (DeBoer, et al., Proc. Natl. Acad. Sci. U.S.A. (1983) 80:21-25); and the lambda-derived $P_L$ promoter and N-gene ribosome binding site (Shimatake et al., Nature (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, p15A-based vectors (Rose, Nucleic Acids Res. (1988) 16:355 and 356) and fusion expression systems such as GST and LacZ. Epitope tags can also be added to recombinant proteins to provide convenient methods of isolation, e.g., c-myc, HA-tag, 6-His (SEQ ID NO:21) tag, maltose binding protein, VSV-G tag, anti-DYKDDDDK (SEQ ID NO:22) tag, or any such tag, a large number of which are well known to those of skill in the art.

For expression of fusion polypeptides in prokaryotic cells other than E. coli, regulatory sequences for transcription and translation that function in the particular prokaryotic species are required. Such promoters can be obtained from genes that have been cloned from the species, or heterologous promoters can be used. For example, the hybrid trp-lac promoter functions in Bacillus in addition to E. coli. These and other suitable bacterial promoters are well known in the art and are described, e.g., in Sambrook et al. and Ausubel et al. Bacterial expression systems for expressing the proteins of the invention are available in, e.g., E. coli, Bacillus sp., and Salmonella (Palva et al., Gene 22:229-235 (1983); Mosbach et al., Nature 302:543-545 (1983). Kits for such expression systems are commercially available.

Similarly, for expression of the polypeptides of the invention in eukaryotic cells, transcription and translation sequences that function in the particular eukaryotic species are required. For example, eukaryotic expression systems for mammalian cells, yeast, and insect cells are well known in the art and are also commercially available. In yeast, vectors include pEFC, Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the concentration of heterologous protein in the host cell can be controlled. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in host bacterial cells, or able to integrate into the genome of host bacterial cells. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The polypeptides of the invention can be expressed and displayed on a cell or phage surface, or can be secreted from a cell. A variety of host cells can be used, including *E. coli*, other bacterial hosts, noted above, yeast cells, insect cells, fungal cells, and various mammalian cells such as the COS, CHO and HeLa cells lines and myeloma cell lines.

Once expressed, the recombinant polypeptides can be purified according to standard procedures of the art, e.g., using affinity columns, column chromatography, gel electrophoresis and the like (see, generally, R. Scopes, *Protein Purification*, Springer-Verlag, N.Y. (1982), Deutscher, *Methods in Enzymology Vol.* 182: *Guide to Protein Purification.*, Academic Press, Inc. N.Y. (1990)). Substantially pure compositions of at least about 90 to 95% homogeneity are preferred, and 98 to 99% or more homogeneity are most preferred.

To facilitate purification of the polypeptides of the invention, the nucleic acids that encode the polypeptides can also include a coding sequence for an epitope or "tag" for which an affinity binding reagent is available. Examples of suitable epitopes include the myc and V-5 responder genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

One of skill would recognize that modifications can be made to the protein domains without diminishing their biological activity. Some modifications may be made to facilitate the cloning, expression, or incorporation of a domain into a polypeptide. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

Display technologies have also permitted the selection of monoclonal antibodies that are fully human or other animal, chimeric, synthetic, and/or semi-synthetic. Examples of such display technologies are phage display (examples are disclosed in U.S. Pat. Nos. 5,821,047, 5,922,545, 5,403,484, 5,885,793, and 6,291,650) or yeast display (examples are disclosed in U.S. Pat. No. 6,300,065).

Antibody Libraries. Naïve libraries and Immunized libraries. Naïve libraries are made from the B-lymphocytes of a suitable host which has not been challenged with any immunogen, nor which is exhibiting symptoms of infection or inflammation. Immunized libraries are made a from a mixture of B-cells and plasma cells obtained from a suitably "immunized" host, i.e., a host that has been challenged with an immunogen. In one embodiment, the mRNA from these cells is translated into cDNA using methods well known in the art (e.g., oligo-dT primers and reverse transcriptase). In an alternative embodiment, nucleic acids encoding antibodies from the host cells (mRNA or genomic DNA) are amplified by PCR with suitable primers. Primers for such antibody gene amplifications are well known in the art (e.g., U.S. Pat. No. 6,096,551 and PCT Patent Application WO 00/70023A1 disclose such primers). In a hybrid embodiment, the mRNA from the host cells is synthesized into cDNA and these cDNAs are then amplified in a PCR reaction with antibody specific primers (e.g., U.S. Pat. No. 6,319,690 discloses such a hybrid method). Alternatively, the repertoires may be cloned by conventional cDNA cloning technology (Sambrook and Russell, eds, *Molecular Cloning: A Laboratory*

*Manual,* 3rd Ed, vols. 1-3, Cold Spring Harbor Laboratory Press, 2001), without using PCR.

The invention will be further understood by the following non-limiting examples.

EXAMPLES

Example 1

Construction of Epitope-Focused Libraries of Antibody Fragments by In Vitro Transcription Messenger RNA encoding an antibody repertoire is isolated from Ig-producing cells of the human immune system. One unit of whole blood is drawn from a human donor and a buffy coat preparation is made using standard procedures. Peripheral blood mononuclear cells (PBMCs) are purified by Ficoll-Hypaque density centrifugation to enrich for Ig-producing B lymphocytes. Total RNA is purified from the PBMCs using a commercially available RNA purification kit (Qiagen RNeasy) used according to the manufacturer's specifications. mRNA is enriched from the total RNA using a commercially available RNA purification kit (Qiagen Oligotex mRNA kit) used according to the manufacturer's specifications. The mRNA from several donors of different ethnic backgrounds is pooled to increase the diversity of the final V segment repertoires. Additional diversity can be obtained from human spleen mRNA obtained from either a human donor or from a commercial source.

Sets of oligonucleotide primers were designed to 5' and 3' regions of the V regions for cloning the V region repertoire. Three primer sets are used to ensure that immunoglobulin variable regions are amplified exclusively from all other expressed mRNAs. Some primers in each set are degenerate at one or more positions in order to capture the sequence diversity present in the immunoglobulin genes. Most of the primer sequences described here have been previously published (Welschof et al., *J. Immunological Methods,* 179: 203-214 [1995] and Little et al., *J. Immunological Methods,* 231: 3-9 [1999]) and some have been modified for use in this work.

```
1st Primer Set:
                                        (SEQ ID NO: 23)
Vkappa (Vκ): [P]GAAGACAGATGGTGCAGCCACAG (SEQ ID NO: 24)
Vlambda (Vλ): [P]AGAGGASGGYGGGAACAGAGTGAC (SEQ ID NO: 25)
Vheavy (Vh) IgG: [P]GACSGATGGGCCCTTGGTGGA (SEQ ID NO: 26)
Vh IgM: [P]AAGGGTTGGGGCGGATGCACT 2nd Primer Set:
VκI:
                                        (SEQ ID NO: 27)
CATGTGTAATACGACTCACTATAGGGAGTCATACATCACCATGGGCGCG
CTGGACATCCAGWTGACCCAGTCTCC VκII:
                                        (SEQ ID NO: 28)
CATGTGTAATACGACTCACTATAGGGAGTCATACATCACCATGGGCGCG
CTGGATGTTGTGATGACTCAGTCTCC VκIII:
                                        (SEQ ID NO: 29)
CATGTGTAATACGACTCACTATAGGGAGTCATACATCACCATGGGCGCG
CTGGAAATTGTGWTGACRCAGTCTCC
```

-continued
```
VκIV:
                                        (SEQ ID NO: 30)
CATGTGTAATACGACTCACTATAGGGAGTCATACATCACCATGGGCGCG
CTGGATATTGTGATGACCCACACTCC VκV:
                                        (SEQ ID NO: 31)
CATGTGTAATACGACTCACTATAGGGAGTCATACATCACCATGGGCGCG
CTGGAAACGACACTCACGCAGTCTCC VκVI:
                                        (SEQ ID NO: 32)
CATGTGTAATACGACTCACTATAGGGAGTCATACATCACCATGGGCGCG
CTGGAAATTGTGCTGACTCAGTCTCC Vλ1a:
                                        (SEQ ID NO: 33)
CATGTGTAATACGACTCACTATAGGGAGTCATACATCACCATGGGCGCG
CTGCAGTCTGTGCTGACTCAGCCACC Vλ1b:
                                        (SEQ ID NO: 34)
CATGTGTAATACGACTCACTATAGGGAGTCATACATCACCATGGGCGCG
CTGCAGTCTGTGYTGACGCAGCCGCC Vλ1c:
                                        (SEQ ID NO: 35)
CATGTGTAATACGACTCACTATAGGGAGTCATACATCACCATGGGCGCG
CTGCAGTCTGTCGTGACGCAGCCGCC Vλ2:
                                        (SEQ ID NO: 36)
CATGTGTAATACGACTCACTATAGGGAGTCATACATCACCATGGGCGCG
CTGCARTCTGCCCTGACTCAGCCT Vλ3a:
                                        (SEQ ID NO: 37)
CATGTGTAATACGACTCACTATAGGGAGTCATACATCACCATGGGCGCG
CTGTCCTATGWGCTGACTCAGCCACC Vλ3b:
                                        (SEQ ID NO: 38)
CATGTGTAATACGACTCACTATAGGGAGTCATACATCACCATGGGCGCG
CTGTCTTCTGAGCTGACTCAGGACCC Vλ4:
                                        (SEQ ID NO: 39)
CATGTGTAATACGACTCACTATAGGGAGTCATACATCACCATGGGCGCG
CTGCACGTTATACTGACTCAACCGCC Vλ5:
                                        (SEQ ID NO: 40)
CATGTGTAATACGACTCACTATAGGGAGTCATACATCACCATGGGCGCG
CTGCAGGCTGTGCTGACTCAGCCGTC Vλ6:
                                        (SEQ ID NO: 41)
CATGTGTAATACGACTCACTATAGGGAGTCATACATCACCATGGGCGCG
CTGAATTTTATGCTGACTCAGCCCCA Vλ7 and Vλ8:
                                        (SEQ ID NO: 42)
CATGTGTAATACGACTCACTATAGGGAGTCATACATCACCATGGGCGCG
CTGCAGRCTGTGGTGACYCAGGAGCC Vλ9:
                                        (SEQ ID NO: 43)
CATGTGTAATACGACTCACTATAGGGAGTCATACATCACCATGGGCGCG
CTGCWGCCTGTGCTGACTCAGCCMCC Vh1b and Vh7:
                                        (SEQ ID NO: 44)
CATGTGTAATACGACTCACTATAGGGAGTCATACATCAGGCCCAGCCGG
CCATGGCTCAGRTGCAGCTGGTGCARTCTGG Vh1c:
                                        (SEQ ID NO: 45)
CATGTGTAATACGACTCACTATAGGGAGTCATACATCAGGCCCAGCCGG
CCATGGCTSAGGTCCAGCTGGTRCAGTCTGG
```

```
Vh2:
                                       (SEQ ID NO: 46)
CATGTGTAATACGACTCACTATAGGGAGTCATACATCAGGCCCAGCCGG
CCATGGCTCAGRTCACCTTGAAGGAGTCTGG

Vh3b:
                                       (SEQ ID NO: 47)
CATGTGTAATACGACTCACTATAGGGAGTCATACATCAGGCCCAGCCGG
CCATGGCTSAGGTGCAGCTGGTGGAGTCTGG

Vh3c:
                                       (SEQ ID NO: 48)
CATGTGTAATACGACTCACTATAGGGAGTCATACATCAGGCCCAGCCGG
CCATGGCTGAGGTGCAGCTGGTGGAGWCYGG

Vh4b:
                                       (SEQ ID NO: 49)
CATGTGTAATACGACTCACTATAGGGAGTCATACATCAGGCCCAGCCGG
CCATGGCTCAGGTGCAGCTACAGCAGTGGGG

Vh4c:
                                       (SEQ ID NO: 50)
CATGTGTAATACGACTCACTATAGGGAGTCATACATCAGGCCCAGCCGG
CCATGGCTCAGSTGCAGCTGCAGGAGTCSGG

Vh5:
                                       (SEQ ID NO: 51)
CATGTGTAATACGACTCACTATAGGGAGTCATACATCAGGCCCAGCCGG
CCATGGCTGARGTGCAGCTGGTGCAGTCTGG

Vh6:
                                       (SEQ ID NO: 52)
CATGTGTAATACGACTCACTATAGGGAGTCATACATCAGGCCCAGCCGG
CCATGGCTCAGGTACAGCTGCAGCAGTCAGG

3rd Primer Set:
Jκ1 and Jκ2 and Jκ4:
                                       (SEQ ID NO: 53)
TATAGCGGCCGCACTAGTTCGTTTGATRTCCASCTTGGTCC Jκ3:
                                       (SEQ ID NO: 54)
TATAGCGGCCGCAGTAGTTCGTTTGATATCCACTTTGGTCC Jκ5:
                                       (SEQ ID NO: 55)
TATAGCGGCCGCACTAGTTCGTTTAATCTCCAGTCGTGTCC Jλ1:
                                       (SEQ ID NO: 56)
TATAGCGGCCGCCCTAGGCTGCCYAAGGACGGTGACCTTGGTCC Jλ2 and Jλ3:
                                       (SEQ ID NO: 57)
TATAGCGGCCGCCCTAGGCTGCCYAAGGACGGTCAGCTTGGTCC Jλ7:
                                       (SEQ ID NO: 58)
TATAGCGGCCGCCCTAGGCTGCCYGAGGACGGTCAGCTGGGTGC JH1 and JH2:
                                       (SEQ ID NO: 59)
GCGGATGCACTTCCGGAGGAGACGGTGACCAGGGTGCC JH3:
                                       (SEQ ID NO: 60)
GCGGATGCACTTCCGGAAGAGACGGTGACCATTGTCCC JH4 and JH5:
                                       (SEQ ID NO: 61)
GCGGATGCACTTCCGGAGGAGACGGTGACCAGGGTTCC JH6:
                                       (SEQ ID NO: 62)
GCGGATGCACTTCCGGAGGAGACGGTGACCGTGGTCCC
```

The primer sets are designed to be pooled and to be used in individual reactions for Vh, Vκ or Vλ. The first primer (for Vκ or Vλ) or primer set (for Vh IgM and Vh IgG) is annealed to the 'constant' region of the immunoglobulin-encoding mRNAs. Each primer of the first primer set is phosphorylated at the 5' end for subsequent digestion with lambda exonuclease. First strand cDNA is synthesized by reverse transcriptase using standard procedures. The mRNA is digested from the first-strand cDNA with a cocktail of RNase H and RNase A. A second primer set is annealed to N-terminal end of the V regions of the first strand cDNA. Each primer in the second set contains a T7 RNA polymerase promoter, a restriction site not (or rarely) present in the cDNA repertoire and a region complementary to the cDNA (positions 1-8 for Vh, Vκ and Vλ according to the Kabat numbering scheme). Second strand cDNA is synthesized by standard procedures. Lambda exonuclease is used to degrade the first strand cDNA. A third primer set is annealed to the C-terminal end of the V region (in the same orientation but nested upstream of the first primer set) of the second strand cDNA. Each primer in the third set contains restriction site not (or rarely) present in the cDNA repertoire and a region complementary to the cDNA (positions 107-114 for Vh, positions 101 to 108 for Vλ and positions 101 to 108 for Vλ according to the Kabat numbering scheme). The annealed third set primers are extended by DNA polymerase, and the antisense strand cDNA is synthesized.

The double stranded cDNA is added to an in vitro transcription reaction that includes NTPs and T7 RNA polymerase. The T7 promoter appended to the second primer set drives the synthesis of sense strand cRNA. The fold-amplification is estimated to be >500. To obtain enough cDNA for subsequent cloning, the cRNA is converted to ds cDNA by priming first and second strand cDNA synthesis with primer sets three and two, respectively, using well-known procedures for synthesis. The resulting ds cDNA is added to an IVT reaction in order to synthesize additional cRNA. The additional amplification step can be repeated as many times as necessary to generate a sufficient quantity of cRNA for cloning, usually about 500 ng to 1 µg.

When a sufficient quantity of cRNA has been synthesized, it is converted to ds cDNA by routine procedures and cut with the restriction enzymes for which sites have been appended by inclusion in the primer sequence. The restriction enzyme sites for Vh are Sfi I or Nco I and Bsp EI, for Vk Bss HII and Spe I, and for Vl Bss HII and Avr II. The restricted cDNA repertoire is ligated into an appropriate cloning vector and transformed into $E. coli$. We estimate that $\geq 10^7$ transformants for VH and $\geq 10^6$ transformants for VL are sufficient to represent the variable region diversity in one individual. Typically, the immunoglobulin repertoire from several individuals is combined into a single library.

Human antibodies with the specificity of the mouse Mab 166 (U.S. Pat. No. 6,827,935), against an epitope on $Pseudomonas\ aeruginosa$ PcrV protein, were generated as follows. A V segment consists of the region from FR1 to FR3 (positions 1 to 94 for Vh, positions 1 to 88 for Vκ and positions 1 to 88 for Vl using the Kabat numbering scheme) and lacks a CDR3 and FR4. The M166 reference antibody CDR3-FR4 regions for both the Vh and the Vκ chains was appended to the V segment library as described below.

A library of V segments (BA19) was derived from the V region cRNA. An antisense primer was designed to Kabat positions 86 to 89 for Vh, Kabat positions 80 to 84 for Vκ and Kabat positions 81 to 85 for Vλ. The primer sequences are shown below. In order to capture as many gene variants as possible, degeneracy is added to primer positions in which the germ-line repertoire varies.

Vh:
CACAGTAGTATACGGCCGTGTC    (SEQ ID NO: 63)
CACAGTAGTATACRGCNGTGTC    (SEQ ID NO: 64)
CACAGTAGTATACGGCCGTCTC    (SEQ ID NO: 65)

Vκ:
CAAATGTATACTGCMAMATCTTCAG    (SEQ ID NO: 66)
TTCAAATGTATACTGCAATATCTTCAG    (SEQ ID NO: 67)
TTCAAATGTATACYCCRACATCCTCAG    (SEQ ID NO: 68)
TTCAAATGTATACTGCAGCATCTTCAG    (SEQ ID NO: 69)

Vλ:
TTGTAAAGATATCRGCYTCRTCYHYNC    (SEQ ID NO: 70)
GTAAAGATATCRGCCTCRTCBTYHG    (SEQ ID NO: 71)

A non-templated Bst1107I (for Vh and Vκ) or Eco RV (for Vλ) restriction site is appended to the 5' end of the primer for subsequent cloning of the V segment repertoire. The primer is hybridized to the cRNA population and is extended during first strand cDNA synthesis. The second strand cDNA is synthesized using standard protocols.

The Vh segment cDNA is restricted with Sfi I and Bst1107 I and is cloned upstream of the CDR3-FR4 region of the M166 reference Vh chain to create recombinant Vh regions in which the V segment repertoire is attached to a single CDR3-FR4 region. The sequence of the CDR3-FR4 region of the M166 Vh chains, modified to include a Bst1107 I restriction site at its 5' end and a BspE I site at its 3' end, is shown below.

M166 Vh CDR3-FR4:
(SEQ ID NO: 72)
GTATACTACTGTGCCAGAAATAGAGGGGATATTTACTATGATTTCACTT

ATGCCATGGACTACTGGGGTCAAGGAACCTCAGTCACCGTCTCCTCCGG

A

The Vκ segment cDNA is restricted with Bss HII and Bst1107 I and is cloned upstream of the CDR3-FR4 region of the M166 reference Vκ chain to create recombinant Vκ regions in which the V segment repertoire is attached to a single CDR3-FR4 region. The sequence of the CDR3-FR4 region of the M166 Vκ chains, modified to include a Bst1107 I restriction site at its 5' end and a Spe I site at its 3' end, is shown below.

M166 Vκ CDR3-FR4:
(SEQ ID NO: 73)
GTATACTACTGTCAACATTTTTGGAGTACTCCGTACACGTTCGGAGGGG

GGACCAAGCTGGAAATAAAACGAACTAGT

To construct the library BA46, the CDR3-FR4 region was appended to the V segment libraries by primer extension. An antisense oligonucleotide containing the sequence of CDR3-FR4 region of the M166 reference antibody Vh chain was synthesized by standard procedures. In addition to the CDR3-FR4 region, nucleotides encoding the highly conserved YYCAR (SEQ ID NO:74) sequence in human FR3 (Kabat positions 90 to 94) were included at the 3' end of the oligonucleotide and a restriction site for cloning, BspE I, was added to the 5' end. The sequence of the oligonucleotide is shown below.

M166 Vh CDR3-FR4:
(SEQ ID NO: 75)
TAGATCCGGAGGAGACGGTGACTGAGGTTCCTTGACCCCAGTAGTCCAT

GGCATAAGTGAAATCATAGTAAATATCCCCTCTATTTCTGGCACAGTAA

TA

The oligonucleotide was hybridized to the Vh region library cRNA previously described. First strand synthesis was accomplished with reverse transcriptase using standard procedures. The template cRNA was removed with a cocktail of RNase H and RNase A. The second strand cDNA was synthesized using standard procedures.

The Vκ segment library was appended to the M166 CDR3-FR4 region in a similar fashion. An antisense oligonucleotide containing the sequence of CDR3-FR4 region of the M166 reference antibody Vκ chain was synthesized by standard procedures. In addition to the CDR3-FR4 region, nucleotides encoding the highly conserved YYC sequence in human FR3 (Kabat positions 86 to 88) was included at the 3' end of the oligonucleotide and a restriction site for cloning, Spe I, was added to the 5' end. The sequence of the oligonucleotide is shown below. The oligonucleotide is degenerate at three positions in order to capture the sequence diversity present in the germ-line immunoglobulin mRNA.

M166 Vκ CDR3-FR4:
(SEQ ID NO: 76)
CGAATTGAACTAGTTCGTTTTATTTCCAGCTTGGTCCCCCCTCCGAACG

TGTACGGAGTACTCCAAAAATGTTGRCARTARTA

The oligonucleotide was hybridized to the Vκ region library cRNA previously described. First strand synthesis was accomplished with reverse transcriptase using standard procedures. The template cRNA was removed with a cocktail of RNase H and RNase A. The second strand cDNA was synthesized using standard procedures.

V region libraries created by either of the above methods are cloned into a Fab expression vector for generating secreted assembled Fab fragments to be screened for antigen binding. The full, in-frame Vh region library is restricted with Sfi I and Bsp EI and is inserted into a Fab expression vector such as KB1082, which is shown in FIG. 1. The complete nucleotide sequence is shown in FIG. 2. The full Vκ region is restricted with BssH II and Spe I and is inserted into the same vector that contains the Vh region library. Alternatively, a similar vector can be constructed that contains a Clambda instead of a Ckappa constant region and can be used for the expression of Vλ V-regions. The Fab expression vector comprises an antibiotic resistance gene for selection in E. coli, a dicistronic expression cassette driven by an inducible promoter (such as PBAD), VH and VL constant regions and cloning sites for the VH region and VL region repertoires.

Fabs expressed from plasmid KB1082 were screened by a colony-lift binding assay (CLBA) as described in Examples 5 and 6 or pools of colonies were screened and subsequently de-convoluted using an antigen-binding ELISA as described in Example 6.

Example 2

Construction of Epitope-Focused Libraries of Antibody Fragments by PCR

For PCR-mediated amplification and cloning of antibody repertoires, two primer sets are used. The sense primer-set anneals to the N-terminal region (positions 1-8 for Vh, Vκ and Vλ according to the Kabat numbering scheme) of the V segment and contains a restriction site(s) appended to the 5' end (in this case Sfi I and Nco I) suitable for use in cloning into a plasmid vector. The anti-sense primer-set anneals to the C-terminal end of framework three (FR3; positions 86 to 90 for Vh, positions 80 to 86 for Vκ and positions 81 to 86 for Vλ according to the Kabat numbering scheme). All of the antisense primers include an invariant nucleotide sequence for the YYC peptide (Kabat positions 90 to 92 for Vh, 86 to 88 for Vκ and Vλ. Each antisense primer includes a restriction site appended to the 5' end (in this case Sal I) suitable for use in cloning into a plasmid vector. Some primers in each set are degenerate at one or more positions in order to capture the sequence diversity present in the germ-line immunoglobulin mRNA.

```
Sense Primer Sets:
Vκ:
VκI:
                                            (SEQ ID NO: 77)
CAGCCGGCCATGGCCGCGCTGGACATCCAGWTGACCCAGTCTCC
VκII:
                                            (SEQ ID NO: 78)
CAGCCGGCCATGGCCGCGCTGGATGTTGTGATGACTCAGTCTCC
VκIII:
                                            (SEQ ID NO: 79)
CAGCCGGCCATGGCCGCGCTGGAAATTGTGWTGACRCAGTCTCC
VκIV:
                                            (SEQ ID NO: 80)
CAGCCGGCCATGGCCGCGCTGGATATTGTGATGACCCAGTCTCC
VκV:
                                            (SEQ ID NO: 81)
CAGCCGGCCATGGCCGCGCTGGAAACGACACTCACGCAGTCTCC
VκVI:
                                            (SEQ ID NO: 82)
CAGCCGGCCATGGCCGCGCTGGAAATTGTGCTGACTCAGTCTCC Vλ:
Vλ1a:
                                            (SEQ ID NO: 83)
CATGTATCAGCGCGCTGCAGTCTGTGCTGACTCAGCCACC
Vλ1b:
                                            (SEQ ID NO: 84)
CATGTATCAGCGCGCTGCAGTCTGTGYTGACGCAGCCGCC
Vλ1c:
                                            (SEQ ID NO: 85)
CATGTATCAGCGCGCTGCAGTCTGTCGTGACGCAGCCGCC
Vλ2:
                                            (SEQ ID NO: 86)
CATGTATCAGCGCGCTGCARTCTGCCCTGACTCAGCCT
Vλ3a:
                                            (SEQ ID NO: 87)
CATGTATCAGCGCGCTGTCCTATGWGCTGACTCAGCCACC
Vλ3b:
                                            (SEQ ID NO: 88)
CATGTATCAGCGCGCTGTCTTCTGAGCTGACTCAGGACCC
Vλ4:
                                            (SEQ ID NO: 89)
CATGTATCAGCGCGCTGCACGTTATACTGACTCAACCGCC
Vλ5:
                                            (SEQ ID NO: 90)
CATGTATCAGCGCGCTGCAGGCTGTGCTGACTCAGCCGTC
Vλ6:
                                            (SEQ ID NO: 91)
CATGTATCAGCGCGCTGAATTTTATGCTGACTCAGCCCCA
Vλ7 and Vλ8:
                                            (SEQ ID NO: 92)
CATGTATCAGCGCGCTGCAGRCTGTGGTGACYCAGGAGCC
Vλ9:
                                            (SEQ ID NO: 93)
CATGTATCAGCGCGCTGCWGCCTGTGCTGACTCAGCCMCC
Vλ10:
                                            (SEQ ID NO: 94)
CATGTATCAGCGCGCTGCAGGCAGGGCTGACTCAGCCACC Vh:
Vh1b and Vh7:
                                            (SEQ ID NO: 95)
GCCCAGCCGGCCATGGCTCAGRTCAGCTGGTGCARTCTGG
Vh1c:
                                            (SEQ ID NO: 96)
GCCCAGCCGGCCATGGCTSAGGTCCAGCTGGTRCAGTCTGG
Vh2:
                                            (SEQ ID NO: 97)
GCCCAGCCGGCCATGGCTCAGRTCACCTTGAAGGAGTCTGG
Vh3b:
                                            (SEQ ID NO: 98)
GCCCAGCCGGCCATGGCTSAGGTGCAGCTGGTGGAGTCTGG
Vh3c:
                                            (SEQ ID NO: 99)
GCCCAGCCGGCCATGGCTGAGGTGCAGCTGGTGGAGWCYGG
Vh4b:
                                            (SEQ ID NO: 100)
GCCCAGCCGGCCATGGCTCAGGTGCAGCTACAGCAGTGGGG
Vh4c:
                                            (SEQ ID NO: 101)
GCCCAGCCGGCCATGGCTCAGSTGCAGCTGCAGGAGTCSGG
Vh5:
                                            (SEQ ID NO: 102)
GCCCAGCCGGCCATGGCTGARGTGCAGCTGGTGCAGTCTGG
Vh6:
                                            (SEQ ID NO: 103)
GCCCAGCCGGCCATGGCTCAGGTACAGCTGCAGCAGTCAGG Antisense Primer Sets:
Vκ:
VκI:
                                            (SEQ ID NO: 104)
CAGATAATGTCGACTGGCAGTAGTAAGTTGCAAAATCTTCAG
                                            (SEQ ID NO: 105)
CAGATAATGTCGACTGGCAGTAGTATGTTGCAAYATCTTCAG
VκII:
                                            (SEQ ID NO: 106)
CAGATAATGTCGACTGGCAGTAGTAAACYCCRACATCCTCAG
VκIII:
                                            (SEQ ID NO: 107)
CAGATAATGTCGACTGGCAGTAGTAMACTGCAAAATCTTCAG
VκIV:
                                            (SEQ ID NO: 108)
CAGATAATGTCGACTGGCAGTAGTAAACAGCCACATCTTCAG
VκV:
                                            (SEQ ID NO: 109)
CAGATAATGTCGACTGGCAGAAGTAGTATGCAGCATCCTCAG
VκVI:
                                            (SEQ ID NO: 110)
CAGATAATGTCGACTGGCAGTAGTAYGTTGCAGCATCTTCAG Vλ:
Vλ1, Vλ2, Vλ3, Vλ4, Vλ5, Vλ6, Vλ7 and Vλ10:
                                            (SEQ ID NO: 111)
CAGATAATGTCGACTGGCAGTAGTARTCRGCCTCRTCCTC
Vλ1 and Vλ3:
                                            (SEQ ID NO: 112)
CAGATAATGTCGACTGGCAGTAGTAGTCRGCCTCRTCYCC
Vλ4c:
                                            (SEQ ID NO: 113)
CAGATAATGTCGACTGGCAGTGGTACTCAGCCTCATCGTC
Vλ8:
                                            (SEQ ID NO: 114)
CAGATAATGTCGACTGGCAGTAGTAATCAGATTCATCATC
Vλ9:
                                            (SEQ ID NO: 115)
CAGATAATGTCGACTGGCAGTGGTAGTCACTCTCATCCTC Vh:
Vh1, Vh3, Vh4 and Vh6:
                                            (SEQ ID NO: 116)
CAGATAATGTCGACGTGCGCAGTAGTACACRGCYGTGTC
Vh2:
                                            (SEQ ID NO: 117)
CAGATAATGTCGACGTGCGCAGTAGTAYGTGGCTGTGTC
Vh5:
                                            (SEQ ID NO: 118)
CAGATAATGTCGACGTGCGCAGTAGTACATGGCGGTGTC
Vh7:
                                            (SEQ ID NO: 119)
CAGATAATGTCGACGTGCGCAGTAGTACACGGCAGTGTC
```

First-strand cDNA is prepared from the mRNA of peripheral blood lymphocytes or spleen with a polydT primer and reverse transcriptase according to established procedures. A cocktail of RNase H and RNase A is used to remove the mRNA from the first strand cDNA. After purification to remove the primer and dNTPs, the first strand cDNA is used as a template for PCR.

PCR reactions are assembled with up- and downstream primers such that members of a particular V segment subclass (e.g., Vh2 excluding Vh1, Vh3, Vh4, Vh5, Vh6 and Vh7) will be amplified exclusively. Fifty µl reactions are assembled containing 50 nM sense primer, 50 nM antisense primer, ~50 ng first-strand cDNA, 100 µM of each dNTP, buffer and Taq polymerase. The reactions are cycled with the following parameters: 95° C. for 5 min—[94° C. for 10 sec; 55° C. for 1 min; 72° C. for 30 sec]$_{25-35}$—72° C. for 5 min. The PCR products are purified away from the primers and nucleotides by passage through a DNA purification column (Qiagen Qiaquick) used according to the manufacturer's specifications.

The full VH or VL repertoires, comprising all of the VH or VL subclasses, can be reconstituted by mixing the desired ratios of the subclass specific PCR products. The desired ratio of each subclass can reflect the incidence of each subclass in the germ-line, can mirror subclass usage in vivo (for example see Sheets et al. *Proc. Natl. Acad. Sci.* 95: 6157-6162 [1998])), or can be an arbitrary ratio. The PCR products are restricted with NcoI and SalI and cloned into a plasmid vector. In a preferred embodiment, the plasmid vector has a T7 RNA polymerase promoter immediately upstream of the V segment insert in order to drive the synthesis of single-stranded cRNA representing the V segment repertoire.

The V segment repertoire can be attached to a CDR3-FR4 region by one of many schemes that include ligation of restricted DNA, overlap extension PCR or primer-directed cDNA synthesis.

In a preferred embodiment, an oligonucleotide corresponding to CDR3-FR4 of the reference antibody is synthesized by standard procedures and is appended to the V segment library. An antisense oligonucleotide containing the M166 Vh CDR3-FR4 sequence was synthesized and its sequence is shown below. A single amino acid change was made in FR4 to make it identical to the FR4 sequence encoded by the human germ-line JH6-segment. A sequence complementary to the YYCAR (SEQ ID NO:74) region of the V segment library (Kabat positions 90 to 94) is included at the 3' end of the oligonucleotide. Additionally, a Bsp EI restriction site useful for cloning is appended to the 5' end of the oligonucleotide.

M166 Vh CDR3-Human FR4 oligonucleotide:
(SEQ ID NO: 120)
CTGTTCCGGAGCTGACGGTGACTGTGGTTCCTTGACCCCAGTAATCCAT

CGCATAGGTGAAATCATAGTAAATATCACCACGGTTACGTGCGCAGTAG

TA

The oligonucleotide is annealed to the 3' ends of the Vh segment cRNA repertoire via the nucleotide sequence coding for the YYCAR (SEQ ID NO:74) peptide and is extended by reverse transcriptase using standard protocols. A cocktail of RNase A and RNase H is used to degrade the template cRNA and second strand cDNA is synthesized according to established procedures.

An antisense oligonucleotide containing the M166 Vκ CDR3-FR4 sequence was synthesized and is shown below. A single amino acid change was made in FR4 to make it identical to the FR4 sequence encoded by human germ-line ha. A sequence complementary to the YYC region of the V segment library (Kabat positions 86 to 88) is included at the 3' end of the oligonucleotide. Additionally, a Spe I restriction site useful for cloning is appended to the 5' end of the oligonucleotide.

M166 VK CDR3-Human FR4 oligonucleotide:
(SEQ ID NO: 121)
ATTGAACTAGTTCGTTTTATTTCCAGCTTGGTCCCCTGTCCGAACGTGT

ACGGAGTACTCCAAAAATGCTGGCAGTAGTA

The oligonucleotide is annealed to the 3' ends of the Vκ segment cRNA repertoire via the nucleotide sequence coding for the YYC peptide and is extended by reverse transcriptase using standard protocols. A cocktail of RNase A and RNase H is used to degrade the template cRNA and second strand cDNA is synthesized according to established procedures.

Figure 3:
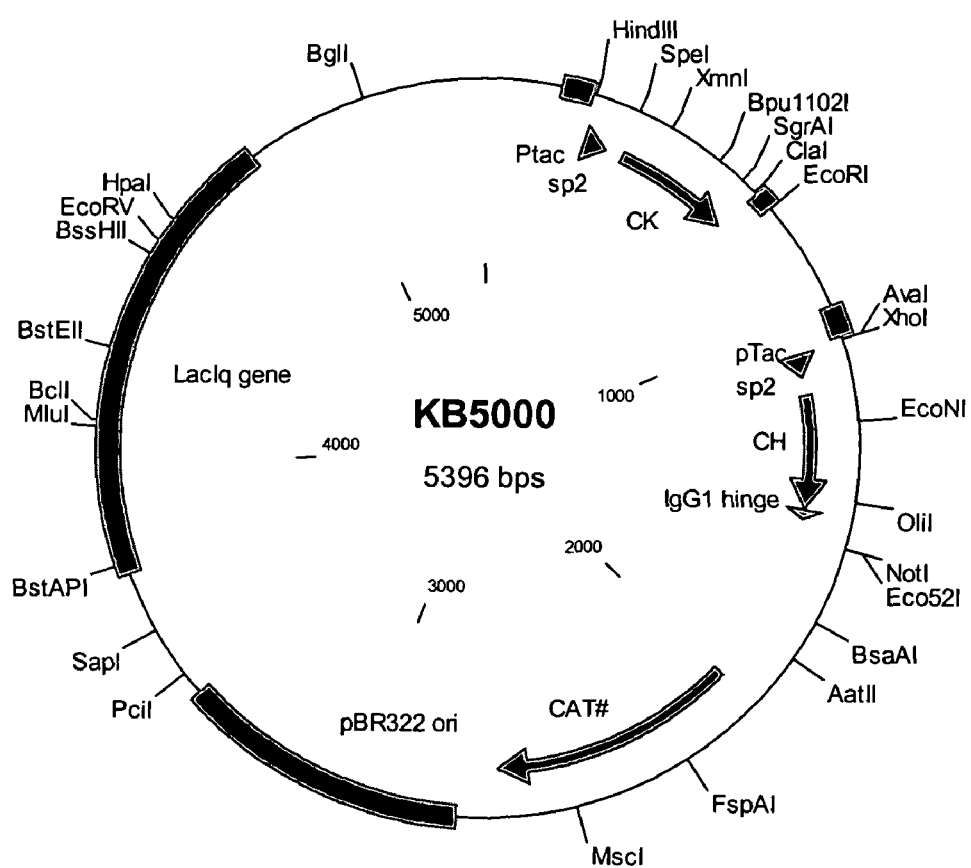
FIG. 3 shows a vector for the expression of Fab' fragments in E. coli. Plasmid KB5000 has two IPTG-inducible tac promoters for expression of a human kappa chain and a human heavy chain Fd' fragment.

The resulting Vh and Vk region cDNAs are restricted with enzymes for which sites have been appended to each primer or primer set. The Vh and Vκ regions are cloned into an appropriate vector for expression of Fab' fragments in *E. coli*, such as KB1150 described below (FIG. 3 and FIG. 4). The Fab' library constructed in KB1150 was designated BA110.

The KB1150 vector is comprised of the following elements. 1. A chloramphenicol resistance gene for selection in *E. coli*. 2. A monocistronic cassette for VH-CH driven by the pTac promoter that contains a synthetic peptide leader sequence for secretion of the polypeptide chain into the media. 3. A monocistronic cassette for VL-CL driven by the pTac promoter that contains a synthetic peptide leader sequence for secretion of the polypeptide chain into the media. The vector KB1150 contains the Cκ constant region, however, a vector with the Cλ constant region can be constructed for the expression of Vλ V-regions. 4. An IgG1 hinge region for promoting Fab' production in *E. coli*. 5. A Myc peptide tag for detection and purification. 6. Suitable restriction sites for inserting the VH and VL regions. 7. The lac Iq gene which acts to repress the pTac promoter in the absence of the inducer IPTG.

Antibody Fab expression vector KB1150 was derived from pGEX-4T-1 (Amersham Biosciences), in which the ampicillin resistance gene is replaced by a chloramphenicol resistance gene. It contains two separate pTac expression cassettes separated by a T7 terminator. The upstream pTac promoter is used to express the light chain and the downstream pTac promoter is used to express the heavy chain. The VL-CL cassette is preceded by a novel secretion signal peptide SP2: MGKKQLVVFALLLAFLSPAMA (SEQ ID NO:20). The VH-CH cassette is also preceded by the secretion signal peptide SP2. The VH-CH contains the hinge region of IgG 1 (THTCPPCPA; SEQ ID NO:122) and a Myc tag peptide (GAAEQKLISEEDLN; SEQ ID NO:123) at the end of heavy chain C region. The lac Iq gene represses the pTac promoter in the absence of the inducer IPTG.

Antibody fragments secreted from plasmid KB1150 are screened by CLBA or ELISA as described in Examples 5 and 6.

Example 3

Identification of Human Anti-PcrV Antibodies Containing a MEBSD from a Murine Antibody CDRH3 Region The HCDR3 typically consists of amino acids from the D region, the J region and N-additions (amino acids encoded by nucleotides added during in vivo recombination). The LCDR3 consists of amino acids from the V region, J region and N-additions. The Minimal Essential Binding Specificity Determinant (MEBSD) can be all or part of a CDR3. Libraries of antibodies can be constructed by attaching V segment libraries onto the MEBSD derived from an HCDR3 or an LCDR3.

In order to determine whether a D-segment with associated N-additions could define a MEBSD, the CDRH3 region of murine antibody M166 was analyzed to identify the D-segment and any associated N-additions (see FIG. 5). The M166 HCDR3 was compared to all identified murine germ-line D segments. The closest sequence similarity for the D region is to murine D segment D-SP2.2. The N additions are represented by two amino acids upstream and two amino acids downstream of the D region. The M166 J region is most similar to the human JH6 and JH3 variants.

V region repertoires combining the putative M166 MEBSD and a human JH6 or JH3 sequence were constructed in a Fab' expression vector and the Fab's were tested for binding to PcrV in a colony-lift binding assay. Antisense primers encoding the germ-line JH6 or JH3 region were synthesized and are shown below. The first four tyrosines (Y) of human JH6 were not included in the Antisense Primer JH6 as there is no amino-acid in these positions in the M166 CDRH3 region. One tyrosine was added to the human JH3 of Antisense Primer JH3 in order to preserve the length of the M166 CDR3. A sense primer for the Vh3 subclass family was also prepared.

```
Antisense Primer JH6:
                                  (SEQ ID NO: 124)
CTGTTCCGGAGCTGACGGTGACTGTGGTTCCTTGACCCCAGACATCCAT

GCCATAGGTGAAATC

Antisense Primer JH3:
                                  (SEQ ID NO: 125)
CTGTTCCGGAGCTGACGGTGACCATTGTTCCTTGACCCCAAATATCGAA

CGCATAGGTGAAATC

Sense Primer Vh3b:
                                  (SEQ ID NO: 126)
GCCCAGCCGGCCATGGCTSAGGTGCAGCTGGTGGAGTCTGG
```

A Vh region library containing the M166 CDR3-FR4 region was PCR-amplified with an N-terminal sense primer for the Vh3 family and either Antisense Primer JH6 or Antisense Primer JH3. After amplification, most Fab' molecules in each library contained the FR4 amino acid sequence encoded by the antisense primers. Some of the Vh regions were Vh1 instead of Vh3, due to cross-hybridization of the Vh3 5' primer to Vh1 segment ends.

The Vh region repertoire was restricted with Nco I and Bsp EI and cloned into the Fab' expression vector KB1150. The VL repertoire comprised pre-selected human Vk chains (appended to the M166 CDR3-FR4 region) that were known to bind PcrV in an ELISA assay when paired with a compatible Vh region. Approximately 3500 members of the resulting Fab' libraries were tested in a CLBA assay in which 20 uM IPTG was used to induce Fab' expression (as described in Example 6).

Of the ~3500 cloned Fab's that contain the BSD and a FR4 containing human JH6 sequence, 34 were positive in the CLBA assay, indicating that these Fab' clones could bind the PcrV antigen. Individual clones were isolated and soluble Fab' was enriched from the growth media. Each of the purified Fab's was positive in an ELISA specific for PcrV antigen. The amino acid sequence of the Vh and Vk regions from two of the positive clones is shown in FIG. 6. The MEBSD sequence, comprising the M166 Vh D-region with N-additions, is marked.

Remarkably, both antibody BA130-5-E10 and BA130-1-1D have VH segments which are identical to human germ-line sequence over the entire region spanning FR1-CDR1-FR2-CDR2-FR3. The germ-line gene Vh1-69 is used in antibody BA130-1-1D and germ-line gene Vh1-02 is used in BA130-5-E10. In both antibodies, the J-segment derived sequences are also human germ-line, JH6. The MEBSD required for specificity of binding to the PcrV antigen is provided by a short sequence within CDRH3, comprised of the D-segment and N-additions from the murine M166 antibody. The heavy chains in each case are paired with human light chains containing CDRL3 sequences from M166.

A Vh library containing human JH3 sequences was prepared and screened in a similar fashion. Approximately 1500 cloned Fab's that contain the Vh MEBSD and a FR4 containing human JH3 sequence, 45 were positive in the CLBA assay for PcrV binding. Individual clones were isolated and soluble Fab' was enriched from the growth media. Each of the purified Fab's was positive in an ELISA assay with the antigen PcrV. The amino acid sequence of the Vh and Vk regions from two of the positive clones is shown in FIG. 7. The M166 Vh MEBSD-region is marked.

Example 4

Focused Vh and Vκ Libraries

The V segment repertoire can be restricted to one subclass of VH or VL before the CDR3-FR4 is appended. Sub-class specific primer sets are used in a PCR reaction with first strand cDNA from an immunoglobulin repertoire. The PCR products are restricted with the appropriate enzymes and cloned into the Fab' expression vector KB1150.

The murine M166 VH reference chain was compared to all human germ-line VH segments and has the highest degree of similarity to the human VH3 subclass. The M166 VL region is most similar to members of the VκI human subclass.

The M166 HCDR3-FR4 was appended to a VH3 subclass segment cRNA library by primer extension; the full VH region was cloned into a Fab' expression vector. The M166 LCDR3-FR4 was appended to a VκI subclass segment cRNA library by primer extension; the full VL region was cloned into the Fab' expression vector that contained the VH3 region library. Eight thousand Fab' expressing clones were assayed by CLBA with PcrV as the target antigen (as described in Example 6) using 10 µM IPTG to induce Fab' expression. Twenty four Fab' clones were positive, indicating that they could specifically bind the PcrV antigen. The clones were isolated and soluble Fab' was purified from the growth media. The individual Fab's were tested in an ELISA with PcrV as the target antigen. All of the selected Fab's bound PcrV.

In each case the Vh chain of the selected Fabs was confirmed to be from the Vh3 subclass and the Vκ chain from the VκI subclass. The frequency of Fab's detected in the CLBA assay was 0.3% with the libraries restricted to Vh3 and VκI compared with a frequency of 0.1% found with the libraries containing a complete representation of human Vh and Vλ sub-classes. This indicates that focused libraries can be used effectively to enhance the frequency of identification of antigen-specific antibodies for further analysis.

Example 5

Colony Lift Binding Assay (CLBA) (General Methods)

Colony lift binding assays for the screening of single-chain antibody libraries have been described (Giovannoni et al.,

*Nucleic Acids Research* 2001, Vol. 29, No. 5 e27). Libraries of human antibody Fab or Fab' fragments secreted from *E. coli* and released into the medium can be screened in a similar manner.

Plating of Bacterial Expressed Antibody Fragment Library

Antibody libraries are transformed into a suitable bacterial host such as the *E. coli* strain TOP10. The transformed culture is plated onto 2YT agar (Becton, Dickinson Difco™ 2xYT yeast extract tryptone medium) containing the appropriate antibiotic (chloramphenicol at 34 µg/ml). The plating efficiency is adjusted so the resulting bacterial colonies are discreet but dense enough to maximize the area of the plate. Various sizes of plate are used depending on the number of clonal colonies to be screened. Thus, at optimal density a 10 cm diameter plate contains 4000 colonies, a 15 cm diameter plate contains 10000 colonies and a 25 cm square plate contains 50,000 colonies.

Coating of Capture-Filter with Antigen

Nitrocellulose filters (Schleicher & Schuell BA85) of diameter 8.2 cm, 13.2 cm or 20 cm square are pre-coated with antigen in Phosphate Buffered Saline (PBS) at an empirically determined concentration (usually between 0.5 and 20 ug/ml). The volume of coating solution depends upon the filter size. 4 ml, 8 ml or 20 ml can be used for the various filter sizes listed above. Filters are placed face down in a pool of the antigen and capillary action evenly distributes the antigen. The filters are coated for 2-3 hours at 33° C. with occasional agitation. The filters are then rinsed once with excess PBS and blocked with a 5% solution of non-fat dry milk in PBS for an additional 2 hours at 25° C. with agitation. The filters are then drained and rinsed once in PBS supplemented with 0.1% Tween 20 (PBST) and twice in excess 2YT liquid media supplemented with antibiotic selection and transcriptional inducer (e.g. chloramphenicol and IPTG). After allowing the filters to drain, they are placed on a 2YT-agar plate supplemented with the same concentration of antibiotic and inducer (the expression plate).

Lifting of Colonies to the Capture Filter

Un-coated, dry nitrocellulose membrane is placed face-down on the plates of colonies containing the antibody-fragment library. Once the filters are visibly wet (~20 sec) and in one movement, the filters are lifted and placed colony side up onto the coated filter which is already on the expression plate. A sterile needle is used pierce the filters in a pattern which will allow alignment.

Expression of Antibody Fragments

The expression plate with the nitrocellulose filter sandwich is placed at 33° C. for 12-16 hours. During this time the antibody fragments are secreted and diffuse through the first nitrocellulose membrane to the second, antigen-coated membrane. If the antibody fragment from a given bacterial colony has antigen binding potential, it is retained on the antigen filter and is subsequently detected.

Detection of Antibody Fragments

After the 12-16 hour expression period the colony filter is removed from the expression plate and stored at 4° C. on a 2YT-agar plate with antibiotic selection but no transcriptional inducer.

The antigen coated filter is removed and washed three times (5 minute washes) in excess PBST followed by blocking with a 5% solution of non-fat dry milk in PBST for 1.5 hours at 25° C. The antibody fragments retained on the antigen filter are then detected by first incubating with one of the following alternative primary antibodies: Goat anti-human Kappa-HRP conjugate (US Biological); 9E10 monoclonal SC-40 (Santa Cruz Biotech); or Penta-His monoclonal (Qiagen Inc.) For 9E10 and Penta-His antibodies, an appropriate secondary peroxidase-conjugated secondary antibody is used to reveal binding. After four 10-minute washes, the filters are incubated in peroxidase substrate solution (ECL plus, Amersham Biosciences) and used to expose light-sensitive photographic film. Alternatively, antibodies conjugated with fluorescent labels may be used. In this case a flatbed excitation scanner such as the Typhoon (Amersham Biosciences) or FX-Pro (Biorad) can be used to visualize the positive spots.

Picking of Positive Colonies

Using a light box for back illumination, the pattern of spots on the photographic film is aligned with the colony filter (this filter can be removed from the 2YT-agar plate and placed on a plastic transparency for this process). The colonies that give a positive signal are picked and used to inoculate a 2YT liquid mini-culture. Bacteria from the primary screen are then replated at a lower density and picked for subsequent analysis to ensure that a clonal population is expanded.

Example 6

Screen for Anti-PcrV Antibodies Using CLBA

Recombinant PcrV, cloned as a fusion protein in frame with an amino terminal glutathione S-transferase (GST) purification tag, has been described previously (Frank et al (2002) J. Infectious Diseases 186: 64-73). The PcrV coding sequence is cloned in the expression vector pGEX 2TK (Amersham) to generate the GST-PcrV fusion protein.

GST-PcrV fusion protein was expressed from *E. coli* (BL21) transformed with pGEX 2TK-PcrV and purified as follows. 4 liter liquid culture batches of *E. coli* expressing GST-PcrV were grown in 2YT to an optical density of 0.6 at 600 nm before induction of protein expression with 0.5 mM IPTG and a further 3 hours growth. The bacterial cells were pelleted by centrifugation and lysed in a solution of Bug Buster (Novagen) supplemented with 1 U/ml rLysozyme (Novagen) and a protease inhibitor cocktail (Sigma-Aldrich) diluted to the manufacturer's instructions. After clearing the lysate by centrifugation and filtration it was past over a glutathione sepharose column (GSTrap FF, Amersham biosciences), washed and the pure GST-PcrV was eluted in 10 mM Glutathione. The antigen was desalted back into PBS and used to coat nitrocellulose filters for CLBA at concentrations of 2-20 µg/ml. CLBA was carried out as in Example 5.

For libraries expressed in KB1082, libraries were plated on 2YT expression plates containing chloramphenicol [34 µg/ml] and arabinose [0.002%]. Cells were induced for 16 hours and antibody fragments binding to GST-PcrV on the antigen-coated filter were detected using a goat anti-human kappa antibody–Horseradish peroxidase conjugate (US Biological) at a dilution of 1/5000 in PBST. +After 4×15 minute washes and the application of ECL Plus (Amersham biosciences), the filters were used to expose auto radiographic film (Hyperfilm from Amersham biosciences).

Nitrocellulose filters were initially coated with GST-PcrV at a concentration of 20 µg/ml. Two independent library screens were completed. For library BA19 15,000 colonies were plated and screened with 12 colonies giving a positive signal indicating the presence of a Fab with PcrV binding potential. For Library BA46>50,000 colonies were screened resulting in >200 positive signals. The positive colonies from both libraries were picked and plated at lower density. Individual clones were grown in liquid culture and Fab expression into the growth media was induced. Those clones that gave a strong signal in subsequent ELISA assays for GST-PcrV binding were further analyzed in dilution ELISA and Biacore analysis as described in examples 7 and 8.

Subsequent screens on lower antigen densities (2 µg/ml coating concentration) gave fewer positive clones but ELISA and Biacore analysis showed the higher stringency screen resulted in higher affinity Fab fragments. The stringency of the screens can thus be set to select antibody fragments with equal or higher affinity than the murine parental antibody.

For libraries expressed in KB1150, expression plates were prepared with chloramphenicol [34 µg/ml] and either had no inducer or contained 10-20 µM IPTG. Colonies on the lift filter were cultured on the expression plate for 16 hours and antibodies binding to GST-PcrV were detected using goat anti-kappa-HRP conjugate (US Biological) as above.

As with the positive clones from libraries expressed in KB1082, those resulting from screens in KB1150 were picked and plated at lower density.

Example 7

Detection of Human Anti-PcrV Antibodies by ELISA

Positive colonies from the CLBA were streaked on a 2YT-agar plate containing relevant antibiotics but no transcriptional induction. 6-8 colonies from each streak were individually inoculated in 2YT liquid culture in duplicate deep 96-well titer plates. One replica plate was grown for 16 hours, supplemented with glycerol to 15% and stored at −80° C. as a glycerol stock. The other replica plate was grown at 33° C. in a shaking incubator until an optical density of 0.5-0.8 at 600 nm was achieved at which point antibody fragment expression was induced using 0.01% arabinose for those Fabs expressed in KB1082 or 0.5M IPTG for KB1150. A further 16 hours growth resulted in accumulation of antibody fragments in the growth medium.

ELISA plates (Costar EIA/RIA) were coated with 100 ng/well GST-PcrV in PBS by incubating them at 4° C. for 16 hours and blocked for 1 hour with a 5% solution of non-fat dry milk in PBS 0.1% Tween 20 (PBST). Samples of media were cleared of cell debris by centrifugation and applied to the ELISA plate for 1 hour at 33° C. After washing with PBST, antibody fragments binding to the antigen were detected with either anti-peptide tag (9E10, Santa Cruz biotech), at a dilution of 1/1000 in PBST followed by Goat anti-mouse polyclonal—HRP conjugate (Dakocytomation) at a dilution of 1/1000 in PBST, or goat anti-human kappa-HRP conjugate (US Biological) at a dilution of 1/1000 in PBST. Antibody binding was revealed using the peroxidase substrate Tetramethyl benzidine (TMB) (100 µl/well), and the reaction was stopped with the addition of 100 ul 2N $H_2SO_4$ and read by a standard plate-reader.

The alignment of the positive ELISA signals with the replicate glycerol stocks allowed for the picking of one of the 6-8 cultures for each original CLBA clone. Selected antigen-binding clones were purified for determination of antibody-binding affinity by surface plasmon resonance (Example 8).

In some experiments, ELISA was used for primary screening of pools of up to 20 bacterial colonies obtained from the antibody library.

380 pools, each containing an estimated 13 bacterial colonies/well from Library BA19 were cultured overnight in 96-well microtiter plates under inducing conditions (0.02% arabinose). Culture supernatants were screened by ELISA for antibody fragments binding to GST-PcrV. Antigen-binding antibody fragments were detected using mouse anti-Penta-His (Qiagen) diluted 1:100 in PBST and revealed using HRP-conjugated goat anti-mouse antibody (Dakocytomation) 1:500 in PBST and TMB substrate. A single positive well was identified which showed strong binding to antigen. Cells from this pool were obtained from a replica glycerol plate and grown at low density on 2YT agar. 24 sub-clones were screened by antigen-binding ELISA and two clones were identified with high affinity for PcrV antigen, both of which expressed antibody fragments of identical sequence.

ELISA assays were also used to determine relative binding affinities of purified antibody fragments expressed from bacteria. His-tagged antibody fragments were purified using Ni-sepharose as follows. One liter liquid cultures of E. coli expressing the antibody fragments were grown to an optical density of 0.6 at 600 nm before induction with the addition of arabinose to a final concentration 0.01%. The cultures were grown for a further 3 hours at 33° C. prior to harvesting the cells by centrifugation. The cells were fractionated and the periplasmic fractions retained as follows. The bacterial cell pellet from a 1 liter culture was resuspended in 10 ml of TES buffer (0.2M Tris pH 8.0, 17.12% sucrose and 0.5 mM EDTA) and incubated at 4° C. for 15 minutes. After the addition of 12.5 ml of TES/$H_2O$ at a ratio of 1/4 the cell mixture was incubated at 4° C. for a further 15 minutes. The cells were pelleted by centrifugation at 7000 rcf for 15 minutes and the supernatant was kept. The pellet was then resuspended in 10 ml TES supplemented with 15 mM $Mg_2SO_4$ and incubated at 4° C. for 10 minutes followed by repelleting. The supernatants were pooled, dialyzed against PBS and antibody fragments were purified on Ni-NTA (Invitrogen) according to the manufacturer's instructions. Fab' fragments without a C-terminal tag were purified by Protein G affinity purification using HiTrap Protein G HP columns (Amersham Biosciences). Antibody fragments were checked for purity by SDS-PAGE and staining with Coomassie Blue. Antibody fragment concentrations were determined by densitometry of the Coomassie-stained gel in comparison with a bovine serum albumin (BSA) standard, using a ChemiDoc XRS (Bio-Rad Laboratories, Inc.). The variable regions (VH and VL) of the Mouse Mab 166 were cloned, expressed and purified from E. coli in this way. The Murine Fab was then used as a standard in the following ELISA and Biacore assays. Dilution ELISAs on purified antibody fragment samples were run with the same basic procedure described above for screening bacterial medium samples. Fabs were diluted to the same starting concentration in 100 µl of PBS. A two fold dilution series across a 96-well microtiter plate was set up for each Fab in duplicate. This series was then applied to the pre-coated and blocked ELISA plate. After washing in PBST the bound Fab was detected as described above. This assay allowed for the affinity ranking of the Fabs prior to Biacore analysis. Examples of the data generated by this assay are shown in FIG. 8.

Example 8

Analysis of Affinities of Anti-PcrV Antibodies by Surface Plasmon Resonance

Binding kinetics were analyzed by surface plasmon resonance using a Biacore 3000 analyzer (Pharmacia). The GST-PcrV antigen was coated onto the sensor chip at up to three different densities (20-300 RU). Immobilization was done on a CM4 sensor chip using standard amine coupling chemistry. The running buffer was 10 mM HEPES, 150 mM NaCl, 0.005% P20, 3 mM EDTA, and 0.2 mg/ml BSA (pH 7.4). Fab samples were applied to up to 3 different GST-PcrV density chips in duplicate. Bound complexes were regenerated with a 12 second pulse of 1/200 dilution of phosphoric acid. The mean binding response data from the different density surfaces were globally fit to determine the binding constants shown in the table below. The variable regions (VH and VL) from Mab 166 were also cloned and expressed from *E. coli* as a chimeric Fab fragment. Selected human Fab fragments could thus be compared with the starting murine Fab for binding kinetics (Murine Fab M166).

TABLE 1

Kinetics of binding of Fab fragments to recombinant PcrV antigen determined by surface plasmon resonance analysis. Data represent the means of three determinations.

| Fab | ka (M-1s-1) | kd (s-1) | KD (nM) |
|---|---|---|---|
| M166 (murine) | 2.49E+5 | 2.6E−4 | 1.1 |
| A10 | 3.3E+5 | 7.4E−04 | 2.2 |
| F6 | 1.44E+5 | 2.55E−3 | 17.7 |
| 1F1 | 7.91E+5 | 8.87E−4 | 1.13 |
| 1A8 | 1.60E+5 | 1.35E−4 | 0.726 |
| BA89 | 3.4E+5 | 5.8E−5 | 0.174 |
| BA90 | 3.4E+5 | 5.3E−5 | 0.160 |

Human Fabs were isolated by CLBA and ELISA screening with different binding kinetics. Several Fabs had affinities comparable to the affinity of the murine reference Fab and Fab1A8 had a significantly higher affinity and a significantly lower dissociation rate than Mab166 Fab (Table 1).

BA89 and BA90 are derivatives of Fab-1A8 generated using parsimonious mutagenesis according to previously described methods (Balint and Larrick *Gene* 137:109-18, 1993) in order to generate single amino-acid mutations in CDRH3 and CDRL3. Mutant derivatives were screened by CLBA at high stringency. The affinities of these two antibodies are higher and the dissociation rates are lower than 1A8 (Table 1).

TABLE 2

Comparison of V-region sequences with the closest human germ-line sequences. The amino-acid sequences of the V-regions of each antibody were compared to the database of human germ-line sequences and the percent identity to the closest human germline is shown for each V-region excluding the CDR3 sequences.

| Clone | Vh versus: | % Identity to Human Germline | Vκ versus: | % Identity to Human Germline |
|---|---|---|---|---|
| M166 (murine) | VH3-33 | 63 | VκI A20 | 71 |
| A10 | VH3-30.3 | 93 | VκIII L6 | 98 |
| F6 | VH3-33 | 98 | VκIII A27 | 92 |
| 1F1 | VH3-30.3 | 93 | VκIII L6 | 99 |
| 1A8 | VH3-30.3 | 93 | VκI L12 | 87 |
| BA89 | VH3-30.3 | 94 | VκI L12 | 88 |
| BA90 | VH3-30.3 | 94 | VκI L12 | 88 |

This analysis demonstrates that high affinity anti-PcrV antibodies can be isolated using the CLBA. The sequence of each of the anti-PcrV antibodies was compared with the database of human germ-line sequences and the percent of amino-acids identical to those of the closest human germ-line sequence is shown in Table 2. Each of the antibodies shows significantly higher homology with human germ-line sequences than the M166 murine reference antibody in both the VH and VL regions. Indeed, the complete V-regions for each antibody show a high degree of sequence identity with a germ-line human chain. (The CDR3 sequences were excluded from this analysis as they contain the binding specificity determinants for these antibodies). The sequences of the V-regions of two of the antibodies, F6 and 1F1 are shown in FIG. 9. F6 has a VH-segment which is completely identical to a human germ-line V-segment (VH3-33). 1F1 has a VL-segment which is identical to germ-line VκIII L6. Thus, the methods described here have succeeded in identifying high affinity antibodies to PcrV with a high degree of homology to human germ-line antibody sequences. In some cases, at least one of the V-regions has a V-segment which is completely identical to a germ-line sequence.

Example 9

Antagonism of Type III Secretion System by Human Fabs to PcrV

The *Pseudomonas* Type III secretion system (TTSS) mediates the direct translocation of *Pseudomonas* exotoxins from the bacteria to host cells with which it comes into contact. Hence *Pseudomonas* strains expressing exotoxins show potent cytotoxic activity towards all mammalian cell types.

An exotoxin-dependent cytotoxicity assay was established using the mouse myeloma cell line P3-X63-Ag8 as the target. $2 \times 10^5$ cells were infected with *P. aeruginosa* strain PA103 at an MOI of 10. After 3 hours, cells were stained with Propidium Iodide and the proportion of permeabilized cells was quantified by flow cytometry. At this time point approximately 50% of cells were stained with Propidium Iodide. Mab 166 has been shown to block TTSS-mediated exotoxin secretion and prevent cell-killing by *Pseudomonas* strain PA103 (Frank et al 2002. J. Infect. Disease 186:64). For antibody inhibition experiments, human Fab fragments or Mab 166 whole IgG were incubated together with X63 cells and *Pseudomonas* PA103 as described above. In this assay, Fab-1A8 and murine Mab 166 IgG both showed effective inhibition of *Pseudomonas*-mediated cytotoxicity. The $IC_{50}$ for Fab-1A8 was determined to be 68 nM$^\pm$1.1 nM, compared with an $IC_{50}$ of 93 nM$^\pm$1.1 nM for Mab 166. (Data represent mean$^\pm$standard error of means, determined from 3 independent assays, expressed as concentration of antibody binding sites).

This indicates that Fab1A8 retains the biological activity of the Mab 166 reference antibody, demonstrating potent antagonist activity against TTSS-mediated cytotoxicity. The higher potency of Fab 1A8 compared with Mab166 in the cell-based assay is consistent with its higher affinity for recombinant PcrV antigen determined by surface plasmon resonance analysis.

Example 10

Expression and Secretion of Human Fab Fragments in Yeast

For expression and secretion of Fab fragments from *S. cerevisiae*, a yeast invertase (SUC2) signal-peptide was chosen for fusion to the N-terminus of the mature protein sequence for both the heavy and light chains. The coding sequences were then introduced into a yeast expression vector, pESC-Trp (Stratagene) which has a trp selectable marker and insertion sites for two coding sequences under the control of galactose-regulated promoters.

The Fd fragment of human anti-PcrV antibody 1A8 was amplified by two-step nested PCR reactions from 1A8 plasmid DNA using overlapped PCR primers pr37/pr32 and pr33/pr34. The primers also serve to introduce sequences encoding a yeast invertase secretion signal upstream of the heavy chain coding sequence. The Fd sequence was amplified for 15 cycles with pr32 plus pr37. The PCR fragment was then gel-purified and amplified for 15 cycles with pr33 plus pr34 and re-purified. PCR fragments were digested with Bgl II plus Sac II and ligated into pESC-Trp cut with BamH I plus Sac II in the multiple cloning sites downstream from the Gal1 promoter to make pSC0021-3.

```
Primer 32:
                                          (SEQ ID NO: 127)
CAGAAATCAATTTCTGTTCCATAGAACCACCGCCACCACAAGATTTGGGC

TCAACTTTC

Primer 37:
                                          (SEQ ID NO: 128)
CTTGTTCTTAGCTGGTTTTGCTGCCAAGATATCTGCTGAGGTGCAGCTGG

TGGAG

Primer 33:
                                          (SEQ ID NO: 129)
AACCCCAGATCTGTCGACCACCATGTTGTTACAAGCCTTCTTGTTCTTAG

CTGGTTTTGC

Primer 34:
                                          (SEQ ID NO: 130)
GATCTTAGCTAGCCGCGGTTAGTTCATCCTCTTCAGAAATCAATTTCTGT

TCCATAG
```

Primers (pr66/pr67 and pr68/pr67) were used to amplify the light chain of Fab-1A8 by nested PCR reaction. The primers also provide the yeast invertase secretion signal upstream of the light chain. The light chain was amplified for 15 cycles with pr66 plus pr67. The PCR fragment was then gel-purified and amplified for 15 cycles with pr68 plus pr67, and re-purified. PCR fragments were digested with EcoRI plus BamH I and ligated into pESC-Trp cut with EcoRI plus Bgl II in the multiple cloning sites downstream from the Gal10 promoter to make pSC0017-2.

```
Primer 66:
                                          (SEQ ID NO: 131)
CTTATTCCTGGCTGGTTTCGCTGCTAAGATCTCTGCTGACATCCAGTTGA

CCCAGTCTC

Primer 67:
                                          (SEQ ID NO: 132)
CACTAGACATGGATCCATATGCTAACACTCTCCCCTGTTGAAGCTC Primer 68:
                                          (SEQ ID NO: 133)
TGAAAATTCGAATTCCACCATGTTATTGCAAGCTTTCTTATTCCTGGCTG

GTTTCGC
```

To construct a double-gene vector for expression of both heavy and light chains, the 1.5 kb EcoRI-NheI fragment from pSC0021-3, containing the Fd coding sequence, was subcloned into the light-chain expression vector pSC0017-2, digested with the same enzymes, to make pSC0019-1. In this vector, expression of the light chain is directed from the GAL10 promoter and the Fd chain is expressed from the GAL1 promoter. Expression of both chains is induced in media lacking galactose.
Detection of Fab-1A8 Secreted into the Medium Yeast strain YPH499 was obtained from Stratagene and growth and transformation were carried out according to the manufacturer's instructions (pESC Yeast epitope-tagging vectors: Instruction Manual revision # 104002d; Stratagene). Briefly, the YPH499 cells were streaked from a glycerol stock onto a YPAD plate and incubated at 30° C. for two days until colonies appeared. Fresh competent cells were prepared from the YPH499 colonies and used for transformation with 1 µg of pSC0019-1 DNA. The transformation reactions were plated onto SD dropout plates and incubated at 30° C. for three days to select transformants.

For expression of antibody fragments, six colonies from each transformation were inoculated into 5 ml of SD dropout medium (which contains 2% glucose), and incubated with shaking (350 rpm) for overnight. The $OD_{600\ nm}$ was determined the next day and sufficient cells were centrifuged and resuspended in SG dropout medium (which contains 2% galactose) to generate a culture with OD of 0.25. Expression of Fab fragment was induced by culture in SG dropout medium with shaking (350 rpm) at 30° C. for 16 hours. After induction, the cells were cleared from the media by centrifugation twice and the supernatants were collected for detection of secreted Fab fragment by ELISA and Western blot analysis.

Expression of assembled Fab was confirmed by Western blotting using detection with HRP-conjugated anti-human kappa antibody (US Biological). Antigen-binding ELISAs were carried out on supernatants from induced cultures and the binding to GST-PcrV antigen was detected with HRP-conjugated anti-human kappa antibody thus confirming secretion of active Fab into the medium.

For screening of libraries of human Fabs, the V-region sequences in pSC0019-1 are replaced by libraries of VH and VL sequences using standard recombinant DNA techniques. Fab fragments secreted from yeast transformants are detected by antigen-binding ELISA as described above, or by colony-lift binding assay.

Example 11

Colony Lift Binding Assay (CLBA) in Yeast

The CLBA methodology for antibody secretion and detection in yeast is essentially the same as described for bacterial colonies in Example 5. Yeast cultures containing the vector pSC0019-1 DNA with either a PcrV-binding Fab or a negative control Fab were grown for 16 hours at 30° C. in SD dropout minimal medium. The optical density of the cultures at 600 nm was measured and 1000 cells of each culture were plated onto separate SD dropout agar plates (growth plates). Small discrete colonies were seen after 16 hrs growth at 30° C. A nitrocellulose filter was coated with 20 µg/ml GST-PcrV and blocked with a 5% milk solution as described in example 5. The antigen coated filter was rinsed in SG dropout media prior to placing it on an SG dropout agar plate (expression plate). Colonies on the growth plate were lifted onto a nitrocellulose filter which was then placed on top of an antigen coated filter on the expression plate. The expression plate was then incubated for a further 16 hours at 30° C. The HRP-conjugated anti-human kappa antibody (US Biological) was used for detection of the antibody Fab fragments as described in Examples 5 and 6.

On exposure to radiographic film the antigen filter from the plate of Fab-1A8 colonies showed positive signals corresponding to colonies secreting anti-PcrV Fab while the negative control was blank. This indicates that the CLBA can be used to screen libraries of antibody fragments expressed and secreted from yeast.

All publications, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of making an antibody having a binding specificity of a reference antibody that binds to an antigen, the method comprising
   a) recombinantly joining a heavy chain CDR3D segment from the reference antibody, which CDR3D segment is linked to a FR4, to an unselected member of a diverse population of human FR1-CDR1-FR2-CDR2-FR3 $V_H$ segments from human cells, thereby creating a library of $V_H$ regions that comprises members that have the reference antibody heavy chain CDR3D segment linked to diverse unselected human FR1-CDR1-FR2-CDR2-FR3 $V_H$ segments;
   b) recombinantly joining a light chain CDR3BSD from the reference antibody, which reference antibody light chain CDR3BSD is linked to a Jκ germline FR4 to provide a light chain CDR3BSD-Jκ germline FR4, to an unselected member of a diverse population of human FR1-CDR1-FR2-CDR2-FR3$V_L$ segments obtained from human cells, thereby creating a library of $V_L$ regions that comprises members that have the CDR3BSD-Jκ germline FR4 linked to diverse unselected human FR1-CDR1-FR2-CDR2-FR3$V_L$ segments;
   c) combining the libraries of step a and step b to create an antibody library wherein the members of the antibody library comprise a diversity of $V_H$ regions and a diversity of $V_L$ regions that have the reference antibody heavy chain CDR3D segment and the light chain CDR3BSD-Jκ germline FR4; and
   d) screening the library of step c and isolating a member of the library that binds to the antigen.

2. The method of claim 1, wherein the diverse population of human FR1-CDR1-FR2-CDR2-FR3 $V_H$ segments are human germline $V_H$ segments or the diverse population of human FR1-CDR1-FR2-CDR2-FR3 $V_L$ segments are human germline $V_L$ segments.

3. The method of claim 1, wherein both the diverse population of human FR1-CDR1-FR2-CDR2-FR3 $V_H$ segments from human cells and the diverse population of human FR1-CDR1-FR2-CDR2-FR3 $V_L$ segments from human cells are human germline segments.

4. The method of claim 1, wherein the diverse population of human FR1-CDR1-FR2-CDR2-FR3 $V_H$ segments is from one human FR1-CDR1-FR2-CDR2-FR3 V segment subclass.

5. The method of claim 1, wherein the diverse population of human FR1-CDR1-FR2-CDR2-FR3 $V_L$ segments is from one human FR1-CDR1-FR2-CDR2-FR3 V segment subclass.

6. The method of claim 1, wherein the step of isolating a member of the library of step c comprises a screening step to identify a member of the library that binds to the antigen with the same or higher affinity than the reference antibody.

7. The method of claim 1, wherein the reference antibody is a nonhuman antibody.

8. The method of claim 1, wherein the step of combining the libraries comprises expressing the library of $V_H$ regions and the library of $V_L$ regions on a single expression vector.

9. The method of claim 8, wherein the $V_H$ library and the $V_L$ library are expressed using separate promoters.

10. The method of claim 1, wherein the step of combining the libraries comprises expressing the library of $V_H$ regions and the library of $V_L$ regions on two expression vectors.

11. The method of claim 1, wherein the human antibody library of step c) comprises antibodies where an antibody is an IgG, an Fv, an Fab, an Fab', an F(ab')2, a single chain Fv, or an IgG with a deletion of one or more domains.

12. The method of claim 1, wherein the step of isolating the members of the library comprises screening using a colony lift binding assay.

13. The method of claim 1, wherein the step of isolating the members of the library comprises screening using bacterial cell display or yeast cell display technology.

14. The method of claim 1, wherein the step of isolating the members of the library comprises screening pools of library members.

* * * * *